US010217620B2

(12) United States Patent
Röder et al.

(10) Patent No.: US 10,217,620 B2
(45) Date of Patent: Feb. 26, 2019

(54) EARLY DETECTION OF HEPATOCELLULAR CARCINOMA IN HIGH RISK POPULATIONS USING MALDI-TOF MASS SPECTROMETRY

(71) Applicant: Biodesix, Inc., Boulder, CO (US)

(72) Inventors: Joanna Röder, Steamboat Springs, CO (US); Carlos Oliveira, Steamboat Springs, CO (US); Julia Grigorieva, Steamboat Springs, CO (US); Heinrich Röder, Steamboat Springs, CO (US); Devalingam Mahalingam, San Antonio, TX (US)

(73) Assignee: Biodesix, Inc., Boulder, CO (US)

( * ) Notice: Subject to any disclaimer, the term of this patent is extended or adjusted under 35 U.S.C. 154(b) by 0 days.

(21) Appl. No.: 16/020,183

(22) Filed: Jun. 27, 2018

(65) Prior Publication Data

US 2018/0323049 A1 Nov. 8, 2018

Related U.S. Application Data

(63) Continuation of application No. 14/936,847, filed on Nov. 10, 2015, now Pat. No. 10,037,874.
(Continued)

(51) Int. Cl.
*H01J 49/00* (2006.01)
*G06K 9/62* (2006.01)
(Continued)

(52) U.S. Cl.
CPC .... *H01J 49/0036* (2013.01); *G01N 33/57438* (2013.01); *G01N 33/6851* (2013.01);
(Continued)

(58) Field of Classification Search
USPC .................................. 250/282, 287
See application file for complete search history.

(56) References Cited

U.S. PATENT DOCUMENTS 5,650,275 A * 7/1997 Pitner ..................... C12Q 1/68
435/6.19
7,736,905 B2 6/2010 Roder
(Continued)

FOREIGN PATENT DOCUMENTS

| WO | 07/126758 A2 | 11/2007 |
| WO | 10/085234 A1 | 7/2010 |
| WO | 10/085235 A1 | 7/2010 |

OTHER PUBLICATIONS

Girosi et al., "Regularization Theory and Neural Networks Architectures", Neural Computation, 7:219-269 (1995)*.
(Continued)

*Primary Examiner* — Kiet T Nguyen
(74) *Attorney, Agent, or Firm* — McDonnell Boehnen Hulbert & Berghoff LLP

(57) ABSTRACT

Hepatocellular carcinoma (HCC) is detected in a patient with liver disease. Mass spectrometry data from a blood-based sample from the patient is compared to a reference set of mass-spectrometry data from a multitude of other patients with liver disease, including patients with and without HCC, in a general purpose computer configured as a classifier. The classifier generates a class label, such as HCC or No HCC, for the test sample. A laboratory system for early detection of HCC in patients with liver disease is also disclosed. Alternative testing strategies using AFP measurement and a reference set for classification in the form of class-labeled mass spectral data from blood-based samples of lung cancer patients are also described, including multi-stage testing.

10 Claims, 14 Drawing Sheets

Related U.S. Application Data

(60) Provisional application No. 62/086,805, filed on Dec. 3, 2014.

(51) Int. Cl.
    *G01N 33/574*   (2006.01)
    *G01N 33/68*    (2006.01)
    *H01J 49/16*    (2006.01)
    *G16H 10/40*    (2018.01)
    *G16H 50/70*    (2018.01)
    *G06K 9/00*     (2006.01)

(52) U.S. Cl.
    CPC ....... *G06K 9/00147* (2013.01); *G06K 9/6228* (2013.01); *G06K 9/6276* (2013.01); *G16H 10/40* (2018.01); *G16H 50/70* (2018.01); *H01J 49/164* (2013.01); *G06K 9/00536* (2013.01); *Y02A 90/26* (2018.01)

(56) References Cited

U.S. PATENT DOCUMENTS

| | | |
|---|---|---|
| 8,119,417 B2 | 2/2012 | Roder |
| 8,119,418 B2 | 2/2012 | Roder |
| 8,354,234 B2 | 1/2013 | Chen |
| 8,718,996 B2 | 5/2014 | Roder |
| 9,563,744 B1 | 2/2017 | Roder |
| 2004/0234973 A1* | 11/2004 | Adorjan ............... C12Q 1/6883 435/6.16 |
| 2005/0065732 A1 | 3/2005 | Tilton |
| 2011/0208433 A1 | 8/2011 | Grigorieva |
| 2012/0193525 A1 | 8/2012 | Roder |
| 2013/0320203 A1 | 12/2013 | Roder |
| 2013/0344111 A1 | 12/2013 | Roder |
| 2015/0102216 A1 | 4/2015 | Roder |
| 2015/0283206 A1 | 10/2015 | Roder |

OTHER PUBLICATIONS

Srivastava, "Improving Neural Networks with Dropout", Master Thesis, Graduate Department of Computer Science, University of Toronto 2013*.
Taguchi et al., "Mass Spectrometry to Classify Non-Small-Cell Lung Cancer Patients for Clinical Outcome After Treatment with Epidermal Growth Factor Receptor Tyrosine Kinase Inhibitors: A Multicohort Cross-Institutional Study" JNCI 99(11):838-846 (2007)*.
Tibshirani, "Regression Shrinkage and Selection via the Lasso", J. R. Statist. Soc. B, 58(1):267-288 (1996)*.
Tikhonov, "On the Stability of Inverse Problems", Comptes Rendus (Doklady) de l'Academie des Sciences de l'URSS, vol. XXXIX, N. 5:195-198 (1943)*.
Singal et al., "Meta-analysis: surveillance with ultrasound for early-stage hepatocellular carcinoma in patients with cirrhosis", Ailment Pharmacol. Ther., 30(1):37-47 (2009)*.
Schwegler et al., "SELDI-TOF MS Profiling of Serum for Detection of the Progression of Chronic Hepatitis C to Hepatocellular Carcinoma", Hepatology, 41:634-642 (2005)*.
Ward et al., "Changes in the serum proteome associated with the development of hepatocellular carcinoma in hepatitis C-related cirrhosis", British Journal of Cancer, 94:287-292 (2006)*.
Ward et al., "Preclinical and post-treatment changes in the HCC associated serum proteome", British Journal of Cancer, 95:1379-1383 (2006)*.
Flores et al., "Emerging Trends in Hepatocellular Carcinoma: Focus on Diagnosis and Therapeutics", Clinical Medicine Insights: Oncology, 8:71-76 (2014)*.
Prieto et al., "DKK1 as a serum biomarker for hepatocellular carcinoma", Hepatobiliary Surg. Nutr. 2(3):127-128 (2013).
Shang et al., "Identification of Osteopontin as a Novel Marker for Early Hepatocellular Carcinoma", Hepatology, 55(2):483-490 (2012)*.
Kim et al., "Development of Biomarkers for Screening Hepatocellular Carcinoma Using Global Data Mining and Multiple Reaction Monitoring", PLOS One, 8(5):1-11 (2013)*.
Li et al., "Micro-ribonucleic acids: potential noninvasive biomarkers for hepatocellular carcinoma", Journal of Hepatocellular Carcinoma, 1:21-33 (2014)*.
Liu et al., "MALDI-TOF MS Combined with magnetic Beads for Detecting Serum Protein Biomarkers and Establishment of Boosting Decision Tree Model for Diagnosis of Hepatocellular Carcinoma", Am. J. Clin. Pathol. 134:235-241 (2010)*.
Kimhofer et al., "Proteomic and metabonomic biomarkers for hepatocellular carcinoma: a comprehensive review", British Journal of Cancer 2015 112:1141*.
Ressom et al., "Analysis of MALDI-TOF Mass Spectrometry Data for Discovery of Peptide and Glycan Biomarkers of Hepatocellular Carcinoma", J. Proteome Res., 7(2):603-610 (2008)*.

\* cited by examiner

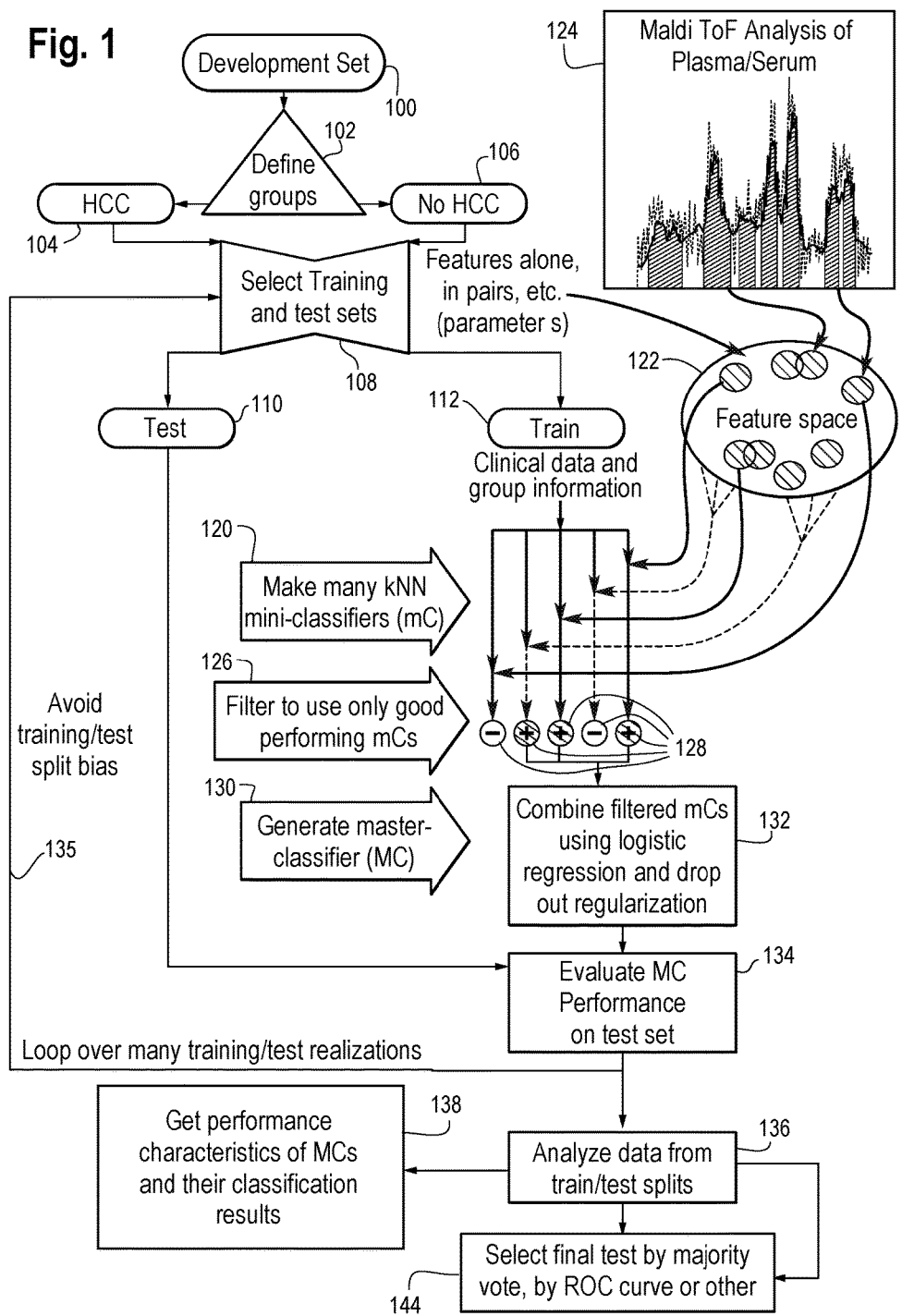

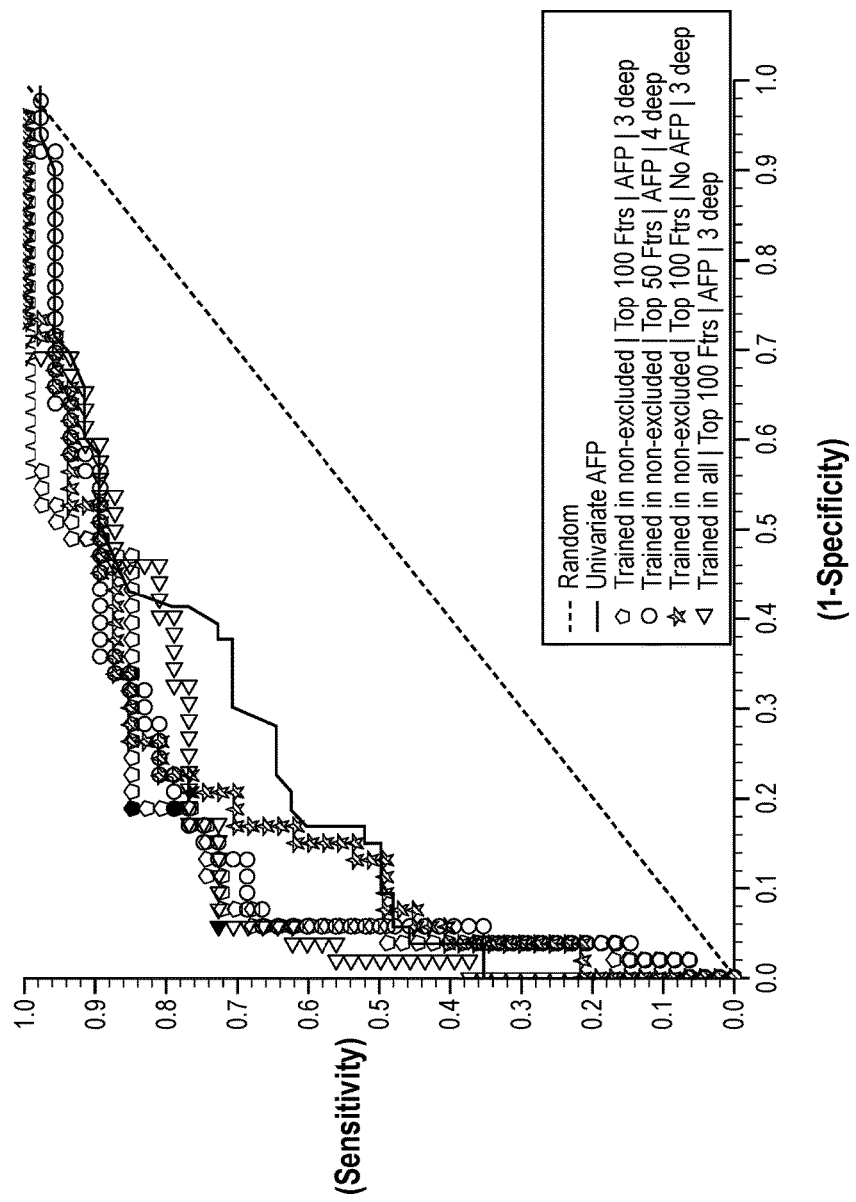

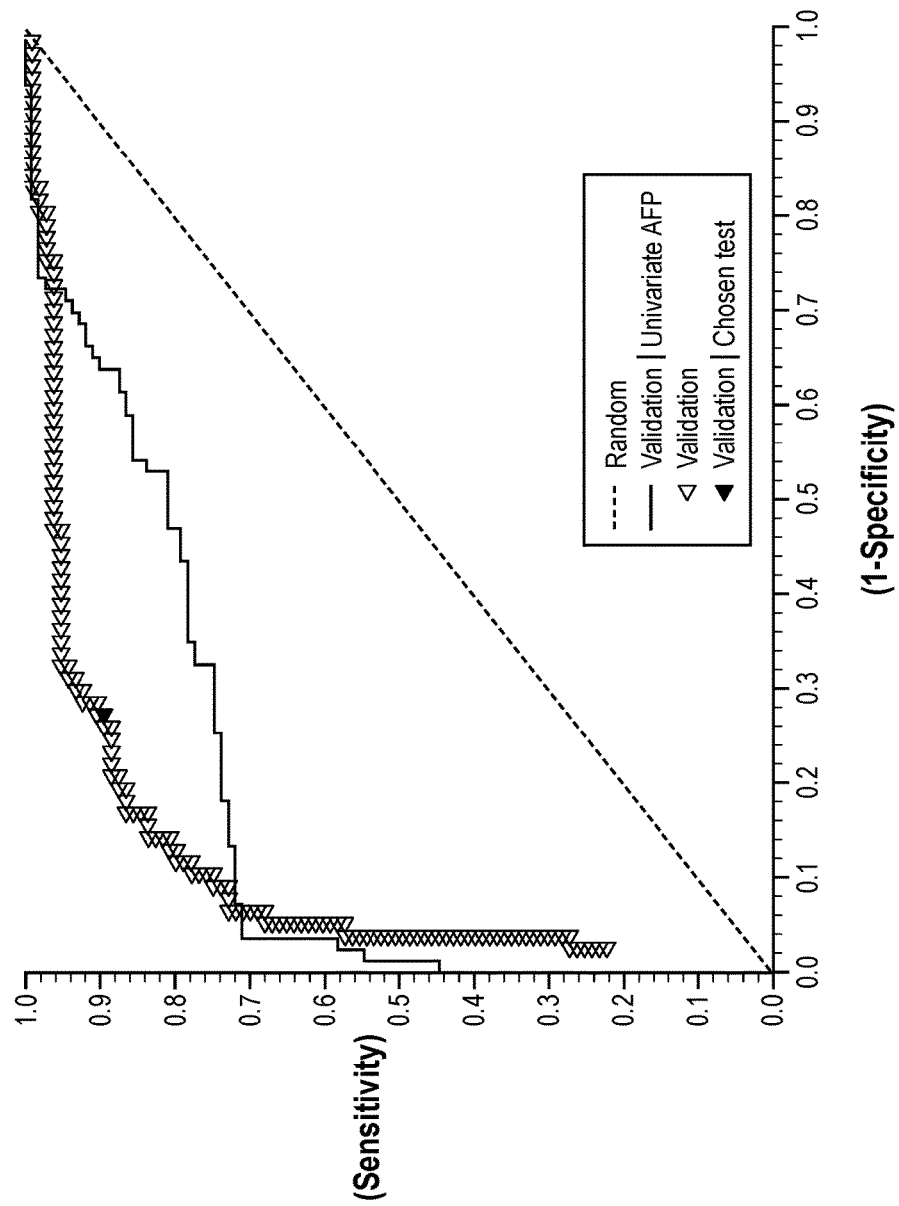

EARLY DETECTION OF HEPATOCELLULAR CARCINOMA IN HIGH RISK POPULATIONS USING MALDI-TOF MASS SPECTROMETRY

PRIORITY

This application is a continuation of U.S. Ser. No. 14/936,847, filed Nov. 10, 2015, which claims the benefit under 35 U.S.C. § 119 to U.S. provisional application Ser. No. 62/086,805 filed Dec. 3, 2014, the contents of which are all incorporated by reference herein.

BACKGROUND

Hepatocellular carcinoma (HCC) is the most common of the hepatobiliary (liver, gall bladder and bile duct) cancers and the fourth most common cancer worldwide. National Comprehensive Cancer Network (NCCN) Clinical Practice Guidelines in Oncology: Hepatobiliary Cancers Version 1 (2013). According to the National Cancer Institute's cancer.gov website, it is estimated that around 33,000 new cases of HCC will be diagnosed and 23,000 deaths will occur due to this disease in the United States in 2014. Risk factors for HCC include infection with hepatitis B virus (HBV) or hepatitis C virus (HCV), alcoholic cirrhosis, and other liver conditions, such as hemochromatosis or late stage primary biliary cirrhosis (PBC). NCCN Guidelines, supra. The incidence of HCC in patients with these conditions is sufficient to allow them to constitute a feasible high-risk screening population.

Measurement of serum alphafetoprotein (AFP) and liver ultrasonography at intervals of 6-12 months are used for HCC screening in the high risk population. However, the American Association for the Study of Liver Disease (AASLD) guidelines no longer recommend AFP testing as part of a diagnostic evaluation (see NCCN Guidelines, supra), due to lack of adequate sensitivity or specificity. While high levels of serum AFP can be considered diagnostic of HCC, they occur in only a relatively small percentage of patients with HCC. It has been shown in a meta-analysis by Dr. Singal et al. that measurement of AFP provided no additional benefit to ultrasound screening for detection of early stage HCC. A. Singal, et al., *Meta-analysis: Surveillance With Ultrasound for Early-stage Hepatocellular Carcinoma in Patients with Cirrhosis* Aliment Pharmacol. Ther. vol. 30 no. 1 pp. 37-47 (2009). However, additional imaging studies and more frequent monitoring are still recommended for patients with rising levels of AFP. Ultrasound evaluations suffer from lack of inter- and intra-operator and machine variability and may be difficult in obese patients. While CT scans with contrast allow for the detection of much smaller tumors or nodules than ultrasound (<1 cm), these cannot be carried out in patients with renal insufficiency and the radiation dose from repeated CT scans in a screening setting may be problematic.

Exploratory serum biomarkers being studied in the context of HCC detection and diagnosis include des-gamma-carboxy prothrombin (DCP), also known as protein induced by vitamin K absence-II (PIVKA-II), and lens culinaris agglutinin-reactive AFP (AFP-L3), an isoform of AFP. Prior art of interest relating to HCC biomarkers includes E. E. Schwegler et al. *SELDI-TOF MS profiling of serum for detection of the progression of Chronic Hepatitis C to Hepatocellular Carcinoma* Hepatology vol. 41 no. 3 pp. 634-642 (2005); D. G. Ward et al., *Changes in serum proteome associated with the development of hepatocellular carcinoma in hepatitis C-related cirrhosis* British Journal of Cancer vol. 94 pp. 287-292 (2006); D. W. Ward, et al., *Preclinical and post-treatment changes in the HCC-associated serum proteome* British Journal of Cancer vol. 95 p. 1379-1383 (2005). Other prior art of interest includes A. Flores et al., *Emerging trends in hepatocellular carcinoma: Focus on Diagnosis and Therapeutics* Clinical Medicine Insights: Oncology vol. 8 p. 71-76 (2014); L. Li et al., *Micro-riboneucleic acids: potential noninvasive biomarkers for hepatocellular carcinoma* Journal of Hepatocellular Carcinoma vol. 1 p. 21-33 (May 2014); P. Prieto, et al., *DKK1 as a serum biomarker for hepatocellular carcinoma* Hepatobiliary Surg. Nutr. Vol. 2 no. 3 p. 127-128 (2013); H. Kim et al., *Development of Biomarkers for Screening Hepatocellular Carcinoma using Global Data Mining and Multiple Reaction Monitoring* PLoS One vol. 8 no. 5 pp. 1-11 (2013); C. Liu et al., *MALDI-TOF MS combined with Magnetic Beads for Detecting Serum Protein Biomarkers and Establishing of Boosting Decision Tree Model for Diagnosis of Hepatocellular Carcinoma* Am. J. Clin. Patho. vol. 134 pp. 235-241 (2010); S. Shang, et al., *Identification of Osteopontin as a Novel Marker for Early Hepatocellullar Carcinoma* Hepatology vol. 55 p. 483-490 (2012).

The development of an improved screening protocol for patients at high risk of developing HCC is an important clinical goal, particularly if it is able to detect early stage HCC. If detected early, HCC can be treated via resection or transplant and 5-year survival rates of 70% may be achieved. See A. Singal et al. paper, supra. However, there are very few approved treatments for unresectable HCC and the prognosis in the later stages of the disease remains very poor, with 5-year survival rates only around 5%. Currently less than 30% of patients are diagnosed early enough to be suitable candidates for resection or transplantation. See A. Singal et al. paper, supra.

This document describes a serum-based test for the detection of HCC in a high risk population using Matrix Assisted Laser Desorption and Ionization-Time of Flight (MALDI-TOF) mass spectrometry, a classifier used in the test, and a method of generation of a classifier for screening high risk patients for early detection of HCC.

SUMMARY

In a first aspect, a method for early detection of HCC in a patient with liver disease (i.e., a high risk population) is disclosed. The method includes a step of performing MALDI-TOF mass spectrometry on a blood-based sample obtained from the patient by subjecting the sample to at least 100,000 laser shots and acquiring mass spectral data. This step can preferably make use of the so-called "deep MALDI" mass spectrometry technique described in U.S. Patent application of H. Röder et al., Ser. No. 13/836,436 filed Mar. 15, 2013, U.S. patent application publication no. US 2013/0320203, assigned to the assignee of this invention, the contents of which are incorporated by reference herein, including automatic raster scanning of a spot on a MALDI plate and summation of spectra from multiple spots. The method includes a step of obtaining integrated intensity values in the mass spectral data of a multitude of pre-determined mass-spectral features, such as 50, 100, 200 or all of the features listed in one of the appendices of this document. The method further includes the step of operating on the mass spectral data with a programmed computer implementing a classifier. The operating step compares the integrated intensity values with feature values of a reference set of class-labeled mass spectral data obtained from a multitude of patients with liver disease with a classification algorithm and generates a class label for the sample, wherein the class label is associated with whether the patient likely has HCC or likely does not have HCC. The moniker for class label is not particularly important and could be of the form Class 1 or Class 2, HCC or No HCC, Likely or Not Likely, or otherwise in some binary classification scheme.

In a preferred embodiment, the classifier is configured as a combination of filtered mini-classifiers using a regularized combination method using the techniques described below and in the pending U.S. patent application of H. Röder et al., Ser. No. 14/486,442 filed Sep. 15, 2014, U.S patent application publication no. 2015/0102216, assigned to the assignee of this invention, the content of which is incorporated by reference herein.

In one embodiment, the obtaining step obtains integrated intensity values of at least 50 features listed in one of the appendices of this document, at least 100 features, or alternatively at least 200 features, such as all of the features listed in one of the appendices.

The classifier assigns a classification label of either HCC or No HCC (or the equivalent) to the patient's sample. Patients classified as HCC are identified as likely to have HCC whereas those patients classified as No HCC are identified as not likely to have HCC. The class label then can be used to guide treatment for the patient, for example if the patient is classified as HCC the patient can immediately receive the appropriate therapy depending on the stage of the cancer.

In another aspect, a classifier is disclosed for early detection of HCC in a patient with liver disease. The classifier includes a memory storing a reference set of mass spectral data obtained from blood-based samples of a multitude of patients with liver disease, including patients with and without HCC, such as feature values of the features listed in one of the appendices of this document. The classifier also includes a programmed computer coded with instructions for implementing a classifier configured as a combination of filtered mini-classifiers with drop-out regularization or some other regularized combination method.

In another aspect, a laboratory testing system for conducting tests on blood-based samples from patients with liver disease to detect HCC is disclosed. The laboratory testing system includes a MALDI-TOF mass spectrometer configured to conduct mass spectrometry on a blood-based sample from a patient by subjecting the sample to at least 100,000 laser shots and acquire resulting mass spectral data, a memory storing a reference set of mass spectral data obtained from blood-based samples of a multitude of other liver disease patients and associated class labels; and a programmed computer coded with instructions to implement a classifier configured as a combination of filtered mini-classifiers with drop-out regularization. The reference set of mass spectral data includes feature values of at least some of the m/z features listed in the appendices to this document, for example all of the features of Example 1 Appendix A, Example 1 Appendix B, or Example 2 Appendix A, Appendix B or Appendix C. The programmed computer is programmed to generate a class label for the sample associated with whether the patient likely has HCC or not.

In still another aspect of the invention, a method for generating a classifier for early detection of HCC in patients with liver disease is disclosed. The method includes the steps of: a) conducting MALDI-TOF mass spectrometry on a set of blood-based samples from a multitude of patients with liver disease, including some patients with HCC and some patients without HCC; b) storing a development set of mass spectrometry data as a result of conducting step a) on the set of blood-based samples, the development set of mass spectrometry data including feature values at a multitude of mass spectral features; c) assigning an initial classification label to each member of the development set of step b); d) separating the development set into training and test sets; e) constructing a multitude of mini-classifiers using one or more of the feature values; f) filtering the performance of the mini-classifiers operating on the training set and retaining only those mini-classifiers that meet a performance threshold; and g) generating a master classifier by combining the filtered mini-classifiers using a regularized combination method. In step h) the performance of the master classifier on the test set is evaluated. The method includes step i) of repeating steps d), e), f), g) and h) for many different realizations of the separation of the development set into training and test sets. In step j) a final classifier is defined from the master classifiers resulting from step g) and the repeated iterations of step i).

In still another aspect, an alternative method for early detection of HCC in patients with liver disease is disclosed. The method includes a step a) of conducting mass spectrometry of a blood-based sample of the patient and acquiring mass spectral data. The method includes step b) of conducting a test on the mass spectral data acquired in step a) by comparing the mass spectral data with a training set of class-labeled mass spectra obtained from blood-based samples from a plurality of non-small cell lung cancer (NSCLC) patients with the aid of a classification algorithm, the class labels assigned to such samples in the training set being Good or the equivalent or Poor or the equivalent, the Good label indicating that such patients in the training set had better outcomes after EGFR-I treatment of the NSCLC as compared to patients having the Poor class label, wherein the test of step b) generates a class label for the blood-based sample and if the class label is Poor or the equivalent, the patient is identified as having HCC. The test b) here in a possible embodiment is the commercial VeriStrat test of the applicant's assignee, described in U.S. Pat. No. 7,736,905, which is incorporated by reference, or an equivalent to such test such as by the use of subsets of deep-MALDI spectra to mimic the 3×2000 shot spectra typically used commercially in the VeriStrat test.

This alternative test makes use of certain insights we have gained over several years regarding the VeriStrat test. In multiple clinical validation studies it has been shown that, for many different types of solid epithelial tumor cancers, patients whose pre-treatment serum/plasma was VeriStrat "Good", have significantly better outcome when treated with EGFR-Is than those patients whose sample results in a VeriStrat "poor" signature. See the published patent application of J. Grigorieva, et al., U.S. 2011/0208433, the content of which is incorporated by reference herein. The Poor mass spectral signature has been identified previously as indicative of a relatively poor prognosis of solid epithelial tumor cancer patients. The Poor signature is believed to be indicative of the presence of cancer. So, in the present testing example, if the patient's serum sample tests Poor under the VeriStrat test, the patient (with liver disease) is indicated as being likely to have HCC and the blood-based sample does not have to be subjected to the HCC/No HCC test described at length in this document.

In a variation, the step a) is performed and test b) is performed but if the class label is Good or the equivalent, the HCC/No HCC test as described in detail herein is performed and the class label is reported.

In a further variation, a test for detection of HCC in high risk populations is as follows: a) conduct an AFP test and if the AFP expression level is>100 ng/ml the patient is classified as HCC. If the AFP expression level is ≤100 ng/ml, the HCC/No HCC test described in this document is conducted. If the HCC/No HCC test result is HCC, the HCC result is reported. If the patient tests as No HCC, the No HCC result is reported.

As a further variation, a three-stage testing process is described. In stage 1, the patient is subject to the VeriStrat test. If the patient tests as VeriStrat Poor, the HCC result is reported. In stage 2, if the Patient tests VeriStrat Good, then conduct the AFP expression level test. If the patient tests with an AFP expression level>100 ng/ml, then report the HCC result. In stage 3, if the VeriStrat Good patient's AFP expression level is≤100 ng/ml, then conduct the HCC/No HCC test of this document and report the result of that test. The results can also be reported as a panel of results including the results from each stage.

BRIEF DESCRIPTION OF THE DRAWINGS

FIG. 1 is a flow-chart showing the classifier development methodology we used to create the classifiers disclosed in this document. The methodology uses mass-spectral data associated with blood-based samples obtained from a multitude of patients with and without HCC.

FIG. 7A is a set of ROC curves for several different classifiers in the development set of Example 1 which had parameters selected to have the best potential performance.

FIG. 7B is an ROC curve for a classifier generated from a validation exercise for Example 1.

DETAILED DESCRIPTION

A method for early detection of HCC in a patient with liver disease (i.e., a member of a high risk population) is disclosed. The method includes a step of performing MALDI-TOF mass spectrometry on a blood-based sample obtained from the patient by subjecting the sample to at least 100,000 laser shots and acquiring mass spectral data. This step can preferably make use of the so-called "deep MALDI" mass spectrometry technique described in U.S. Patent application of H. Röder et al., Ser. No. 13/836,436 filed Mar. 15, 2013, patent application publication no. U.S. 2013/0320203 assigned to the assignee of this invention, the contents of which are incorporated by reference herein, including automatic raster scanning of a spot on a MALDI plate and summation of spectra from multiple spots. The method includes a step of obtaining integrated intensity values in the mass spectral data of a multitude of pre-determined mass-spectral features, such as 50, 100, or all of the features listed in in one of the appendices of this document. The method further includes the step of operating on the mass spectral data with a programmed computer implementing a classifier. The operating step compares the integrated intensity values with feature values of a reference set of class-labeled mass spectral data obtained from a multitude of patients with liver disease with a classification algorithm and generates a class label for the sample, wherein the class label is associated with whether the patient likely has HCC or likely does not have HCC. The moniker for class label is not particularly important and could be of the form Class 1 or Class 2, HCC or No HCC, Likely or Not Likely, or otherwise in some binary classification scheme.

In a preferred embodiment, the classifier is configured as a combination of filtered mini-classifiers using a regularized combination method using the techniques described below and in the pending U.S. patent application of H. Röder et al., Ser. No. 14/486,442 filed Sept. 15, 2014, patent application publication no. U.S. 2015/0102216, assigned to the assignee of this invention, the content of which is incorporated by reference herein.

In the following description of Example 1, we will first describe the patient samples we used to generate a computer-implemented classifier, including spectral acquisition and pre-processing, and our classifier development methodology referred to herein as "combination of mini-classifiers with dropout" or CMC/D and shown in FIG. 1. The description will then discuss the performance of a number of different classifiers we generated, and the various parameters that can be adjusted to find the classifier with optimum performance.

A further example of development of a classifier for early detection of HCC in high risk populations using a second set of samples will be described in Example 2.

Figure 8:
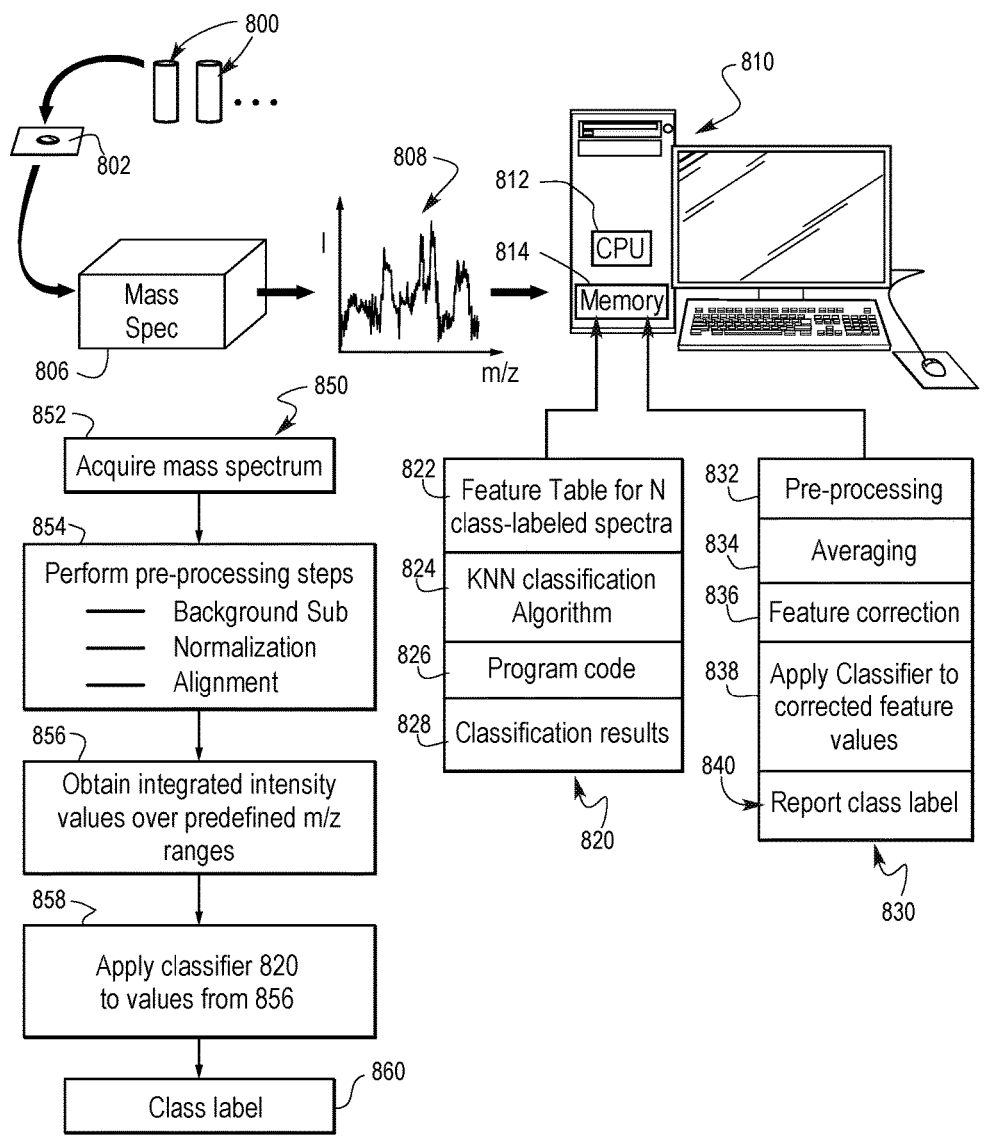
FIG. 8 is a diagram of a laboratory testing system for conducting a test on a blood sample of a patient with liver disease to determine if the patient has HCC.

The description will then turn to a laboratory testing system shown in FIG. 8 in which a test can be performed on blood-based sample of a patient with liver disease to detect the presence of HCC. The laboratory testing center includes a mass spectrometer and a general purpose computer implementing a classifier generated in accordance with the method of FIG. 1 and described in detail below.

The specification will further describe alternative testing methods for early detection of HCC in high risk patients using a different training set and classifier approach, which may be performed separately or in tandem with the HCC/No HCC test described below.

EXAMPLE 1

I. Patient Samples, Spectral Acquisition and Pre-Processing

Patient Samples

Our classifier development process in Example 1 made use of serum samples from 52 patients with hepatocellular carcinoma (HCC), 53 patients with cirrhosis, but no HCC, and 34 samples from patients with no liver disease and no cancer (14 from one set of samples from patients with no cancer and 20 from another set of samples from patients with rheumatoid arthritis). Samples from the patients with liver disease (HCC or no HCC) were taken at time of liver resection or transplant. Four of the patients diagnosed with HCC (all with underlying Hepatitis C) were found to have no viable liver tumor remaining at the time of surgery. The following clinical data was available from the patients with liver disease: origin of underlying liver disease, serum AFP level, bilirubin, INR (International Normalized Ratio, a liver function test), creatinine, and albumin levels, platelet count, grade of encephalopathy, and for most patients, MELD (Model for End-Stage Liver Disease) score. For patients with HCC in addition tumor size, T staging (from TNM, i.e., classification of malignant staging), surgery type (resection or transplant) were available.

Some of the clinical characteristics are summarized by patient group in table 1.

TABLE 1

Baseline clinical and laboratory data for the patients in the HCC and No HCC groups

|  | Cirrhosis | HCC |
|---|---|---|
| MELD Score* |  |  |
| Range | 13-47 | 7-37 |
| Median | 25 | 14 |
| Mean | 27 | 15 |
| AFP‡ * (in ng/ml) |  |  |
| Range | 1-17 | 1-79033 |
| Median | 3 | 9 |
| Mean | 4 | 1880 |
| Serum albumin |  |  |
| Range | 1.9-4.2 | 2.0-5.2 |
| Median | 2.8 | 3.5 |
| Mean | 2.8 | 3.5 |

TABLE 1-continued

Baseline clinical and laboratory data for the patients in the HCC and No HCC groups

|  | Cirrhosis | HCC |
|---|---|---|
| Bilirubin |  |  |
| Range | 1.1-39.0 | 0.4-6.0 |
| Median | 5.8 | 1.2 |
| Mean | 9.1 | 1.8 |
| INR |  |  |
| Range | 1.1-5.1 | 0.9-3.4 |
| Median | 1.8 | 1.3 |
| Mean | 2.0 | 1.4 |
| Creatinine |  |  |
| Range | 0.6-6.6 | 0.5-7.4 |
| Median | 1.9 | 0.9 |
| Mean | 2.3 | 1.3 |
| Platelet Count |  |  |
| Range | 20-486 | 16-400 |
| Median | 78 | 99 |
| Mean | 93 | 124 |
| Evidence of Encephalopathy |  |  |
| None | 1 | 32 |
| 1-2 | 41 | 18 |
| 3-4 | 11 | 2 |
| Origin of Cirrhosis** |  |  |
| Alcohol | 17 | 8 |
| Autoimmune | 1 | 0 |
| Diabetes | 1 | 0 |
| Hepatitis A | 0 | 1 |
| Hepatitis B | 1 | 4 |
| Hepatitis C | 22 | 32 |
| Cryptogenic | 10 | 4 |
| PBC | 7 | 1 |
| Hemochromatosis | 0 | 1 |
| No cirrhosis | 0 | 5 |

* Exact MELD score was only available for 39 of 53 HCC patients. For the remaining 14 patients, MELD score could be determined only within a range. The upper limit of this range did not exceed 25 for any of the 14 patients.
‡AFP expression level was unavailable for one patient with cirrhosis and no HCC
**There may be more than one cause of cirrhosis It is clear that the patients in the HCC group have significantly better liver function compared with the patients in the cirrhosis (no HCC) group.

Table 2 summarizes the tumor measurements for the 52 patients in the HCC group.

TABLE 2

Tumor size data for the patients in the HCC group

|  | Number of patients in HCC group |
|---|---|
| TNM Staging T |  |
| 1 | 29 |
| 2 | 10 |
| 3 | 4 |
| 4 | 2 |
| Unknown | 7 |
| Lesion Size (cm) |  |
| <2 | 7 |
| ≥2 and <3 | 8 |
| ≥3 and <4 | 16 |
| ≥4 and <5 | 6 |
| ≥5 and <6 | 4 |
| ≥6 and <10 | 3 |

TABLE 2-continued

Tumor size data for the patients in the HCC group

| | Number of patients in HCC group |
|---|---|
| ≥10 | 4 |
| unknown | 4 |

Spectral Acquisition

Sample Preparation

Samples were thawed and 3 µl aliquots of each experimental sample and quality control reference serum (a pooled sample obtained from serum from five healthy patients purchased from ProMedDx) spotted onto VeriStrat© cellulose serum cards (Therapak). The cards were allowed to dry for 1 hour at ambient temperature after which the whole serum spot was punched out with a 6 mm skin biopsy punch (Acuderm). Each punch was placed in a centrifugal filter with 0.45 µm nylon membrane (VWR). One hundred µl of HPLC grade water (JT Baker) was added to the centrifugal filter containing the punch. The punches were vortexed gently for 10 minutes then spun down at approximately 10,000 rcf (relative centrifugal force) for 2 minutes. The flow-through was removed and transferred back on to the punch for a second round of extraction. For the second round of extraction, the punches were vortexed gently for 3 minutes then spun down at approximately 10,000 rcf for 2 minutes. Twenty microliters of the filtrate from each sample was then transferred to a 0.5 ml Eppendorf tube for MALDI analysis.

An equal volume of freshly prepared matrix (25 mg of sinapinic acid dissolved in 1 ml of 50% acetonitrile:50% water plus 0.1% TFA) was added to each 20 µl serum extract and the mix vortexed for 30 sec. The first three aliquots (2×2 µl) of sample:matrix mix were discarded into the tube cap. Three aliquots of 2 µl sample:matrix mix were then spotted onto a polished steel MALDI target plate (Bruker Daltonics). The MALDI target was allowed to dry in a biosafety hood before placement in the MALDI-TOF mass spectrometer.

This set of samples (139 experimental samples plus QC sample) was processed for MALDI analysis in four batches. A maximum of 46 experimental samples plus 6 reference samples were contained in batches 1 through 3. The preparations of the reference sample were added to the beginning (2 preparations), middle (2 preparations), and end (2 preparations) of each of these three batches. Batch 4 contained only four experimental samples (with sample IDs 58, 71, 76, and 108) and four preparations of reference sample, two at the beginning of the batch and two at the end of the batch. These four samples had previously been run on one of the three previous batches, but these runs had not generated sufficient raster spectra.

Acquisition of Mass Spectra

MALDI spectra were obtained using a MALDI-TOF mass spectrometer (Ultraflextreme from Bruker Daltonics, Bremen, Germany) equipped with a 2000 Hz SmartBeam laser. Data were acquired with positive ion detection in linear mode with the following settings: accelerating voltage set to 25 kV, extraction voltage set to 23.15 kV, lens voltage set to 7 kV, and the delayed extraction time set to 200 ns. The instrument was externally calibrated using the Bruker Protein Standard Mix consisting of insulin, ubiquitin, cytochrome c, and myoglobin.

Eight hundred shot spectra were collected from 63 predefined positions per MALDI spot (63×800×3 spots per sample), for a total of 151,200 laser shots per sample. While in this example 151,200 shots were done so that 189 (63×3) 800-shot spectra were acquired, we believe that suitable deep spectral information would be obtained as long as good quality spectra from at least 100,000 laser shots can be averaged. It would be possible to obtain spectra averaged from an even greater number of shots, such as 500,000 or 1,000,000 shots, using the techniques of the deep-MALDI patent application cited previously. Fuzzy control for laser power was turned off. No evaluation criteria were used to filter out spectra during acquisition. All filtering and processing of spectra was done post-acquisition.

Spectral Pre-Processing

A. Averaging of Spectra to Produce One Spectrum Per sample

There were 189 (68×3) replicate spectra available for each patient acquired using deep MALDI instrument settings. The spectra were filtered using a ripple filter to remove artificial noise resulting from the digital converter. The background was subtracted for the purpose of finding peaks to be used in alignment. The threshold for peak detection was set to a signal to noise ratio of 3. The raw spectra (no background subtraction) were then aligned using the calibration points listed in table 3. Only spectra with a minimum of 20 peaks detected and having used 5 alignment points were considered for inclusion in the average. As it is not known how many spectra would pass these requirements for each sample, 140 spectra were selected at random to include in the average resulting in an average spectra of 112 K shots (140×800 shots).

TABLE 3

Calibration points used to align the raw spectra prior to averaging

| | m/z |
|---|---|
| 1 | 4153 |
| 2 | 6433 |
| 3 | 6631 |
| 4 | 8206 |
| 5 | 8684 |
| 6 | 9133 |
| 7 | 11527 |
| 8 | 12572 |
| 9 | 23864 |
| 10 | 13763 |
| 11 | 13882 |
| 12 | 14040 |
| 13 | 15127 |
| 14 | 15869 |
| 15 | 17253 |
| 16 | 18630 |
| 17 | 21066 |
| 18 | 28108 |
| 19 | 28316 |

Preprocessing of Average Spectra: First Approach

Initial Preprocessing

The spectra were background subtracted (two windows 80,000/10,000) and normalized using the partial ion current (PIC) windows listed in the table below (table 4). Background subtraction and partial ion current normalization of mass spectra is known and described in U.S. Pat. No. 7,736,904 assigned to the assignee Biodesix, therefore a detailed description is omitted for the sake of brevity.

TABLE 4

PIC Normalization windows used in pre-processing the spectra, left and right m/z boundaries

| Left m/z | Right m/z |
|---|---|
| 3231 | 3301 |
| 7106 | 7178 |
| 9996 | 10317 |
| 15467 | 15771 |
| 16210 | 16399 |

These windows were selected with a method that protects against using windows that are significantly different between groups of interest (HCC vs Cirrhosis), which could lead to a reduction in classification potential, and also against features that are intrinsically unstable. The entire m/z region was divided into 106 bins that varied in size to prevent the bin boundaries from landing within peaks. For each m/z bin, feature values were determined for each sample. The feature values were compared using a Wilcoxon rank-sum test by the group comparisons listed in table 5. If the resulting p value was between 0-0.1, the region was excluded from normalization. If the CV of the feature values (all samples) was greater than 1.0, the region was excluded. Only the 5 windows above met the requirement for all 3 group comparisons. None of these contain high intensity features.

TABLE 5

Group comparisons used to test normalization window dependency on clinical group

| Group | Comparison |
|---|---|
| 1 | HCC versus Cirrhosis and No Cancer |
| 2 | HCC versus Cirrhosis |
| 3 | HCC and Cirrhosis vs No Cancer |

Figure 2A:
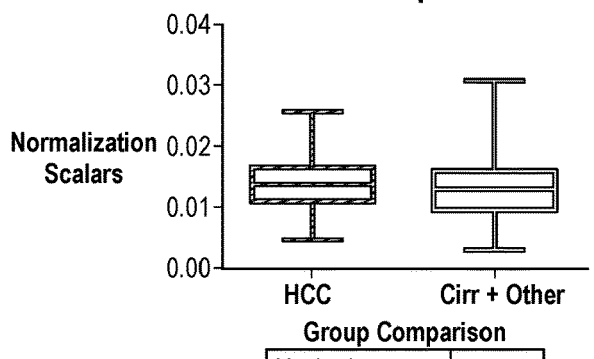
FIGS. 2A-2C are box and whisker plots showing the results of a normalization step in the preprocessing of mass spectral data to construct the classifiers of Example 1 of this disclosure.
Figure 2B:
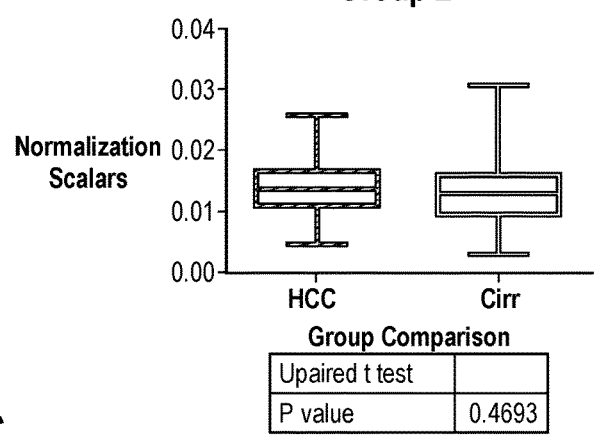
Figure 2C:
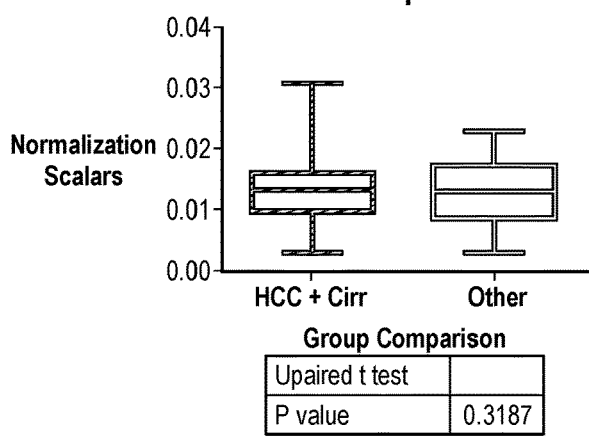

The remaining bins were used as the PIC normalization windows and for each sample a normalization scalar was calculated. A final comparison of groups was performed to ensure that the groups and the normalization parameters used are not correlated. The box and whisker plots of FIG. 2 demonstrate that the groups have similar distributions of normalization scalars.

The spectra were then calibrated using the calibration points listed in table 6 to remove slight differences in alignment.

TABLE 6

Calibration points used to align the Deep MALDI average spectra

| | m/z |
|---|---|
| 1 | 4154 |
| 2 | 4361 |
| 3 | 4711 |
| 4 | 6432 |
| 5 | 6631 |
| 6 | 9420 |
| 7 | 12862 |
| 8 | 13762 |
| 9 | 14039 |
| 10 | 14088 |
| 11 | 14145 |
| 12 | 15128 |
| 13 | 15869 |
| 14 | 17383 |
| 15 | 18272 |
| 16 | 28108 |
| 17 | 28316 |

Feature Definitions

Feature definitions were selected manually by viewing a subset from each group (HCC, Cirrhosis, other) of the spectral averages simultaneously. Left and right peak boundaries were assigned by assessing the compilation of spectra for each feature. This process ensures the features are adequately captured for any individual spectrum. A total of 307 features were identified. The feature definitions were applied to each spectrum to create a feature table of feature values. Following additional analysis for batch correction (see below), it was found that the high m/z features (>22,000 Da) were not sufficiently reproducible and they were removed from the feature list used for CMC/D classifier generation. This left 300 features available for use in CMC/D classifier generation. These features are listed in Example 1 Appendix A.

Analysis of Reference Samples by Batch

Six preparations of reference sample (quality control sample) were prepared along with the experimental samples in each batch (except for batch 4 which had only 4 preparations). Two of these preparations were plated at the beginning (replicates. 1 and 2), two at the end (replicates. 5 and 6), and two preparations were plated amid the experimental samples (replicates 3 and 4). The purpose of the reference sample replicates was to provide a common sample in each batch that could be used to correct the batches for expected day to day fluctuations in spectral acquisition. The reference samples were preprocessed as described above.

A set of feature definitions, specific to the reference sample and selected for their stability, was applied to the spectra. These feature definitions can be found in Appendix C Table C1 of our prior provisional application, incorporated by reference herein. The resulting feature table was used only in the analysis of the reference samples. The reference sample spectra were analyzed to find two replicates that were most similar from the beginning and end of each batch. We compared each possible combination of replicates (1 and 5, 1 and 6, 2 and 5, 2 and 6) using the function:

$$A=\min(\text{abs}(1-\text{ftrval1}/\text{ftrval2}), \text{abs}(1-\text{ftrval2}/\text{ftrval1}))$$

where ftrval1 (ftrval2) is the value of a feature for the first (second) replicate of the replicate pair. This quantity A gives a measure of how similar the replicates of the pair are. A select set of 20 features (table 7), known to be stable, were used to determine the most similar combinations of reference spectrum ("SerumP2") replicates taken from the beginning and end of the batches. This process prevents the use of an outlier replicate spectrum in the batch correction procedure.

TABLE 7

The 20 most stable features considering beginning and end of batch reference spectra replicates m/z 3952
4338

TABLE 7-continued

The 20 most stable features considering beginning and end of batch reference spectra replicates m/z

| m/z |
|---|
| 6192 |
| 6834 |
| 7612 |
| 8203 |
| 8432 |
| 8765 |
| 9133 |
| 9568 |
| 9638 |
| 9710 |
| 9932 |
| 10347 |
| 10838 |
| 11529 |
| 11727 |
| 11943 |
| 12564 |
| 12856 |

Using a cutoff of 0.2 for A, the combination with the most passing features was deemed the most similar and used for batch correction purposes. In the case of a tie, the leftmost of the combinations ordered as 1_5, 1_6, 2_5, 2_6 is used. For example, for batch 1, combination 1_5 and 2_5 had all 20 features achieve the 0.2 cutoff. The 1_5 combination was selected because it sits furthest to the left in the prescribed order. If a combination was not found where 15 of the 20 features passed the cutoff for a batch, then the batch would be considered a failure and would need to be re-run. In this project, all 4 batches passed using these criteria. For each batch, the combination of most similar reference spectra replicates was found and an average set of feature values was created from the two replicates by averaging the feature values of the two replicates for each feature. These average feature values were used as the reference for each batch for the purpose of batch correction.

Batch Correction

Batch 1 was used as the baseline batch to correct all other batches. The reference sample was used to find the correction coefficients for each of the batches 2-4 by the following procedure.

Within each batch j ($2 \leq j \leq 14$), the ratio $$\hat{r}_i^j = \frac{A_i^j}{A_i^1}$$

and the average amplitude $\overline{A}_i^j = \frac{1}{2}(A_i^j + A_i^1)$ are defined for each $i^{th}$ feature centered at $(m/z)_i$, where $A_i^j$ is the average reference spectra amplitude of feature i in the batch being corrected and $A_i^1$ is the reference spectra amplitude of feature i in batch 1 (the reference standard). It is assumed that the ratio of amplitudes between two batches follows the dependence $$r(\overline{A},(m/z))=(a_0+a_1 ln(\overline{A}))+(b_0+b_1 ln(\overline{A}))(m/z)+c_0(m/z)^2.$$

On a batch to batch basis, a continuous fit is constructed by minimizing the sum of the square residuals, $\Delta^j = \Sigma_i (\hat{r}_i^j - r^j(a_0, a_1, b_0, b_1, c_0))^2$, and using the experimental data of the reference sample. The features used to create this fit are only a subset (described in Appendix C, table C.1 of our prior provisional application Ser. No. 62/086,805) of the whole available set, from which features known to be have poor reproducibility were removed. Steps were taken to not include outlier points in order to avoid bias in the parameter estimates. The values of the coefficients $a_0$, $a_1$, $b_0$, $b_1$ and $c_0$, obtained for the different batches are listed in Appendix C (table C.2) of our prior provisional application Ser. No. 62/086,805. The projection in the $\hat{r}_i^j$ versus $(m/z)_i$ plane of the points used to construct the fit for each batch of reference spectra, together with the surface defined by the fit itself, is shown in figure C.1 of Appendix C of our prior provisional application.

Once the final fit, $r^j(\overline{A}, (m/z))$, is determined for each batch, the next step is to correct, for all the samples, all the features (with amplitude A at (m/z)) according to $$A_{corr} = \frac{A}{r^j(A, (m/z))}.$$

After this correction, the corrected $(A_i^j, (m/z)_i, \hat{r}_i^j)$ feature values calculated for reference spectra lie around the horizontal line defined by r=1, as shown in figure C.2 of Appendix C of our prior provisional application.

Preprocessing of Averaged Spectra: Second Approach (Reduced Feature Spaces)

The idea of this approach was to use feature definitions from 25 k shot spectra applied to the full 112 k spectra to generate a set of features with less variability.

Initial Preprocessing

The original deep MALDI spectra were background subtracted and normalized using the same modified partial current normalization methods as in the first approach using only regions that did not differentiate between the clinical groups as specified by univariate p-values (see Initial preprocessing in Preprocessing of averaged spectra: First approach: Initial Preprocessing).

Feature definitions were generated by visual inspection of the 25 k shot spectra yielding 164 features (see Example 1 Appendix B). With these features separate batch corrections were performed using a slightly modified batch correction procedure (listed below) for the 112 k shot spectra only (Appendix C, table D.2 of our prior provisional application.)

Batch Correction (Modified)

For this approach a modified batch correction procedure was used. This followed the following steps:

1. Generate feature tables by batch using the 25 k feature definitions
2. For the 4 reference sample runs at the beginning and ends of each batch form the four possible pair combinations for each feature using min (abs (1−ftrval$^j$/ftrval$^k$), abs (1−ftrval$^k$/ftrval$^j$)) as an evaluation criterion (as defined in the batch correction process for the first approach), for all features values, where j and k indicate the reference spectra, i.e. we have four combinations for j and k: 1-5, 1-6, 2-5, 2-6.
3. For each of these j,k pairs calculate the number of features where the evaluation criterion exceeds 0.2.
4. Select that pair with the minimal number of features exceeding the evaluation criterion. (Appendix D, table D.2 of our prior provisional application).
5. Average the feature values for the selected pair and use it as the reference for its batch
6. Carry out the batch correction process described above such generated reference spectra.

The resulting batch correction fit values are listed in Appendix D table D.3 of our prior provisional application.

Normalization

The batch corrected feature table was re-normalized using the procedure outlined for the first pre-processing approach. In short, from the batch corrected feature table features were identified that did not separate the three clinical groups with a univariate p-value larger than 0.05. These features were used in the PIC tool to sub-select a set of features for further normalization. The following features were used for this normalization step: 3818, 3954, 4052, 5105, 12293.

Feature Condensation

The resulting batch corrected and re-normalized feature table was further analyzed to combine those features which were significantly correlated as determined by a correlation coefficient greater than 0.85. This resulting feature table contained 75 features. A combined feature containing doubly charged hemoglobin features was then removed. The correlation plots and the list of combined features are shown in Appendix D, figure D.2 and table D.4, respectively of our prior provisional application, the contents of which are incorporated by reference herein.

As explained below, we used the feature tables resulting from the mass spectral data subject to preprocessing as explained above (integrated intensity vales for each of the features listed in Example 1 Appendix A or Example 1 Appendix B) in generation of a classifier. This set of mass spectral data is referred to as the development sample set 100 in FIG. 1. The method of generating the classifier is described in the following section.

CMC/D Classifier Development and Generation of Classifier For Early Detection of HCC in High Risk Patients The new classifier development process using the method of combination of mini-classifiers (mCs) with dropout regularization (CMC/D) is shown schematically in FIG. 1. The steps in this process are explained in detail below. The methodology, its various advantages, and several examples of its use, are explained in great detail in U.S. patent application Ser. No. 14/486,442 filed Sep. 15, 2014, U.S. patent application publication 2015/0102216, the content of which is incorporated by reference. A brief explanation of the methodology will be provided here first, and then illustrated in detail in conjunction with FIG. 1 for the generation of the HCC classifier.

In contrast to standard applications of machine learning focusing on developing classifiers when large training data sets are available, the big data challenge, in bio-life-sciences the problem setting is different. Here we have the problem that the number (n) of available samples, arising typically from clinical studies, is often limited, and the number of attributes (p) per sample usually exceeds the number of samples. Rather than obtaining information from many instances, in these deep data problems one attempts to gain information from a deep description of individual instances. The present methods take advantage of this insight, and is particularly useful, as here, in problems where p>>n.

The method includes a first step a) of obtaining measurement data for classification from a multitude of samples, i.e., measurement data reflecting some physical property or characteristic of the samples. The data for each of the samples consists of a multitude of feature values, and a class label. In this example, the data takes the form of mass spectrometry data, in the form of feature values (integrated peak intensity values at a multitude of m/z ranges or peaks) as well as a label indicating some attribute of the sample (e.g., patient had HCC, patient did not have HCC). In this example, the class labels were assigned by a human operator to each of the samples after investigation of the clinical data associated with the sample. Preferably in this step the measurement data is obtained from at least 100,000 laser shots applied to the sample in MALDI-TOF mass spectrometry as described previously in this detailed description; i.e., presents a deep description of the individual blood-based samples used to generate the classifier.

The method continues with a step b) of constructing a multitude of individual mini-classifiers using sets of feature values from the samples up to a pre-selected feature set sizes (s=integer 1 . . . n). For example a multiple of individual mini- or atomic classifiers could be constructed using a single feature (s=1), or a pair of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measurement data values (p) in the data set, and where p is in the hundreds, thousands or even tens of thousands, s will typically be 1, or 2 or possibly 3, depending on the computing resources available. The mini-classifiers execute a supervised learning classification algorithm, such as k-nearest neighbors, in which the values for a feature or pairs of features of a sample instance are compared to the values of the same feature or features in a training set and the nearest neighbors (e.g., k=5) in an s-dimensional feature space are identified and by majority vote a class label is assigned to the sample instance for each mini-classifier. In practice, there may be thousands of such mini-classifiers depending on the number of features which are used for classification.

The method continues with a filtering step c), namely testing the performance, for example the accuracy, of each of the individual mini-classifiers to correctly classify at least some of the multitude of samples, or measuring the individual mini-classifier performance by some other metric (e.g. the difference between the Hazard Ratios (HRs) obtained between groups defined by the classifications of the individual mini-classifier for the training set samples) and retaining only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used to create mini-classifiers, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible KNN classifiers using feature sets up to a pre-selected size (parameter s). This gives us many "mini-classifiers": e.g. if we start with 100 features for each sample (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step c) we only use those "mini-classifiers" that pass predefined criteria. These criteria are chosen dependent on the particular problem: If one has a two-class classification problem, one would select only those mini-classifiers whose classification accuracy exceeds a pre-defined threshold, i.e., are predictive to some reasonable degree. Even with this filtering of "mini-classifiers" we end up with many thousands of "mini-classifier" candidates with performance spanning the whole range from borderline to decent to excellent performance.

The method continues with step d) of generating a master classifier by combining the filtered mini-classifiers using a regularized combination method. In one embodiment, this regularized combination method takes the form of repeatedly conducting a logistic training of the filtered set of mini-classifiers to the class labels of the samples. This is done by randomly selecting a small fraction of the filtered mini-classifiers as a result of carrying out an extreme dropout from the filtered set of mini-classifiers (a technique referred to as drop-out regularization herein), and conducting logistical training on such selected mini-classifiers. While similar in spirit to standard classifier combination methods (see e.g. S. Tulyakov et al, *Review of Classifier Combination Methods*, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. In this case, where we have many mini-classifiers and a small training set we use extreme dropout, where in excess of 99% of filtered mini-classifiers are dropped out in each iteration.

In more detail, the result of each mini-classifier is one of two values, either "Class 1" or equivalently "HCC", or "Class 2" or equivalently "No HCC" in this example. We can then combine the results of the mini-classifiers by defining the probability of obtaining a "Class 1" label via standard logistic regression (see e.g. the logistic regression entry in Wikipedia)

$$P(\text{``Class 1''}|\text{feature for a spectrum}) = \frac{\exp\left(\sum_{\text{mini classifiers}} w_{mc} I(mc(\text{feature values}))\right)}{\text{Normalization}} \quad \text{Eq. (1)}$$

where I(mc(feature values))=1, if the mini-classifier mc applied to the feature values of a sample returns "Class 1", and 0 if the mini-classifier returns "Class 2". The weights for each of the mini-classifiers ($w_{mc}$) are unknown and need to be determined from a regression fit of the above formula for all samples in the training set using +1 for the left hand side of the formula for the Class 1-labeled samples in the training set, and 0 for the Class 2-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at once, we use only a few of the mini-classifiers for a regression, but repeat this process many times in generating the master classifier. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the CMC/D master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

Other methods for performing the regularized combination method in step (d) that could be used include:

Logistic regression with a penalty function like ridge regression (based on Tikhonov regularization, Tikhonov, Andrey Nikolayevich (1943). " Об устойчивости обратных задач " [On the stability of inverse problems]. Doklady Akademii Nauk SSSR 39 (5): 195-198.)

The Lasso method (Tibshirani, R. (1996). Regression shrinkage and selection via the lasso. J. Royal. Statist. Soc B., Vol. 58, No. 1, pages 267-288).

Neural networks regularized by drop-out (Nitish Shrivastava, "Improving Neural Networks with Dropout", Master's Thesis, Graduate Department of Computer Science, University of Toronto; available from the computer science department website of the University of Toronto, see prior provisional for link.

General regularized neural networks (Girosi F. et al, Neural computation, (7), 219 (1995). The above-cited publications are incorporated by reference herein. Our approach of using drop-out regularization has shown promise in avoiding over-fitting, and increasing the likelihood of generating generalizable tests, i.e. tests that can be validated in independent sample sets.

In step e) of the method, the development set of samples is randomly separated into a test set and a training set, and the steps b)-d) are repeated in the programmed computer for different realizations of the separation of the set of samples into test and training sets, thereby generating a plurality of master classifiers, one for each realization of the separation of the set of samples into training and test sets.

The method continues with step f) of defining a final classifier from one or a combination of more than one of the plurality of master classifiers. In the present example, the final classifier is defined using a cutoff in the probability obtained from the logistic combination averaged over all master classifiers (test/training splits). To classify samples used in the development set, this is adjusted so that the cutoff is applied to the probability obtained from averaging the outputs of the logistic combination over the master classifier for which a given sample is not in the training set.

With reference now to FIG. 1, we have a development sample set 100, in this case the mass spectrometry data of blood-based samples the 105 patients with liver disease. In addition to the mass spectral features defined as explained above, alphafetoprotein (AFP) expression level in ng/ml was also used as a feature in the CMC/D process, i.e. the measured value of AFP for each sample was used to augment the mass spectral feature space and AFP was treated in the same way as the mass spectral features to create mini-classifiers. In addition, in some developments of a classifier in according to FIG. 1 we excluded from the development sample set 100 those patients with high serum AFP levels, whereas in other classifier generation exercises we included those patients. This aspect will be discussed in further detail below.

Definition of Initial Class Labels (Step 102)

The classifiers were trained by assigning a class label of HCC (the 48 patients from the set of 52 patients with diagnosed HCC who still had signs of viable tumor at time of sample collection) shown as 104 in FIG. 1 or No HCC (53 patients with cirrhosis but no HCC), shown as 106 in FIG. 1. The 34 samples from patients without any liver disease were not used directly in training the classifiers.

Selection of Training and Test Set (Step 108)

Once the initial definition of the class labels has been established at step 102, the development set, or subset thereof to be used to build the classifier, is split into training and test sets at step 108. The test set 110 is used to test classifier performance at step 134 (see below), the training set 112 is used to train a classifier and operations 120, 126 and 130 are performed on the training set 112.

Creation and Filtering of Mini-Classifiers (mCs, Step 120 and 126)

In step 120, many k-nearest neighbor (kNN) mini-classifiers (mCs) that use the training set as their reference set are constructed using subsets of features from the 300 mass spectral features (and possibly also AFP level) already identified. For many of the investigations all possible single features and pairs of features were examined (s=2); however, when fewer features were used, triplets or all possible sets of four or five features (s=3, 4 or 5) were also considered. For the 300 mass spectral features, just traversing all single features and pairs of features amounts to considering 45,150 possible mCs. The parameters used to traverse the space of mCs for this project are values of K of 5, 7 or 11. For the mC traversal parameters we started with single features (level 1), using all features of Example 1 Appendix A (or some subset of features); we used all feature combinations at each level or "depth" of the mC (1, 2, 3, 4 or 5). As shown in FIG. 1 at 124, the feature table for the samples in the development set includes integrated intensity values at selected features (shown in shading) and as shown at 122 the features are compared, either single, pairs of features etc. in a multi-dimensional feature space using kNN and at step 128 only those comparisons that result in "good" classifications (indicated by the + sign) are retained.

In particular, in step 126 to target a final classifier that has certain performance characteristics, the mCs constructed at step 120 are filtered. Each mC is applied to its training set and possibly other sets (not including samples from the test set) and performance metrics are calculated from the resulting classifications of the training set. Only mCs that satisfy thresholds on these performance metrics pass filtering to be used further in the process. The mCs that fail filtering are discarded. For this project only accuracy filtering was used, i.e. the classifier was applied to a set of samples (such as the training set or a subset of the patients without liver disease) and the accuracy of the resulting classification had to lie within a preset range for the mC to pass filtering. The filtering options used in this project are listed in tables 8, 9 and 10 set forth below.

This particular problem and patient cohort presents considerable challenges as, in addition to the two groups being different due to presence or absence of cancer, the groups also differ in terms of liver function, which is clearly visible in the mass spectra. Hence, while it is easy to make a classifier that can separate the "HCC" group from the "No HCC" group with good accuracy based on relative level of liver function, this classifier would not detect presence or absence of cancer and so fail in the high risk screening setting. To avoid creating a classifier based on this very strong confounding factor an extra filter was used to eliminate mCs based on relative levels of liver function. The set of 34 patients with no liver disease was split into two subsets. One half was used as a filter on the mCs to ensure that, in addition to adequate performance on the classifier training set, the mC classified a large proportion of these patients with healthy livers as cancer-free. The remaining half of the set of patients with no liver disease was used as a test set to ensure that any final test also classifies patients with healthy livers as cancer-free. This method eliminates the possibility of producing a classifier based solely on liver function, rather than presence or absence of cancer.

Generate Final Classifier From a Combination of Mini-Classifiers Using Logistic Regression With Dropout (Steps 130, 132)

Once the filtering of the mCs is complete, the mCs are combined in one master classifier (MC) at step 130 by logistic regression training using the training set labels. To help avoid overfitting the regression is regularized using extreme drop out. Most of the CMC/D approaches in this study randomly selected 10 of the mCs for inclusion in each logistic regression iteration. The number of dropout iterations was selected based on the typical number of mCs passing filtering for each approach to ensure that each mC was likely to be included within the drop out process multiple times.

Training/Test Splits (Loop 135) and Analysis of Master Classifier Performance (Step 134)

The split of the class groups into training and test sets is performed many times (loop 135 and repeating step 108) using a stratified randomization. Each training/test split produces a MC at step 130 which can be applied to the split test set 110 to assess performance at step 134. The use of multiple training/test splits avoids selection of a single, particularly advantageous or difficult, training set for classifier creation and avoids bias in performance assessment from testing on a test set that could be especially easy or difficult to classify.

Final Classifier Definition (Step 144)

The output of the logistic regression (132) that defines each MC is a probability of being in one of the two training classes. These MC outputs over the many training and test set splits can be combined at step 144 to make one resultant or "final" classifier in several possible ways.

Applying a cutoff (e.g. 0.5) to these probabilities, one can generate a binary classification label for a sample from each MC. These labels can then be combined in a majority vote to obtain one binary classification for a sample. When analyzing the performance of the classifier in the development set, it is helpful to use a modified majority vote for samples which are used in training the classifier. For samples which are used in the training set of some of the training/test set split realizations, the modified majority vote (MMV) is defined as the majority vote of the MC labels over the MCs which do not have the sample in the training set. For samples which are never used in any training set, the modified majority vote and majority vote are identical. The MC probabilities can be averaged over MCs to yield one average probability for a sample. When working with the development set, this approach can also be adjusted to average over MCs for which a given sample is not included in the training set, in an analogous way to the MMV procedure. These average probabilities can be used as the output of a classifier or a threshold can be applied to convert them into a binary classification.

In addition, the standard deviation of the MC probabilities can be calculated for a sample. This can potentially provide additional information as to the certainty or uncertainty that can be ascribed to the average probability of a sample. While not being useful for providing a direct classification of a sample, these outputs can be used when multiple classifiers are stacked.

The present CMC/D method works best when the two classes (HCC, No HCC) in the training set 112 are of approximately equal sizes. To achieve this it may be necessary to sample the classes defined at step 102 at different rates. In addition, performance has been seen to deteriorate quickly when the size of the kNN reference sets drops very low. When there are small numbers in one of the training classes, it can be advantageous to include most of the samples in the kNN reference set in each realization, leaving only a few samples as a test set. This process still works well providing the number of training/test set split realizations is scaled up to allow for adequate statistics for all samples when they are in the test sets of the realizations.

Many implementations of the CMC/D process for FIG. 1 were investigated, varying in the population or subset of samples in the development set used for the test/training splits, the filtering used in the CMC/D process, and the feature space explored. Each such implementation, with varying parameters, is referred to as "approach" in Tables 8, 9 and 10.

Some of these approaches involved a refined or condensed feature selection within the sets of mass spectral features of Example 1 Appendix A. While there are, in general, many methods that could be used to reduce the sets of mass spectral features to a small, more relevant set, the bias with respect to liver function between our classes (HCC, No HCC) again complicated matters. Many features in the whole sets will show clear ability to differentiate the classes based solely on liver function and these may outnumber the features which have ability to differentiate the classes based on presence or absence of cancer. To try to ensure that we maintain features really differentiating the classes based on cancer/no cancer rather than liver function, a subset of samples from the development set was constructed with very close balance by MELD score. This was necessarily a small subset of the available samples (11 patients with HCC and 11 patients with underlying liver disease and no HCC). Feature selection was based on the ability of the features to discriminate between HCC and No HCC within this 22 patient subset. The p-value of the t-test across these groups was used as the criterion to select the top features.

A summary of some of the approaches tried during new classifier development using the standard CMC/D workflow and the first set of defined features is presented in tables 8 and 9. Table 8 contains approaches that used all 48 HCC patients for training and table 9 contains approaches that first excluded some HCC patients with high AFP expression levels (as determined from examination of t-SNE plots, see Appendix E of our prior provisional application, incorporated by reference herein) and trained on the remaining HCC patients. All approaches used all No HCC patients with underlying liver disease in training. Note that there was also filtering of the mini-classifiers based on how accurately the mini-classifiers classified the mass spectra of a group of healthy patients using the same feature definitions. (The correct classification assignment for healthy patients is a No HCC classification. So accuracy is 1 would have all healthy patient samples classified as No HCC and an accuracy of 0 would have all healthy patients classified as HCC.) In the Feature Used column, "no AFP" means that the feature associated with AFP was excluded from the feature set, "plus AFP" means that the feature set included the AFP feature.

TABLE 8

Approaches to CMC/D used for this project training on all HCC and all No HCC patients. If not otherwise stated, K = 11 was used.

| Approach # | Features Used | Depth (# features in kNN mCs) | mC Filtering Options |
|---|---|---|---|
| 1 | 300, no AFP | 2 | 0.65 < training set accuracy < 0.95; 0.75 < healthy pt accuracy < 1.0 |
| 2 | 300, plus AFP | 2 | 0.65 < training set accuracy < 0.95; 0.75 < healthy pt accuracy < 1.0 |
| 3 | 149 selected by t-test, plus AFP | 2 | 0.65 < training set accuracy < 0.95; 0.75 < healthy pt accuracy < 1.0 |
| 4 | 149 selected by t-test, plus AFP | 3 | 0.65 < training set accuracy < 0.95; 0.75 < healthy pt accuracy <1.0 |
| 5 | 100 selected by t-test, plus AFP | 2 | 0.65 < training set accuracy < 0.95; 0.60 < healthy pt accuracy < 1.0 (run for both k = 11 and k = 7) |
| 6 | 100 selected by t-test, no AFP | 3 | 0.65 < training set accuracy < 0.95; 0.50 < healthy pt accuracy < 1.0 |
| 7 | 100 selected by t-test, plus AFP | 3 | 0.65 < training set accuracy < 0.95; 0.60 < healthy pt accuracy < 1.0 AND 0.65 < training set accuracy < 0.95; 0.50 < healthy pt accuracy < 1.0 AND 0.65 < training set accuracy < 0.95; 0.40 < healthy pt accuracy < 1.0 |

TABLE 8-continued

Approaches to CMC/D used for this project training on all HCC and all No HCC patients. If not otherwise stated, K = 11 was used.

| Approach # | Features Used | Depth (# features in kNN mCs) | mC Filtering Options |
|---|---|---|---|
| 8 | 100 selected by t-test, plus AFP | 4 | 0.65 < training set accuracy < 0.95; 0.5 < healthy pt accuracy < 1.0 |
| 9 | 50 selected by 2 t-test, no AFP | 2 | 0.60 < training set accuracy < 0.95; 0.65 < healthy pt accuracy < 1.0 |
| 10 | 50 selected by t-test, with AFP | 2 | 0.65 < training set accuracy < 0.95; 0.70 < healthy pt accuracy < 1.0 |
| 11 | 50 selected by 3 t-test, with AFP | 3 | 0.65 < training set accuracy < 0.95; 0.70 < healthy pt accuracy < 1.0 |
| 12 | 50 selected by t-test, no AFP | 3 | 0.65 < training set accuracy < 0.95; 0.50 < healthy pt accuracy < 1.0 |

TABLE 9

Approaches using a subset of HCC patients excluding patients with highest AFP levels (11 patients for 100 and 149 mass spectral features who had AFP levels >340 ng/ml; 15 patients for 50 mass spectral features who had AFP levels >68 ng/ml). If not otherwise stated, K = 11 was used.

| Approach # | Features Used | Depth (# features in kNN mCs) | mC Filtering Options |
|---|---|---|---|
| 13 | 99 selected by t-test, plus AFP | 2 | 0.65 < training set accuracy <0.95; 0.5 < healthy pt accuracy < 1.0 |
| 14 | 99 selected by t-test, plus AFP | 3 | 0.65 < training set accuracy < 0.95; healthy pt accuracy filtering between 0.4 < healthy pt accuracy < 1.0 and 0.6 < healthy pt accuracy < 1.0 K = 5, 7, 11 |
| 15 | 99 selected by t-test, no AFP | 3 | 0.65 < training set accuracy < 0.95; 0.45 < healthy pt accuracy < 1.0 AND 0.65 < training set accuracy < 0.95; 0.5 < healthy pt accuracy < 1.0 |
| 16 | 99 selected by t-test, plus AFP | 4 | 0.65 < training set accuracy < 0.95; 0.5 < healthy pt accuracy < 1.0 |
| 17 | 149 selected by t-test, plus AFP | 3 | 0.65 < training set accuracy < 0.95; 0.45 < healthy pt accuracy < 1.0 AND 0.65 < training set accuracy < 0.95; 0.5 < healthy pt accuracy < 1.0 |
| 18 | 149 selected by t-test, no AFP | 3 | 0.65 < training set accuracy < 0.95; 0.45 < healthy pt accuracy < 1.0 AND 0.65 < training set accuracy < 0.95; 0.5 < healthy pt accuracy < 1.0 |
| 19 | 50 selected by t-test, plus AFP | 3 | 0.65 < training set accuracy < 0.95; healthy pt accuracy filtering between 0.45 < healthy pt accuracy < 1.0 and 0.55 < healthy pt accuracy < 1.0 |
| 20 | 50 selected by t-test, plus AFP | 4 | 0.65 < training set accuracy < 0.95; 0.55 < healthy pt accuracy < 1.0 |

Approaches using the second, alternate set of defined features (listed in Example 1 Appendix B) are summarized in table 10. These were all trained on a subset of the HCC patients, as defined by an AFP cutoff determined by inspection of the respective t-SNE plots.

TABLE 10

Approaches using a subset of HCC patients excluding patients with highest AFP levels and using the second set of feature definitions (Example 1 Appendix B). If not otherwise stated, K = 11 was used.

| Approach # | Features Used | Depth (# features in kNN mCs) | Filtering Options |
|---|---|---|---|
| 21 | 164 plus AFP | 2 | 0.65 < training set accuracy < 0.95; healthy pt accuracy filtering between 0.5 < healthy pt accuracy < 1.0 and 0.6 < healthy pt accuracy < 1.0 |
| 22 | 74 (condensed), plus AFP | 3 | 0.7 < training set accuracy < 0.9; 0.6 < healthy pt accuracy < 1.0 |
| 23 | 50, selected by t-test from condensed plus AFP | 3 | 0.7 < training set accuracy < 0.9; healthy pt accuracy filtering between 0.5 < healthy pt accuracy < 1.0 and 0.6 < healthy pt accuracy < 1.0 K = 5, 7, 11 |
| 24 | 50, selected by t-test from condensed plus AFP | 4 | 0.7 < training set accuracy < 0.9; 0.5 < healthy pt accuracy < 1.0 K = 7 |

Development Set 100 CMC/D Classifier Results

Figure 3:
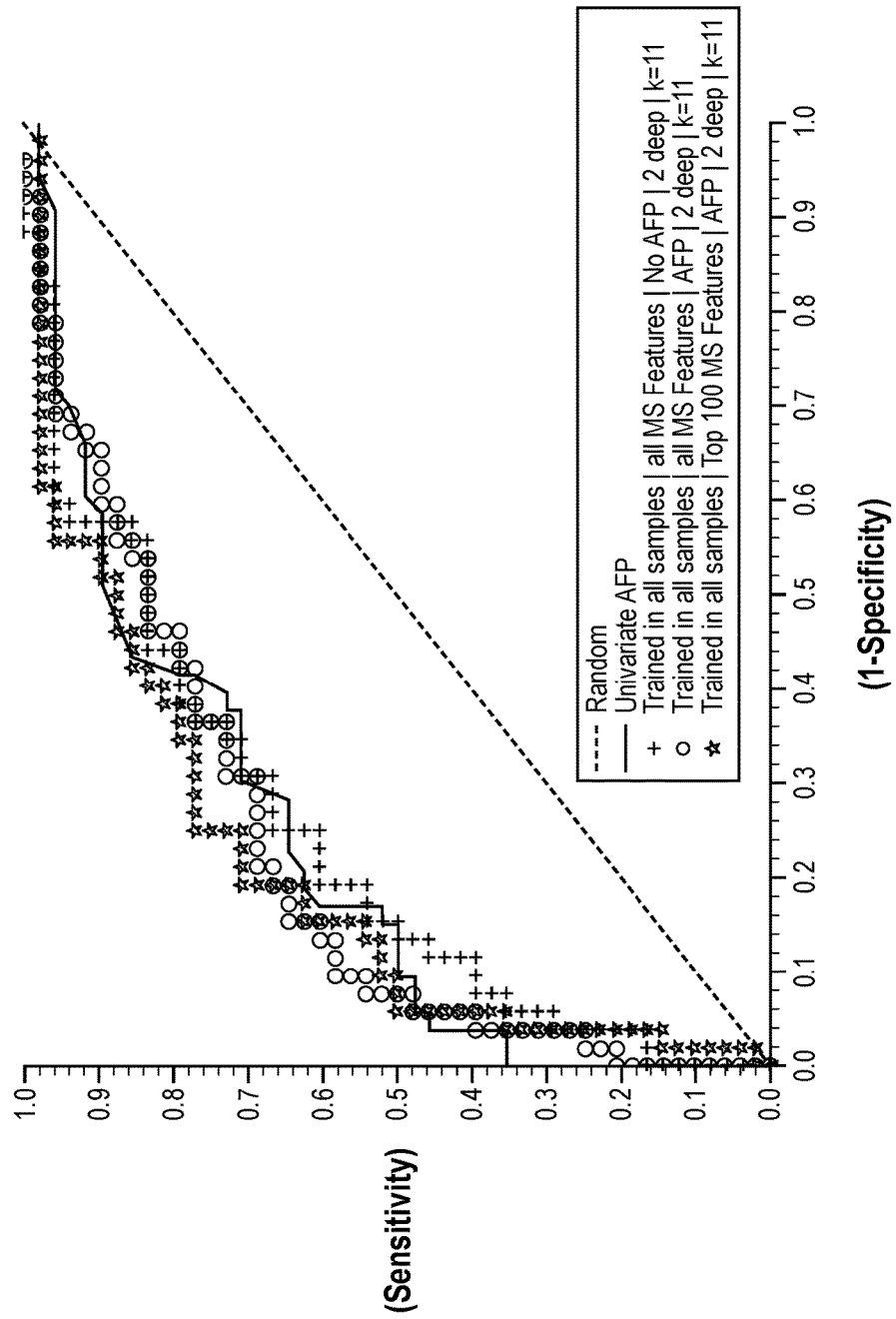
FIG. 3 is a Receiver Operating Curve (ROC) showing the classifier performance for some preliminary attempts at classifier development of Example 1, showing plots for different selection of features for classification, and different training sets.

The performance of each classifier approach was assessed using receiver operator characteristic (ROC) curves, which allow the visualization of the sensitivity and specificity obtained for each approach for different values of the cutoff applied to the average probabilities obtained for each sample. When samples were used in training, the average probability was calculated across the realizations (MCs) where the sample was in the test set (out of bag estimate). For samples never used in training, the probability was simply averaged over all realizations (MCs). Sometimes a sample was used in training in all realizations. When this occurred, no reliable classification could be obtained for the sample and it was not used in evaluating classifier performance. From previous experience working on this problem, it was known that confounding by liver function was a major danger, so we also checked the classification of a test set of patients with no liver disease to see that these classified predominantly as No HCC. FIG. 3 shows the ROC results from some early attempts at classifier development where all samples were used in training the classifier, i.e. the whole set of 48 HCC samples and 53 No HCC samples were split into test and training sets. For reference, the ROC curve obtained for these samples using a simple cutoff in AFP was also plotted (the solid black line).

The CMC/D approaches shown in FIG. 3 used only pairs of features and single features (2 deep) and K=11 to form the KNN mCs. Using all mass spectral features without AFP (crosses) gave classifiers with similar performance to AFP alone. Expanding the feature space to include the AFP feature (circles) improved performance, boosting the sensitivity achievable at high specificities. Using only the top 100 features (including the AFP feature) as determined by lowest p-values of a t-test between a set of HCC and no HCC samples matched exactly by MELD score (stars in FIG. 3), maintained the high specificity performance and increased the specificity achievable at high sensitivity. Hence, de-selection of features with little or no information for the classification process and inclusion of the AFP feature were determined to be useful elements in achieving good classification performance.

Figure 4:
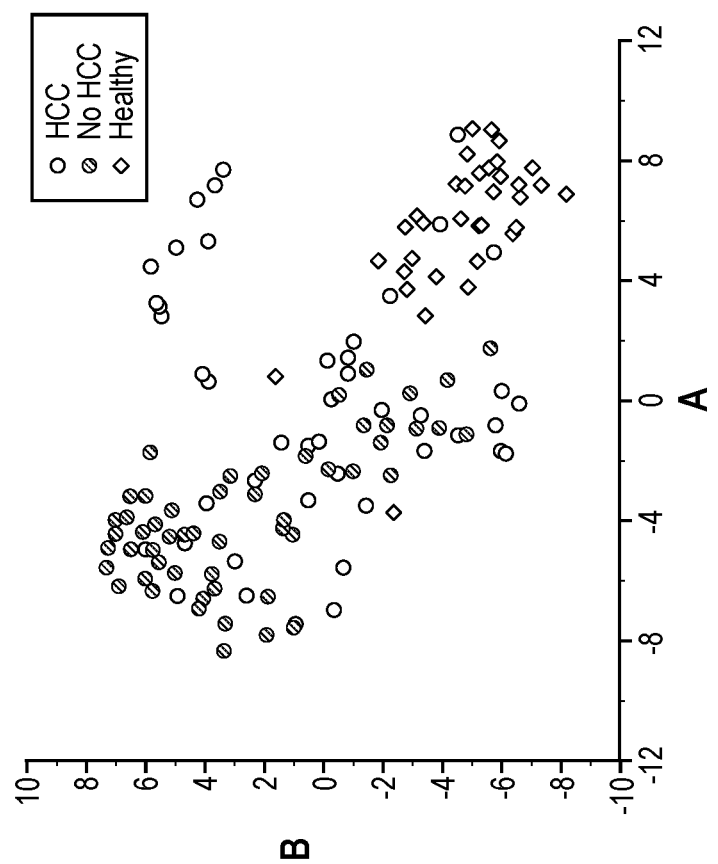
FIG. 4 is a t-Distributed Stochastic Neighbor Embedding (tSNE) plot for the top 100 features selected on the matched set comparison of HCC v. no HCC patients in Example 1. This includes 99 mass spectral features and AFP expression level. In the plots, A and B are the two coordinates of the t-SNE low dimensional space.

To investigate how performance could be improved further, the feature space was visualized using the t-Distributed Stochastic Neighbor Embedding (tSNE) method. t-SNE is a tool that allows the visualization of high-dimensional data in a 2D or 3D-map, capturing much of the local structure of the data while also revealing global structure (e.g., the presence of clusters at several scales). The method converts high-dimensional Euclidean distances between data points into Gaussian similarities. In the low-dimensional (2D or 3D) space, the same process is applied using a Student-t distribution instead of a Gaussian distribution to compute the similarity between pairs of points. Then, iteratively, the method seeks a low-dimensional representation of the original data set that minimizes the mismatch between the similarities computed in the high- and low-dimensional spaces. In this way, a 2D or a 3D point map is constructed that allows the visualization and identification of structure in a given dataset. FIG. 4 is a tSNE plot of the feature space of the top 100 features (99 spectral features and AFP feature) as determined by t-test p-values. A and B are the two coordinates of the t-SNE low dimensional space.

The FIG. 4 plot illustrates two interesting aspects of the problem. First, although the features used were determined based on a comparison between two groups with precisely matched MELD score and hence closely matched liver function, the separation of groups by liver function is still evident. The samples from patients with no liver impairment cluster at the bottom right of the plot, while the patients with liver disease but no HCC, whom we know to have worst liver function as a group, tend to occur towards the center and top left of the plot. The samples from the patients with HCC, who as a group have better liver function than the no HCC patients, but worse liver function than the healthy patients, tend to occur in the center of the plot. Hence, there is still a great deal of liver function dependence in the behavior of the features by class, even after de-selection designed to minimize selecting features primarily on liver function.

The second interesting characteristic of the FIG. 4 plot is the grouping of HCC patients that can be seen in the top right. Investigation of the available clinical data revealed that these patients were those with very high AFP level (greater than around 65 ng/ml). As these samples all fall into the HCC class and are disconnected in feature space from the remaining samples, an approach to classifier development was attempted which removed these easy to classify samples from training and concentrated instead of training the classifier on the harder task of correctly classifying the other HCC samples and the no HCC samples.

Figure 5:
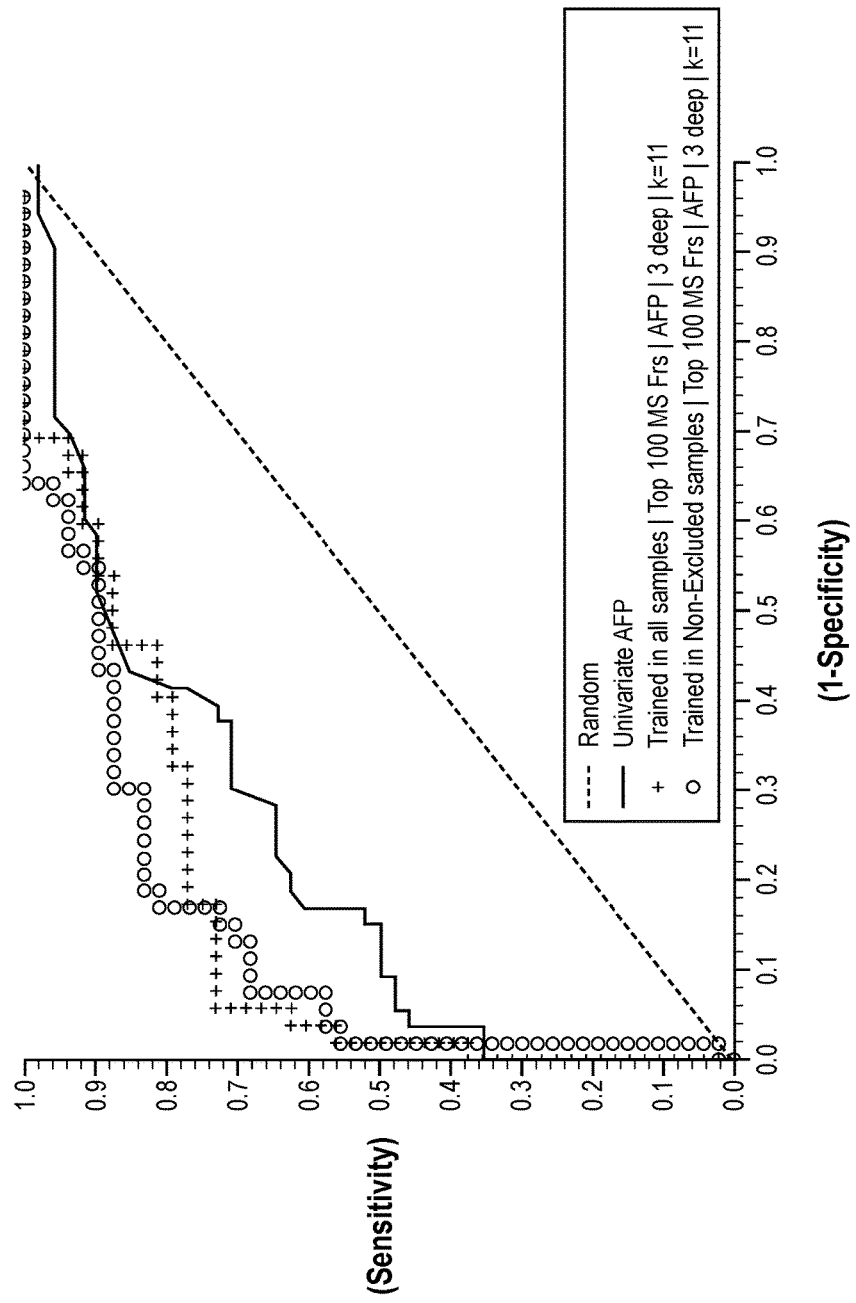
FIG. 5 illustrates ROC curves showing the performance of classifiers in the development set (Example 1) using the same traversal of feature space and same K=11, with one curve showing performance with training on all samples in the development set, and another curve showing performance with training on only samples without very high AFP levels.

FIG. 5 shows ROC curves for a second group of classifiers, showing the marked improvement in performance obtained using the same set of features, the same depth of exploration of feature space (3 deep, using triplets and pairs of features and single features) and the same K=11, when training is carried out excluding from the development set the samples with very high AFP and using only the remaining, non-excluded samples.

The classification approach using AFP, the top 100 features and going deeper into feature space, including triplets of features to form mCs as well as pairs of features and single features, provides good performance, achieving 83%/81% or 81%/83% sensitivity/specificity. It also maintains respectable sensitivity (68%) at specificities above 90%.

Figure 6:
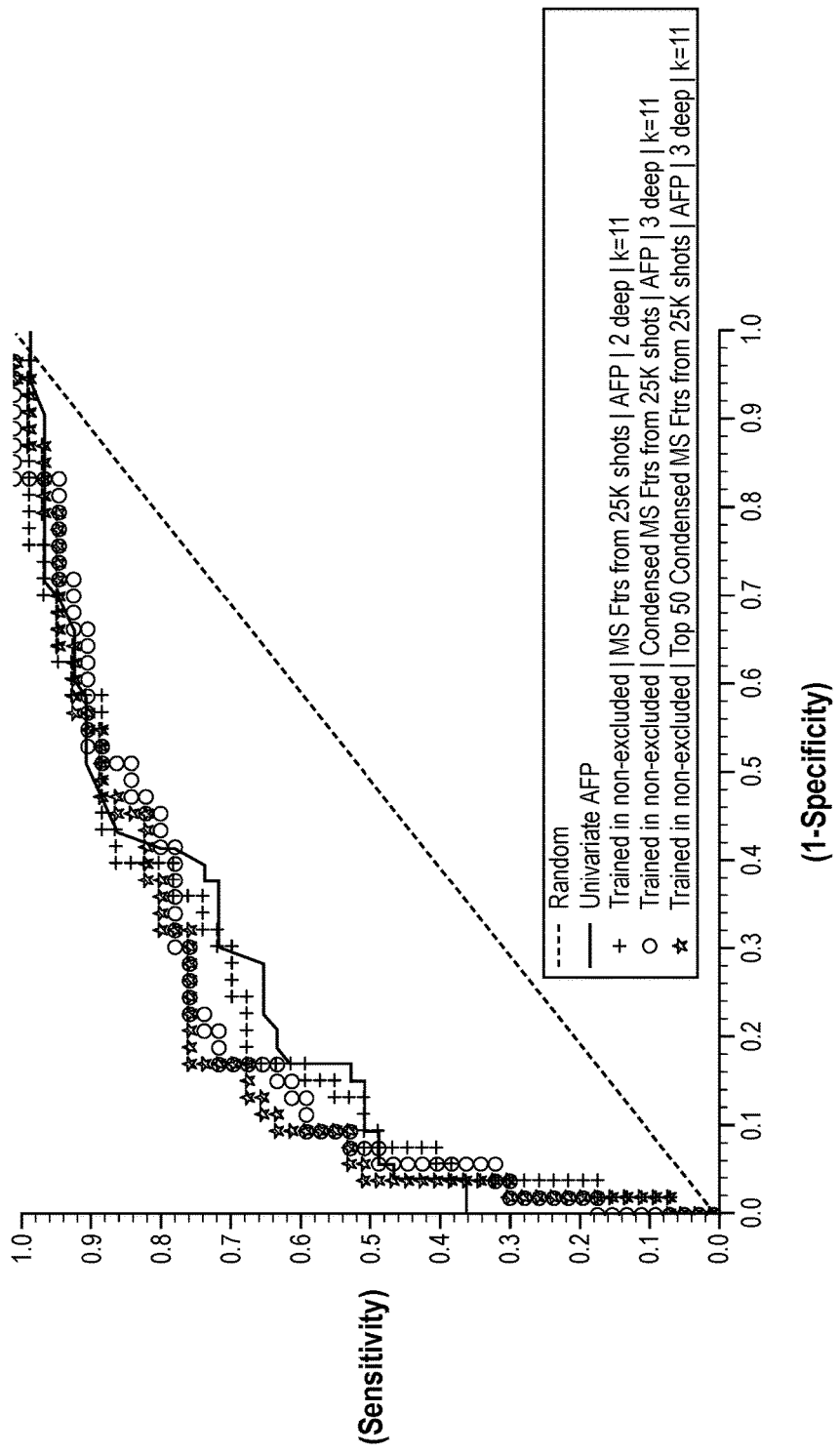
FIG. 6 shows ROC curves for classifier approaches we attempted using a condensed set of features defined from 25,000 shot mass spectra for Example 1. Whereas the classifier performance curves (development set, Example 1) shown in FIG. 5 were based on 100,000+ shot spectra and higher numbers of features, in FIG. 6 we used an alternative feature definition method, designed to avoid adding noisy, high variability features to the feature space used in classification.

Using the alternative feature definition method, designed to avoid adding noisy, high variability features to the feature space used in classification (Preprocessing of averaged spectra (second approach)), some similar patterns in performance were observed. The ROC plots for some classifier approaches using the features defined from 25 k shot mass spectra are shown in FIG. 6. Performance improved when the full set of features was condensed by combining correlated features (circles) and then further improved when the top 50 features were selected from the 74 condensed features by using only the 50 features with smallest p-value in the comparison of HCC v. no HCC groups within the set of patients matched precisely by MELD score (stars).

Exploring these different approaches to classifier generation and testing various choices for the K used for the KNN mCs and the different ranges used for mC filtering, the classification approaches shown in FIG. 7A were selected as having the best potential performance.

One approach using the first feature definition method and a second using the second feature definition method were selected for optimal simultaneous high sensitivity and specificity. The approach with best performance without use of the AFP feature (stars) is also shown. The final candidate is an approach that achieves good sensitivity at very high specificity (triangles).

For validation purposes, cutoffs for average probability need to be chosen to define one classifier from each classification approach. Table 11 summarizes the cutoff chosen for each of the four classification approaches shown in FIG. 7A, along with the associated sensitivity and specificity. The performance of these classifiers are shown on FIG. 7A as the solid points on each plot.

We will now explain how and why the sensitivity/specificity as demonstrated in the ROC curves could be adjusted. Clinical considerations should drive the choice of cutoffs for the clinical question being considered. Each ROC plot is generated from one CMC/D run or classifier generation exercise using FIG. 1. Instead of using the majority vote (or modified majority vote), we calculate for each sample, the average probability produced from the logistic combination across all the realizations where that sample is in the test set (instead of the majority classification with 0.5 cutoff on the probability across all the realizations where that sample is in the test set, as we do for MMV). So, for each sample we get a number between 0 and 1, which corresponds to the average probability that the sample is assigned to one of the two classifications (whichever one we call Class 1). We can set a cutoff of 'p' (for any $0<=p<=1$), and put all samples that have an average probability below p in Class 2 and all samples that have an average probability above or equal to p in Class 1. As we increase p from 0 up to 1, we get sets of possible classifications for all the samples and the accuracy of these classifications is what we plot (in terms of the sensitivity and specificity of each set of classifications for each p) as the ROC curve. So, the ROC curve really shows results for a large number of possible individual classifiers, which are parameterized by the cutoff, p. If we pick p=0.5, we usually get classifications, and resulting sensitivity and specificity, close to the MMV approach. However, we could pick any value of p, depending on where our ROC curve gives us the most clinically useful test (sometimes one needs a very high sensitivity and sometimes a high specificity is better).

For the classifiers defined in table 11, the classifications of each sample were obtained. These are listed in Appendix E of our prior provisional application, which is incorporated by reference. For each classifier the performance by origin of cirrhosis, TNM T stage, and tumor size is summarized in Tables 12, 13, and 14, respectively. It was found from classifying samples from the test set of patient without liver disease or HCC that patients with healthy liver are predominantly classified as No HCC.

TABLE 11

Cutoffs and performance of the selected classifiers

| Description | Cutoff | Sensitivity | Specificity |
|---|---|---|---|
| 100 features, 3 deep, K = 5, AFP, non-excluded samples | 0.51004 | 85% | 81% |
| 50 cond. ftrs, 4 deep, K = 7, AFP, non-excluded samples | 0.387 | 79% | 81% |
| 100 ftrs, 3 deep, K = 11, no AFP, non-excluded samples | 0.462 | 77% | 79% |
| 100 ftrs, 3 deep, K = 11, all samples | 0.31168 | 73% | 95% |

TABLE 12

Performance of the selected classifiers by origin of cirrhosis for all patients with liver disease (There may be more than one origin of cirrhosis.)

| Origin of Cirrhosis | 100 ftrs, 3 deep, K = 5, AFP, non-excluded samples | | 100 ftrs, 3 deep, K = 11, no AFP, non-excluded samples | | 50 cond. ftrs, 4 deep, K = 7, AFP, non-excluded samples | | 100 ftrs, 3 deep, K = 11, all samples | |
|---|---|---|---|---|---|---|---|---|
| | No HCC | HCC | No HCC | HCC | No HCC | HCC | No HCC | HCC |
| Alcohol | 13/17 (76%) | 6/8 (75%) | 14/17 (82%) | 6/8 (75%) | 12/17 (71%) | 6/8 (75%) | 14/16 (88%) | 6/8 (75%) |
| Autoimmune | 1/1 (100%) | 0 | 1/1 (100%) | 0 | 1/1 (100%) | 0 | 1/1 (100%) | 0 |
| Diabetes | 1/1 (100%) | 0 | 1/1 (100%) | 0 | 1/1 (100%) | 0 | 1/1 (100%) | 0 |
| Hepatitis A | 0 | 0 | 0 | 0 | 0 | 0/1 (0%) | 0 | 0/1 (0%) |
| Hepatitis B | 1/1 (100%) | 3/4 (75%) | 1/1 (100%) | 2/4 (50%) | 1/1 (100%) | 4/4 (100%) | 1/1 (100%) | 3/4 (75%) |
| Hepatitis C | 18/22 (82%) | 26/28 (93%) | 19/22 (86%) | 23/28 (82%) | 17/22 (77%) | 24/28 (86%) | 21/21 (100%) | 20/28 (71%) |
| Cryptogenic | 8/10 (80%) | 4/4 (100%) | 6/10 (60%) | 4/4 (100%) | 9/10 (90%) | 4/4 (100%) | 9/10 (90%) | 4/4 (100%) |
| PBC | 6/7 (86%) | 1/1 (100%) | 6/7 (86%) | 1/1 (100%) | 7/7 (100%) | 1/1 (100%) | 7/7 (100%) | 1/1 (100%) |
| Hemo-chromatosis | 0 | 0/1 (0%) | 0 | 0/1 (0%) | 0 | 0/1 (0%) | 0 | 0/1 (0%) |
| No cirrhosis | 0 | 4/5 (80%) | 0 | 3/5 (60%) | 0 | 3/5 (60%) | 0 | 4/5 (80%) |

TABLE 13

Performance of the selected classifiers within the HCC group by TNM T stage

| TNM Staging T | 100 ftrs, 3 deep, K = 5, AFP, non-excluded samples | 100 ftrs, 3 deep, K = 11, no AFP, non-excluded samples | 50 cond. ftrs, 4 deep, K = 7, AFP, non-excluded samples | 100 ftrs, 3 deep, K = 11, all samples |
|---|---|---|---|---|
| 1 | 24/29 (83%) | 20/29 (69%) | 21/29 (72%) | 21/29 (72%) |
| 2 | 6/8 (75%) | 6/8 (75%) | 7/9 (78%) | 4/9 (44%) |
| 3 | 4/4 (100%) | 4/4 (100%) | 4/4 (100%) | 4/4 (100%) |
| 4 | 2/2 (100%) | 2/2 (100%) | 2/2 (100%) | 2/2 (100%) |
| Unknown | 4/4 (100%) | 4/4 (100%) | 4/4 (100%) | 4/4 (100%) |

TABLE 14

Performance of the selected classifiers within the HCC group by tumor size

| Lesion Size | 100 ftrs, 3 deep, K = 5, AFP, non-excluded samples | 100 ftrs, 3 deep, K = 11, no AFP, non-excluded samples | 50 cond. ftrs, 4 deep, K = 7, AFP, non-excluded samples | 100 ftrs, 3 deep, K = 11, all samples |
|---|---|---|---|---|
| <2 | 4/5 (80%) | 4/5 (80%) | 3/6 (50%) | 4/6 (75%) |
| ≥2 and <3 | 4/7 (57%) | 2/7 (29%) | 4/7 (57%) | 3/7 (43%) |
| ≥3 and <4 | 15/16 (94%) | 14/16 (88%) | 14/16 (88%) | 13/16 (88%) |
| ≥4 and <5 | 6/6 (100%) | 5/6 (83%) | 5/6 (83%) | 6/6 (100%) |
| ≥5 and <6 | 4/4 (100%) | 4/4 (100%) | 4/4 (100%) | 4/4 (100%) |
| ≥6 and <10 | 2/3 (67%) | 2/3 (67%) | 2/3 (67%) | 2/3 (67%) |
| ≥10 | 4/4 (100%) | 4/4 (100%) | 4/4 (100%) | 4/4 (100%) |
| unknown | 1/2 (50%) | 1/2 (50%) | 2/2 (100%) | 1/2 (50%) |

Validation of Classifier of Example 1 on Second Sample Set

An exercise was conducted to see if the classifiers generated as explained above in Example 1 could be validated on a completely independent set of blood-based samples from patients in a high risk population for development of HCC.

The validation sample set cohort consisted of blood-based samples from 193 patients with liver disease from Greece, 110 with HCC and 83 patients with underlying liver disease and no detected HCC. The main cause of liver disease in both HCC and no HCC patients was hepatitis B. Alphafetoprotein (AFP) expression levels were provided for 180 patients (103 with HCC and 77 with no HCC) and only data for these 180 patients is presented in this section. Some of the clinical characteristics of the cohort are summarized by patient group in table 15.

TABLE 15

Baseline clinical and laboratory data for the patients in the HCC and No HCC groups

| | HCC | No HCC |
|---|---|---|
| MELD Score* | | |
| Range | 6-26 | NA |
| Median | 10 | NA |
| Mean | 11.2 | NA |
| AFP (in ng/ml) | | |
| Range | 1-74756 | 0.7-9.9 |
| Median | 99 | 3.0 |
| Mean | 3657 | 3.3 |
| BCLC category | | |
| A (suitable for surgery or transplant) | 3 | NA |
| B (suitable for locoregional treatment) | 14 | NA |
| C (candidate for sorafenib therapy) | 72 | NA |
| D (palliative care) | 14 | NA |
| Child-Pugh Category | | |
| A | 70 | 68 |
| B | 26 | 7 |
| C | 7 | 2 |
| Gender | | |
| Male | 85 | 55 |
| Female | 18 | 22 |

TABLE 15-continued

Baseline clinical and laboratory data for the patients
in the HCC and No HCC groups

|  | HCC | No HCC |
|---|---|---|
| Performance Status | | |
| 0 | 19 | 54 |
| 1 | 45 | 18 |
| 2 | 25 | 5 |
| 3 | 8 | 0 |
| 4 | 6 | 0 |
| Origin of Cirrhosis** | | |
| Alcohol | 15 | 4 |
| Fatty Liver Disease | 5 | 5 |
| Hepatitis B | 67 | 59 |
| Hepatitis C | 10 | 7 |
| Cryptogenic | 11 | 2 |
| Age | | |
| Range | 44-84 | 28-80 |
| Median | 69 | 54 |
| Mean | 69 | 54 |

*Exact MELD score was only available for 102 of 103 HCC patients.
** There may be more than one cause of cirrhosis Note that the no HCC patients in this population have relatively good liver function (88% Child-Pugh A). The HCC group has quite advanced disease (70% BCLC category C, i.e. eligible for sorafenib treatment, as too advanced for transplant, resection, or TACE therapy). This can also be seen from the data on tumor size for the HCC patients, shown in table 16.

TABLE 16

Tumor size data for the patients in the HCC group

| Lesion Size (cm) | Number of patients in HCC group |
|---|---|
| ≥2 and <3 | 1 |
| ≥3 and <4 | 4 |
| ≥4 and <5 | 9 |
| ≥5 and <6 | 9 |
| ≥6 and <10 | 20 |
| ≥10 | 28 |
| unknown | 32 |

Sample preparation and spectral acquisition were carried out exactly as described for the development set above. Samples were run in four batches, each batch with two reference sample preparations at the beginning of the batch and two reference sample preparations at the end of the batch.

One hundred forty raster spectra were selected at random and processed to produce one 112 K shot average spectrum per sample, as described in detail above.

Deep MALDI averages were batch corrected to account for possible variations in m/Z sensitivity of the mass spectrometer following the procedure described above for batch correction.

The classifier described above in table 11, last entry ("100 ftrs, 3 deep, K=11, all samples") with probability cutoff locked at 0.31168 was run on the batch corrected feature table. Samples that tested VeriStrat Poor (25 of 180 samples), under the VeriStrat test of the assignee Biodesix, U.S. Pat. No. 7,736,905, see the discussion of Alternative Testing Method later in this document, were assigned to the HCC class. All other samples were assigned the classification resulting from the classifier. (Note that in the development set only one sample classified as VeriStrat Poor and all classifiers tested assigned this sample to the HCC class.) One hundred and thirteen samples were assigned the HCC classification and 67 the No HCC classification.

Validation Set Results

The sensitivity of the classifier was 89% (92/103) and the specificity was 73% (56/77) in the overall population with available AFP expression levels. Within the subgroup of patients with current or previous hepatitis B infection, sensitivity and specificity were 91% and 78%, respectively. Within the subgroup of patients with the best liver function, Child-Pugh A, performance was 90% sensitivity and 75% specificity.

The breakdown of performance by various patient characteristics is shown in table 17.

TABLE 17

Classification accuracy by clinical characteristic
subgroups. (number correct in subgroup/total number in subgroup)

|  |  | HCC | No HCC |
|---|---|---|---|
| Cause of liver disease | HBV | 58/64 (91%) | 46/59 (78%) |
|  | HBV + HCV | 1/1 (100%) | 0/0 |
|  | HBV + Alcohol | 2/2 (100%) | 0/0 |
|  | HCV | 6/7 (86%) | 3/7 (43%) |
|  | HCV + Alcohol | 2/2 (100%) | 0/0 |
|  | Alcohol | 10/11 (91%) | 2/4 (50%) |
|  | Fatty Liver Disease | 4/5 (80%) | 4/5 (80%) |
|  | Cryptogenic | 9/11 (82%) | 1/2 (50%) |
| Child-Pugh Category | A | 63/70 (90%) | 51/68 (75%) |
|  | B | 23/26 (88%) | 4/7 (57%) |
|  | C | 6/7 (86%) | 1/2 (50%) |
| Gender | Male | 77/85 (91%) | 39/55 (71%) |
|  | Female | 15/18 (83%) | 17/22 (77%) |
| Performance Status | 0 | 16/19 (84%) | 40/54 (74%) |
|  | 1 | 39/45 (87%) | 12/18 (67%) |
|  | 2 | 25/25 (100%) | 4/5 (80%) |
|  | 3 | 8/8 (100%) | 0/0 |
|  | 4 | 4/6 (67%) | 0/0 |

Within the HCC group, performance was also assessed by tumor size and BCLC classification category (table 18).

TABLE 18

Classification accuracy for HCC samples
by lesion size and BCLC category (number
correct in subgroup/total number in subgroup)

|  |  | Accuracy |
|---|---|---|
| Lesion Size (cm) | <2 | 0/0 |
|  | >=2 and <3 | 1/1 (100%) |
|  | >=3 and <4 | 3/4 (75%) |
|  | >=4 and <5 | 8/9 (89%) |
|  | >=5 and <6 | 7/9 (78%) |
|  | >=6 and <10 | 18/20 (90%) |
|  | >=10 | 26/28 (93%) |
|  | Unknown | 29/32 (91%) |
| BCLC | A | 2/3 (67%) |
|  | B | 11/14 (79%) |
|  | C | 67/72 (93%) |
|  | D | 12/14 (86%) |

In addition to the assessment of the classifier with cutoff selected during the development process, the performance of the set of classifiers produced from varying the cutoff was investigated and compared with the ROC curve obtained for univariate AFP classification on the validation set. The results are shown in FIG. 7B. In particular, FIG. 7B plots ROC curves for the classifier allowing for variation in the probability cutoff. The ROC curve for univariate AFP expression level with variable cutoff on the validation set is also shown for comparison. The solid symbol shows the probability cutoff selected during development.

Example 1

Conclusions

The data in these tables show that the classifiers have good performance across patients with underlying liver disease independent of the origin of liver disease. The classifiers correctly identified as HCC all patients with larger tumors (greater than 10 cm or T=3 or 4). Of greater importance, however, is that the sensitivity in detection of the smallest tumors (<2 cm or T1) was still very high (over or around 70% for all 4 classifiers). Hence, small tumors can be detected at a time when curative treatments or effective interventions are still possible.

We have shown that it is possible using blood-based samples and deep MALDI mass spectrometry to develop classifiers able to detect HCC in patients with underlying liver disease. The candidate classifiers demonstrated test set performance of clinical relevance in screening of patients at high risk for developing HCC. Classifier performance seemed insensitive to cause of underlying liver disease within the range of etiologies studied, which spanned the most common causes of liver disease in the United States population. The high performance extended to detection of small lesions of less than 2 cm or TNM stage T1. This is important as for any HCC screening program to impact patient survival, the cancer be identified as early as possible, when effective therapies can be offered to newly diagnosed patients.

The HCC early detection classifier validated well in a completely independent validation cohort and demonstrated the ability to generalize well from the development set population, where the dominant causes of underlying liver disease were hepatitis C infection, to the independent validation set, where the dominant cause of liver disease was hepatitis B. The performance of the classifier at this sensitivity was vastly better than that which could be obtained from AFP alone on the validation set.

The sensitivity was 89% in the validation set, compared with 73% in the development set. It should be noted that patients in the development set all had relatively early stage HCC, amenable to treatment by transplant or resection (BCLC category A), whereas the majority of patients in the validation set had more advanced HCC. This factor likely accounts for the increase in sensitivity. It should be noted that currently less than 30% of HCC patients are diagnosed early enough for surgical intervention, so sensitivity in a typical early detection setting could be expected to be greater than that in the development set and should lie between the validation set result and the development set result.

The specificity in the validation set was 73%, compared with 95% in the development set. The patients without HCC in the validation set had considerably better liver function than those with no HCC in the development set, who were all receiving liver transplants due to underlying liver disease. In addition, the validation cohort HCC patients also had better liver function, according to MELD scores (median 10 in validation HCC subgroup vs median 14 in development HCC subgroup vs median 25 in development no HCC subgroup). Investigation of errors in classification assignment within the no HCC group revealed that they predominantly occurred in patients with better liver function and AFP in the higher part of the normal range. This could be expected given the lack of training samples from patients with no HCC and good liver function.

While the validation study has shown that the sensitivity of the classifier is likely to be very acceptable for clinical application, the specificity seems to be a little low. However, the development set was dominated by no HCC patients with extremely poor liver function. We were very optimistic that classifier redevelopment combining samples from the original development set with some of the samples from this validation cohort would allow a considerable improvement in test specificity at these already good levels of sensitivity. Redevelopment would also allow test development incorporating AFP measurements carried out using the specific AFP test that can be most easily used as a component of a commercial HCC early detection test. Hence, we conducted the redevelopment of the HCC No HCC mass spectrometry classifier and test and the results are explained in the Example 2 which now follows.

Example 2

In this Example we describe a redevelopment of a test to identify patients with hepatocellular carcinoma (HCC) within the high risk population of patients with underlying liver disease. 158 samples were available from patients with HCC (110 from Thrace, Greece and 48 from Texas, USA), 135 samples from patients with no HCC but underlying liver disease (83 from Greece and 52 from Texas). An additional four Texas samples were available from patients diagnosed with HCC who had received chemoembolization and were found to have no viable tumor left at time of surgery (time of sample collection). Two additional Greek samples (Biodesix ID 146 and 195) were available for whom HCC/No HCC status and other clinical information are currently unavailable and one additional Texas sample (ID 35) was available for which AFP was not available (inadvertently not run). In addition 32 in-house samples were available from patients with no liver disease or HCC. All samples were serum samples.

The clinical characteristics of the 293 patients with full clinical data and well-defined HCC status are shown in table 19. (As all HCC patients from the Texas cohort were undergoing liver resection or transplant, they are all assumed to be in BCLC category A.)

TABLE 19

Clinical characteristics of the combination of the two patient cohorts

| | HCC (N = 158) | No HCC (N = 135) |
|---|---|---|
| MELD score* | | |
| Range | 6-37 | — |
| Median | 11 | — |
| Mean | 12 | — |
| # samples where NA | 15 | — |
| BCLC Category | | |
| A | 51 | — |
| B | 15 | — |
| C | 73 | — |
| D | 19 | — |
| AFP (in ng/ml) | | |
| Range | <0.8->100000 | <0.8-115 |
| Median | 23 | 1.9 |
| Mean | 4412 | 3.6 |

TABLE 19-continued

Clinical characteristics of the combination of the two patient cohorts

|  | HCC (N = 158) | No HCC (N = 135) |
|---|---|---|
| Origin of Cirrhosis* | | |
| Alcohol | 24 | 24 |
| Fatty Liver Disease | 5 | 5 |
| Hepatitis A | 1 | 0 |
| Hepatitis B | 76 | 60 |
| Hepatitis C | 38 | 28 |
| Cryptogenic | 17 | 13 |
| None | 5 | 0 |
| PBC | 1 | 7 |
| Autoimmune | 0 | 3 |
| TNM T status | | |
| 1 | 28 | — |
| 2 | 9 | — |
| 3 | 4 | — |
| 4 | 2 | — |
| NA | 115 | — |
| Lesion Size (cm) | | |
| Range | 1-28 | — |
| Median | 5.6 | — |
| Mean | 7.4 | — |
| # pts with lesions between | | |
| <2 cm | 6 | — |
| ≥2 and <3 cm | 8 | — |
| ≥3 and <4 cm | 19 | — |
| ≥4 and <5 cm | 15 | — |
| ≥5 and <6 cm | 13 | — |
| ≥6 and <7 cm | 9 | — |
| ≥7 and <8 cm | 8 | — |
| ≥8 and <10 cm | 7 | — |
| ≥10 and <15 cm | 23 | — |
| ≥15 cm | 9 | — |
| NA | 41 | — |

*Exact MELD score was not available for 14 patients from the UTHSCSA cohort, but MELD score could be determined within a range. The upper limit of this range did not exceed 25 for any of the 14 patients.
**Can have more than one cause Spectral Acquisition, Processing and Averaging; Feature Definitions This redevelopment uses the deep MALDI spectra acquired during the test development iteration for Example 1 (Texas samples). Spectra were reacquired from the Thrace samples using identical sample preparation and spectral acquisition procedures. Complete details of sample preparation, spectral acquisition, and spectral averaging can be found in the description of Example 1, above. Identical feature definitions were used as defined in Example 1. For completeness, the 300 mass spectral features identified and used in classifier development are listed in Example 1 Appendix A of this document.

Initial Pre-Processing of Averaged Spectra

The spectra were background subtracted (two windows 80,000/10,000) and normalized using the partial ion current (PIC) windows listed in the table 4, see Example 1.

These windows were selected with a method that protects against using windows that are significantly different between groups of interest (HCC vs. Liver disease), which could lead to a reduction in classification potential, and also against features that are intrinsically unstable. The entire m/z region was divided into 106 bins that varied in size to prevent the bin boundaries from landing within peaks. For each m/z bin, feature values were determined for each sample. The feature values were compared using a Wilcoxon rank-sum test by the group comparisons listed in table 20. If the resulting p value was between 0-0.1, the region was excluded from normalization. If the CV of the feature values (all samples) was greater than 1.0, the region was excluded. Only the 5 windows listed in Example 1, Table 4 met the requirement for all 3 group comparisons. None of these contained high intensity features.

TABLE 20

Group comparisons used to test normalization window dependency on clinical group

| Group | Comparison |
|---|---|
| 1 | HCC versus liver disease and all other development set samples |
| 2 | HCC versus liver disease |
| 3 | HCC and liver disease vs All other development set samples |

Figure 9A:
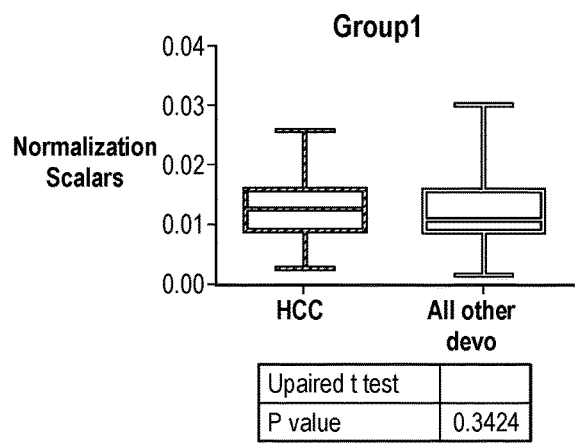
FIGS. 9A-9C are box and whisker plots for normalization scalars by Group showing the results of a normalization step in the preprocessing of mass spectral data for a second example of the development of an early detection HCC classifier of Example 2.
Figure 9B:
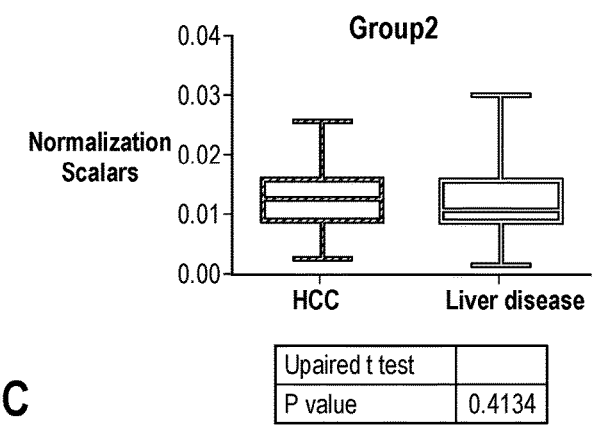
Figure 9C:
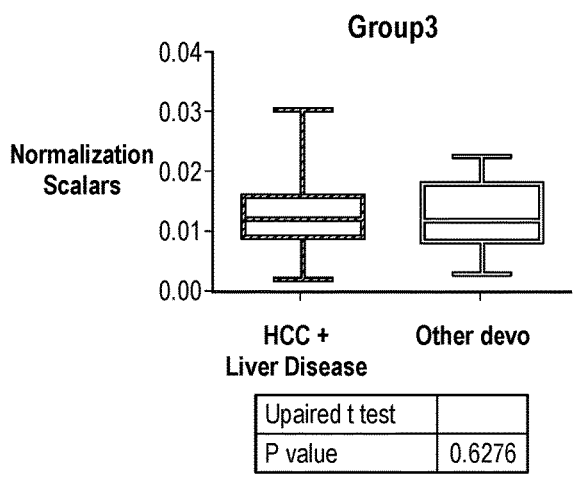

The remaining bins were used as the PIC normalization windows and for each sample a normalization scalar was calculated. A final comparison of groups was performed to ensure that the groups and the normalization parameters used are not correlated. The box and whisker plots of FIGS. 9A, 9B and 9C demonstrate that the groups 1, 2 and 3 have similar distributions of normalization scalars.

The spectra were then aligned using the points listed in table 6 of Example 1 to remove slight differences in alignment.

Analysis of Reference Spectra by Batch, Batch Correction, Normalization

We performed analysis of reference spectra, a batch correction and a partial ion current normalization using the methods explained in the description of Example 1. To normalize, the values of the listed features in Table 21 were summed to find the normalization factor for each sample. All feature values were then divided by the normalization factor to arrive at the final feature table used in CMC/D classifier development.

TABLE 21

Features used in the final normalization found using PIC normalization analysis
m/z

| |
|---|
| 3395 |
| 3559 |
| 3594 |
| 3686 |
| 3774 |
| 3819 |
| 3954 |
| 4015 |
| 4291 |
| 6075 |
| 6205 |
| 6974 |
| 20549 |

Finally, the normalization scalars were checked through the group comparisons to ensure that useful signals were not being reduced from the feature table. While group comparisons 1 and 2 were not significantly different, group comparison 3 was. This is not surprising as we did not use the features found to be most stable in the 'other' group when we arrived at the current list of normalization features. However, the gain in stability achieved through normalization of the HCC and liver damage samples was sufficient to improve the performance of CMC/D (data not shown), and the samples from the "other" group of patients without HCC or underlying liver disease were not used for training or direct performance assessment of the classifier.

Figure 10A:
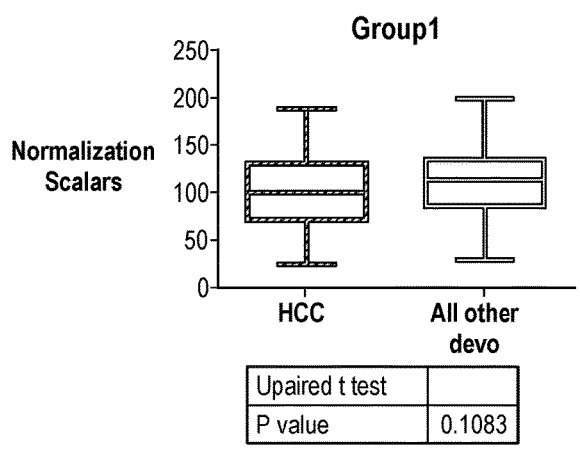
FIGS. 10A-10C are box and whisker plots of the normalization scalars by Group comparison for the final normalization step of Example 2.
Figure 10B:
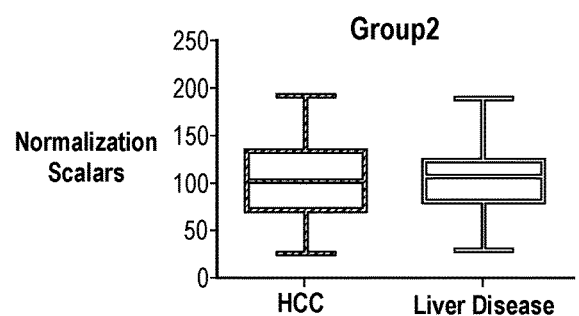
Figure 10C:
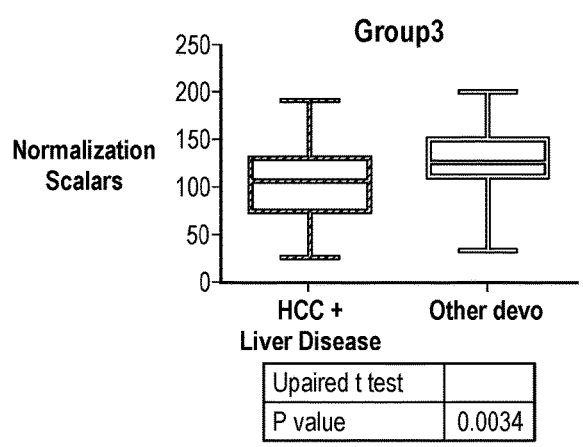

FIG. 10 shows the box and whisker plots of the normalization scalars by Group comparison for the final normalization step for Group 1 (FIG. 10A), Group 2 (FIG. 10B) and Group 3 (FIG. 10C).

Measurement of Alphafetaprotein Expression Level

Previous technical feasibility studies of Example 1 showed that inclusion of serum alphafetoprotein (AFP) level as a feature for new classifier development improved test performance. Prior to redevelopment of the classifier, reproducibility of several measurement methods of AFP were assessed. A kit was selected as having the best reproducibility within the primary area of interest (2<AFP<100 ng/ml).

Assignment of a "VeriStrat-Like" Classification

It has been observed that a classification of VeriStrat Poor (see U.S. Pat. No. 7,736,905) of a blood-based sample occurs infrequently outside of patients with cancer. Hence, a classification of VeriStrat Poor is likely to indicate the presence of cancer, but with a low sensitivity. To use this information in classification of HCC patients, a "VeriStrat-like" classification of the blood-based samples was obtained by averaging 3 deep MALDI 800-shot raster spectra in triplicate and applying the VeriStrat classification algorithm and VeriStrat NSCLC training set to the three averaged spectra. All samples classifying as "VeriStrat-like" Poor were examined to ensure that the classification was not obtained due to the presence of a known confounding peak that can occur with m/Z approximately 11.72 kDa. This peak has been observed in patients with severely compromised liver function and hence this check is very important in this patient population. Samples where the "VeriStrat-like" Poor classification was due to a peak at 11.72 kDa were not classified as "VeriStrat-like" Poor.

"VeriStrat-like" classifications were obtained in this manner for all samples used in this project. They are summarized for the 293 patients in the combined cohort in table 22.

TABLE 22

"VeriStrat-like" classifications for the samples in the combined cohort

|  |  | HCC (N = 158) | No HCC (N = 135) |
|---|---|---|---|
| "VeriStrat-like" classification | good | 126 | 115 |
|  | poor | 26 | 3 |
|  | indeterminate | 3 | 0 |
|  | 11.72 kDa peak interference | 3 | 17 |

Example 2

Classifier Development

Split of Samples Into Classifier Development (FIG. 1, 100) and Internal Validation Sets As explained previously, the sample sets of Example 2 came from two distinct patient populations. The Texas samples were collected at time of resection or transplant for patients with HCC and at time of transplant for patients with no HCC. As a result, there was a large bias in liver function between the two populations: patients with HCC had better liver function than those patients without HCC. The most common cause of underlying liver disease in this cohort was hepatitis C (HCV). In addition, as the HCC patients were eligible for resection or transplant, all patients had relatively early stage HCC. In contrast, the Thrace HCC samples were from patients with later stage cancer; the majority of the HCC patients were BCLC stage 3 or 4 (candidates for sorafenib therapy or best supportive care only). The patients without HCC had generally much better liver function than the corresponding patients from the Texas cohort, and the most common cause of underlying liver disease for both HCC and no HCC patients was hepatitis B (HBV), which is associated with less cirrhosis than HCV infection.

As these two cohorts present complementary patient populations, it was decided to redevelop the classifier on the combination of both cohorts to better represent the range of patients expected in an HCC high risk screening program.

The split into development set (FIG. 1, 100) and validation sets was carried out as follows. All samples with known HCC status from both cohorts, with their associated clinical data, were listed in a spreadsheet. The spreadsheet was sorted by group (HCC/no HCC). HCC samples were grouped according to TNM status, lesion size (T1 1 cm<lesion size≤3 cm, T1 3 cm<lesion size≤4 cm, T1 4 cm<lesion size, T2, T3, T4, NA 2 cm<lesion size≤4 cm, NA 4 cm<lesion size≤6 cm, NA 6 cm<lesion size≤10 cm, NA 10 cm<lesion size≤15 cm, NA 15 cm<lesion size) and sorted by MELD score. Samples were split into adjacent pairings and one was assigned to the development set and the other to the validation set, trying to maintain an overall balance of VeriStrat label, cause of underlying liver disease, and AFP level. No HCC samples were sorted by cause of underlying liver disease, Child-Pugh status, MELD score (where available) and a preliminary assessment of AFP. (For the purpose of this split only a 'minimum' Child-Pugh status was estimated from available clinical data for the Texas samples. Note also that the AFP levels considered for splitting was a preliminary AFP measurement and not those used for classifier development and sample classification.) Clinical characteristics were compared between the resulting development and validation sets and found to be similar, as shown in the table 23.

TABLE 23

Comparison of Clinical Characteristics between Development and Validation Sets

|  | Development Set (N = 148) | | Validation Set (N = 145) | |
|---|---|---|---|---|
|  | HCC (N = 80) | No HCC (N = 68) | HCC (N = 78) | No HCC (N = 67) |
| MELD Score* | | | | |
| Range | 6-34 | — | 7-37 | — |
| Median | 11 | — | 11 | — |
| Mean | 12 | — | 13 | — |
| # samples where NA | 7 | — | 8 | — |

TABLE 23-continued

Comparison of Clinical Characteristics between Development and Validation Sets

|  | Development Set (N = 148) | | Validation Set (N = 145) | |
| --- | --- | --- | --- | --- |
|  | HCC (N = 80) | No HCC (N = 68) | HCC (N = 78) | No HCC (N = 67) |
| BCLC Category | | | | |
| A | 26 | — | 25 | — |
| B | 9 | — | 6 | — |
| C | 35 | — | 38 | — |
| D | 10 | — | 9 | — |
| AFP (in ng/ml) | | | | |
| Range | <1.5->100000 | <1.5-20.0 | <0.8-93612 | <0.8-115 |
| Median | 16.8 | 1.8 | 25.0 | 2.1 |
| Mean | 5439 | 3.0 | 3359 | 4.2 |
| Origin of Cirrhosis (n) | | | | |
| Alcohol | 12 | 12 | 12 | 12 |
| Fatty Liver Disease | 2 | 3 | 3 | 2 |
| Hepatitis A | 0 | 0 | 1 | 0 |
| Hepatitis B | 41 | 29 | 35 | 31 |
| Hepatitis C | 18 | 15 | 20 | 13 |
| Cryptogenic | 9 | 6 | 8 | 7 |
| None | 2 | 0 | 3 | 0 |
| PBC | 1 | 3 | 0 | 4 |
| Autoimmune | 0 | 2 | 0 | 1 |
| TNM T status (n) | | | | |
| 1 | 15 | — | 13 | — |
| 2 | 5 | — | 4 | — |
| 3 | 1 | — | 3 | — |
| 4 | 1 | — | 1 | — |
| NA | 58 | — | 57 | — |
| Lesion Size (cm) | | | | |
| Range | 1.0-28 | — | 1.2-22 | — |
| Median | 5.4 | — | 5.8 | — |
| Mean | 7.4 | — | 7.4 | — |
| lesions between (n) | | | | |
| <2 cm | 3 | — | 3 | — |
| ≥2 and < 3 cm | 5 | — | 3 | — |
| ≥3 and < 4 cm | 8 | — | 11 | — |
| ≥4 and < 5 cm | 8 | — | 7 | — |
| ≥5 and < 6 cm | 7 | — | 6 | — |
| ≥6 and < 7 cm | 5 | — | 4 | — |
| ≥7 and < 8 cm | 4 | — | 4 | — |
| ≥8 and < 10 cm | 3 | — | 4 | — |
| ≥10 and < 15 cm | 12 | — | 11 | — |
| ≥15 cm | 4 | — | 5 | — |
| NA | 21 | — | 20 | — |
| "VeriStrat-like" classification (n) | | | | |
| good | 65 | 57 | 61 | 58 |
| poor | 13 | 2 | 13 | 1 |
| indeterminate | 1 | 0 | 2 | 0 |
| 11.72 kDa peak interference | 1 | 9 | 3 | 8 |

Comparisons:
  MELD HCC development set vs. validation set: t-test p value=0.63
    Mann-Whitney p value=0.55
  AFP HCC development set vs. validation set: t-test p value=0.44
    Mann-Whitney p value=0.73
  AFP No HCC development set vs. validation set: t-test p value=0.48
    Mann-Whitney p value=0.76

The development set 100 (FIG. 1) consisted of 80 HCC samples (56 Thrace, 24 Texas) and 68 No HCC samples (42 Thrace, 26 Texas). In addition, the 32 samples from patients with no HCC and no underlying liver disease were used in development. The validation set consisted of 78 HCC samples (54 Thrace, 24 Texas) and 67 no HCC samples (41 Thrace, 26 Texas).

New Classifier Development Using FIG. 1 Procedure

The new classifier development process was carried out using the procedure of FIG. 1, discussed at length above in Example 1. In addition to the available mass spectral features, AFP level was included in the feature space 122 (FIG. 1).

Definition of Class Labels (102, FIG. 1)

The classifiers were trained using the class labels of HCC and no HCC. As samples with a "VeriStrat-like" classification of Poor (N=15) were deemed very likely to be from patients with cancer, these samples were defined as HCC and not used in training of the classifier.

AFP has been proposed as a screening test for HCC. Elevated levels of AFP are highly suggestive of HCC, although low levels of AFP do not preclude existence of cancer. This lack of adequate performance means that AFP measurement is not currently recommended as a screening test for HCC. Levels of AFP in patients with HCC can exceed the normal range (below 10-20 ng/ml) by many orders of magnitude. Samples with AFP is excess of 100 ng/ml were not used in training the classifier. These samples (N=25) were defined as HCC in the final classification. Samples with AFP lower than or equal to 100 ng/ml were used in training the classifier and AFP level was used as a feature in addition to the 300 mass spectral features.

Creation and Filtering of Mini-Classifiers (Steps 120, 122 of FIG. 1)

The subset of development samples with AFP level less than or equal to 100 ng/ml not classified as "VeriStrat-like" Poor was split into training and test sets (112, 110, respectively in FIG. 1) in 625 different realizations or loops of step 135. Training/test splits were stratified by MELD score, where available. As the procedure of FIG. 1 works best when training classes have the same number of samples, the HCC group was split into 30 training samples and 12 test samples, while the No HCC group was split into 30 training samples and 36 test samples for each realization.

Many k-nearest neighbor (kNN) mini-classifiers (mCs) that use the training set as their reference set were constructed (defined at step 120) using subsets of features. To be able to consider subsets of single, two, or three features and improve classifier performance, it was necessary to deselect features from the set of 301 that were not useful for classification. This was done in a bagged manner (i.e. across multiple sample subsets) based on filtering the performance of kNN classifiers built using single features. This method is described in more detail in the U.S. patent application Ser. No. 62/143,844 of J. Röder et al., filed Apr. 30, 2015, the content of which is incorporated by reference herein.

The essence of the bagged filtering procedure is as follows. A multitude of splits of the development set of available samples into two subsets is created. One of the subsets is used for feature (de)selection and the remainder is left aside. For each split a kNN classifier is created using the given subset as the training set of the classifier and one single feature. For this project k=5 was used. The created classifier is applied to the training subset and a subset of samples from healthy patients and the classifier performance is assessed in terms of classification accuracy. A filter is applied to these performance estimates, such that the feature only passes filtering if the classifier using this sample subset for training has adequate performance. For this project the filter used is defined in table 24.

TABLE 24

Filtering parameters for feature deselection

| Sample Subgroup | Range passing filtering |
|---|---|
| Development subset | 0.5-0.95 |
| Subset of patients without HCC or underlying liver disease used for filtering | 0.65-0.95 |

All features that pass filtering for a given subset choice are added to a list. This is repeated for all the subset realizations generated. The lists of features passing filtering are then compiled across the subset realizations to determine how often a feature passes filtering. Features that pass filtering in most of the subsets are likely to be useful and robust for the question being addressed, as they are not dependent on any particular sample subset. Features that pass filtering for very few subset realizations are likely to have been overfitted to those few subsets and are not likely to be useful.

Features which passed filtering in less or equal to 156 subset realizations (25%) were deselected and only features passing filtering in more than 25% of subset realizations were used for classifier development. The resulting reduced set of features is given in Example 2 Appendix C.

The application of the bagged filtering method resulted in a reduced set of features, which are listed in Example 2 Appendix C, which were used in step 120. While values of k=5, 9, and 11 were tested for the classifier development, the classifiers selected for validation used k=9 and k=11.

To target a final classifier that has certain performance characteristics, these mCs are filtered in step 126. Each mC is applied to its training set and performance metrics are calculated from the resulting classifications of the training set. Only mCs that satisfy thresholds on these performance metrics pass filtering to be used further in the process. The mCs that fail filtering are discarded. For this project only accuracy filtering was used, i.e. the classifier was applied to a set of samples (such as the training set or a subset of the patients without liver disease) and the accuracy of the resulting classification had to lie within a preset range for the mC to pass filtering. The filtering options used in this project are listed in table 25.

TABLE 25

Filtering settings used in step 126, FIG. 1

| Sample Subgroup | Range passing filtering |
|---|---|
| Whole training set | 0.70-0.95 |
| Subset of patients without HCC or underlying liver disease used for filtering | 0.75-0.95 |

This particular problem and patient cohort presents considerable challenges, as differences in liver function between patients are clearly visible in the mass spectra, with very many of the mass spectral features being influenced by the relative level of liver function of the patient from whom a sample was collected. This was even more pronounced in the previous attempt at classifier development, which used only Texas patient samples for which the HCC patients had very markedly better liver function than the No HCC patients (Example 1). This redevelopment mitigated this problem considerably by combining the two complementary patient cohorts. However, confounding by features dependent on liver function still remained a challenge. To avoid creating a classifier for which the performance depended on some level of this confounding factor, an extra filter was used in feature deselection and step 126 to eliminate mCs which would otherwise pass filtering based on relative levels of liver function in the sample subsets. The set of 32 patients with no liver disease and no HCC was split into two subsets. One half was used as a filter on the mCs to ensure that, in addition to adequate performance on the classifier training set, the mC classified a large proportion of these patients with healthy livers as cancer-free. The remaining half of the set of patients with no liver disease was used as a test set to ensure that any final test also classified patients with healthy livers as cancer-free. This method eliminates the possibility of producing a classifier based solely or predominantly on liver function, rather than presence or absence of cancer.

Combination of Mini-Classifiers Using Logistic Regression With Dropout (Step 132)

Once the filtering of the mCs was complete, the mCs were combined in one master classifier 132 (MC) using a logistic regression trained using the training set labels. To help avoid overfitting, the regression is regularized using extreme drop out with only 10 of the mCs chosen randomly for inclusion in each of the 60,000 logistic regression iterations. The number of dropout iterations was selected based on the typical number of mCs passing filtering to ensure that each mC was likely to be included within the drop out process multiple times. The result of step 132 is a set of logistic regression weights for the mC classifiers passing filtering, which define a "master classifier" (MC) for a given training and test set split (step 108).

Training/Test Splits

The use of multiple training/test splits (loop 135) avoids selection of a single, particularly advantageous or difficult, training set for classifier creation and avoids bias in performance assessment from testing on a test set that could be especially easy or difficult to classify.

Final Classifier Definition (Step 144)

The output of the logistic regression that defines each MC (step 132) is a probability of being in one of the two training classes (HCC or No HCC). These MC probabilities can be averaged to yield one average probability for a sample. When working with the development set, this approach is adjusted to average over MCs for which a given sample is not included in the training set. These average probabilities can be converted into a binary classification by applying a threshold (cutoff). ROC curves can be used to investigate the performance of the whole family of classifiers created from the procedure of FIG. 1 which are parameterized by different choices of cutoff and to help chose a cutoff suitable for the clinical question.

Development Set Results

The performance of the classifiers was assessed using ROC curves, which allow the visualization of the sensitivity and specificity obtained for each approach for different values of the cutoff applied to the average probabilities obtained for each sample. When samples were used in training, the average probability was calculated across the realizations (MCs) where the sample was in the test set (out of bag estimate). For samples never used in training, the probability was simply averaged over all training/test set realizations (MCs). Note that the ROC curves also include the samples which are assigned as classification of HCC based on a "VeriStrat-like" classification of Poor or AFP expression level greater than 100 ng/ml. For the purposes of the ROC analysis, these samples are assigned an average probability of 0.

Figure 11:
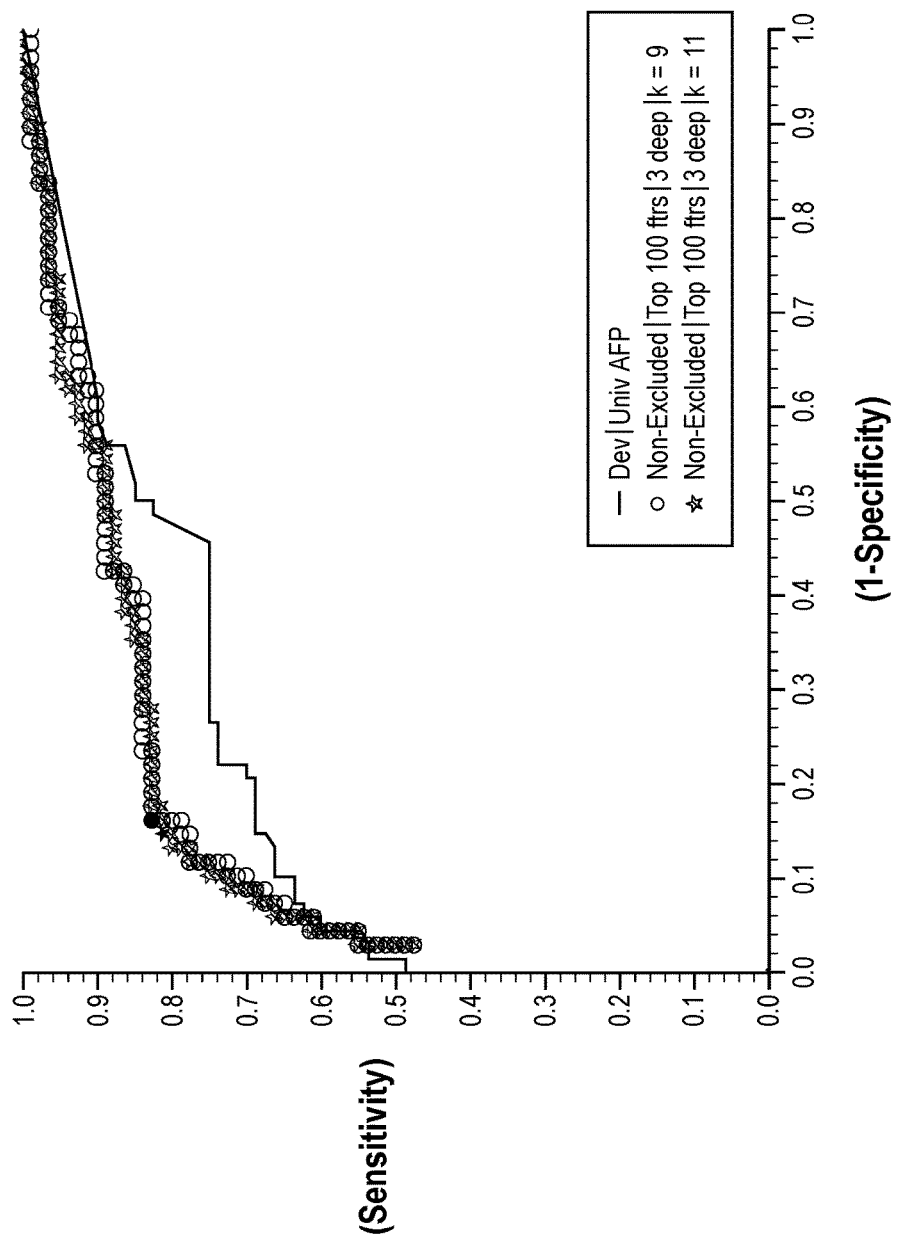
FIG. 11 is a plot of ROC curves for the classifiers for Example 2 (development set) of this disclosure, with k=9 (circles) and k=11 (stars). The solid line shows the ROC curve for univariate AFP level on the development sample set. Solid symbols show the location of the cutoffs selected.

FIG. 11 shows the ROC curves (of the development set) for classifiers created for k=9 and 11. For comparison, the ROC curve for univariate AFP on the development set is also shown. The areas under the curves (AUCs) for the ROC curves are given in table 26. Both classifiers show significantly greater classification power than univariate AFP, especially in the clinical relevant region of desired high sensitivity and specificity.

TABLE 26

AUCs for the ROC curves for the classifiers in FIG. 11

| K | AUC |
|---|---|
| 9 | 86.0 |
| 11 | 86.3 |

To define a test to be validated and evaluate performance of the classifiers by clinical characteristics, a cutoff for average probability (i.e. a point on the ROC curve) must be established. Table 27 contains the cutoff chosen for each k, along with the associated sensitivity and specificity. The location of the cutoffs selected for the k=9 and k=11 classifiers is also shown in FIG. 11 as the solid point.

TABLE 27

Cutoffs chosen and the corresponding sensitivity and specificity on the development set

| K | Cutoff | Sensitivity | Specificity |
|---|---|---|---|
| 9 | 0.317 | 82.5% | 83.8% |
| 11 | 0.336 | 81.3% | 85.3% |

For the classifiers defined in table 27, the classifications of each sample were obtained. The classifier performance in the development set, by origin of underlying liver disease, TNM T stage, tumor size and BCLC category is summarized in tables 28, 29 and 30.

TABLE 28

Performance of the classifiers in the development set by origin of cirrhosis (There may be more than one cause.)

| | k = 9 | | k = 11 | |
|---|---|---|---|---|
| | HCC (N = 80) | No HCC (N = 68) | HCC (N = 80) | No HCC (N = 68) |
| Origin of Cirrhosis | | | | |
| Alcohol | 10/12 (83%) | 10/12 (83%) | 10/12 (83%) | 10/12 (83%) |
| Fatty Liver Disease | 2/2 (100%) | 3/3 (100%) | 2/2 (100%) | 3/3 (100%) |
| Hepatitis B | 36/41 (88%) | 28/29 (97%) | 36/41 (88%) | 28/29 (97%) |
| Hepatitis C | 14/18 (78%) | 10/15 (67%) | 13/18 (72%) | 10/15 (67%) |
| Cryptogenic | 6/9 (67%) | 3/6 (50%) | 6/9 (67%) | 4/6 (67%) |
| None | 1/2 (50%) | 0/0 | 1/2 (50%) | 0/0 |
| PBC | 1/1 (100%) | 3/3 (100%) | 1/1 (100%) | 3/3 (100%) |
| Autoimmune | 0/0 | 2/2 (100%) | 0/0 | 2/2 (100%) |

TABLE 29

Performance of the classifiers within the HCC group of the development set (N = 80) by TNM T stage and tumor size

|  | k = 9 | k = 11 |
|---|---|---|
| TNM T status | | |
| 1 | 10/15 (67%) | 10/15 (67%) |
| 2 | 3/5 (60%) | 2/5 (40%) |
| 3 | 1/1 (100%) | 1/1 (100%) |
| 4 | 1/1 (100%) | 1/1 (100%) |
| NA | 51/58 (88%) | 51/58 (88%) |
| lesions between | | |
| <2 cm | 3/3 (100%) | 2/3 (67%) |
| ≥2 and < 3 cm | 3/5 (60%) | 3/5 (60%) |
| ≥3 and < 4 cm | 4/8 (50%) | 4/8 (50%) |
| ≥4 and < 5 cm | 8/8 (100%) | 8/8 (100%) |
| ≥5 and < 6 cm | 5/7 (71%) | 5/7 (71%) |
| ≥6 and < 7 cm | 5/5 (100%) | 5/5 (100%) |
| ≥7 and < 8 cm | 4/4 (100%) | 4/4 (100%) |
| ≥8 and < 10 cm | 1/3 (33%) | 1/3 (33%) |
| ≥10 and < 15 cm | 10/12 (83%) | 10/12 (83%) |
| ≥15 cm | 4/4 (100%) | 4/4 (100%) |
| NA | 19/21 (90%) | 19/21 (90%) |

TABLE 30

Performance of the selected classifiers within the HCC group of the development set (N = 80) by BCLC category

|  | k = 9 | k = 11 |
|---|---|---|
| BCLC Category | | |
| A | 19/26 (73%) | 18/26 (69%) |
| B | 4/9 (44%) | 4/9 (44%) |
| C | 33/35 (94%) | 33/35 (94%) |
| D | 10/10 (100%) | 10/10 (100%) |

The data in tables 28-30 show that the classifiers have good performance across patients with underlying liver disease independent of the origin of liver disease. The classifiers correctly identified as HCC 14 of 16 patients with larger tumors (greater than 10 cm) and both patients classified as T=3 or 4. The sensitivity in detection of the smallest tumors was still high (100% for the k=9 classifier for lesions smaller than 2 cm, 75% for lesions smaller than 75% and 67% lesions classified as T1). Of great importance, the classifiers identified 73% (k=9) and 69% (k=11) of patients from BCLC category A, those eligible for resection or transplant as treatment for HCC. The accuracy for identification of patients in the later stages of HCC, where patients are currently most commonly diagnosed, was over 95%.

It was found from classifying samples from the test set of patients without liver disease or HCC that patients with healthy liver are predominantly classified as No HCC. In addition, the four patients who had had HCC, but had no viable tumor mass at time of transplant or resection, generally classified as HCC. This data is shown in tables 31 and 32.

TABLE 31

Number of patients with healthy liver (no HCC and no underlying liver disease) used in the test set correctly classified

| k | "Healthy liver" patients correctly classified as No HCC |
|---|---|
| 9 | 14/16 |
| 11 | 14/16 |

TABLE 32

Classifications of the patients diagnosed with HCC but with no viable tumor at the time of treatment

| k | HCC Patients with no viable tumor at time of surgery classified as HCC |
|---|---|
| 9 | 4/4 |
| 11 | 3/4 |

Validation Set Results

Recall from the previous discussion that the set of samples available for the classifier development exercise of Example 2 was split initially into development and validation sets. The two developed classifiers (k=9, k=11) defined at step 144 of FIG. 1 were applied to the mass spectrometry data of the validation set of samples. AFP level was also assayed in the validation set of samples and used as a feature in the feature space for classifier training per FIG. 1. The results are compared with those of univariate APF in the validation set and the results in the development set, together with the corresponding univariate AFP, in FIGS. 12 and 13. The location of the cutoff is shown as the solid circles and the solid stars in FIGS. 12 and 13. The classifiers validate well across the whole ROC curve and in terms of AUC. The increased classification power relative to univariate AFP remains of similar magnitude.

The AUCs for the validation set for the two classifiers are given in table 33 and the sensitivity and specificity for the chosen cutoffs are shown in table 34.

TABLE 33

Figure 12:
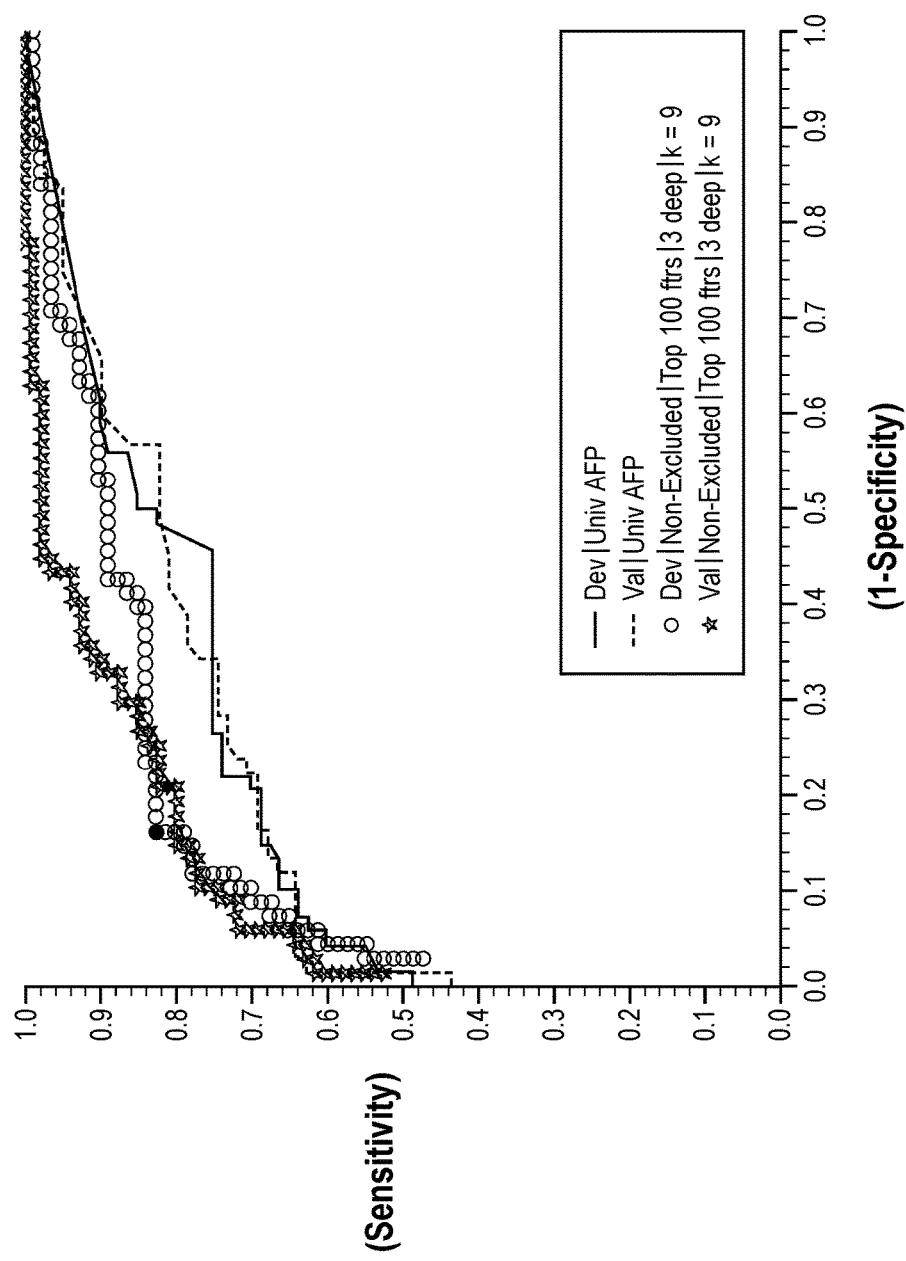
FIG. 12 is a plot of ROC curves for the k=9 classifier showing the development set (circles) and validation set (stars) results of Example 2. Solid symbols show the location of the chosen cutoff. The ROC curves for univariate AFP in the two sample sets are also shown in the Figure.
Figure 13:
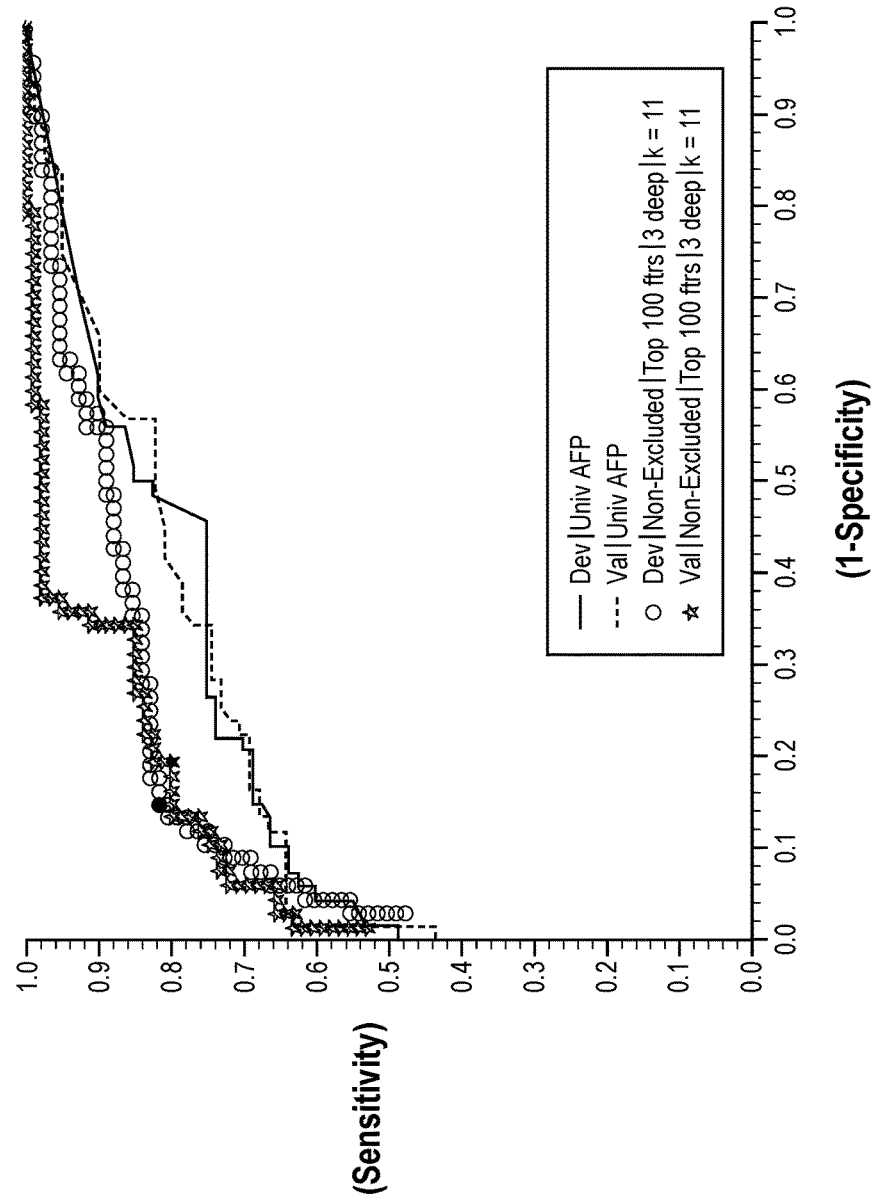
FIG. 13 is a plot of the ROC curves for the k=11 classifier showing the development set (circles) and validation set (stars) results in Example 2. Solid symbols show the location of the chosen cutoff. The ROC curves for univariate AFP in the two sample sets are also shown in the Figure.

AUCs for the ROC curves for the classifiers of FIGS. 12 and 13 applied to the validation set

| K | AUC |
|---|---|
| 9 | 90.4 |
| 11 | 90.7 |

TABLE 34

Cutoffs chosen and the corresponding sensitivity and specificity on the validation set

| K | Cutoff | Sensitivity | Specificity |
|---|---|---|---|
| 9 | 0.317 | 80.8% | 79.1% |
| 11 | 0.336 | 79.5% | 80.6% |

The performance by origin of underlying liver disease, TNM T stage, and tumor size is summarized in tables 35, 36 and 37.

TABLE 35

Performance of the classifiers in the validation set by origin of cirrhosis (There may be more than one cause.)

|  | k = 9 | | k = 11 | |
| --- | --- | --- | --- | --- |
|  | HCC (N = 78) | No HCC (N = 67) | HCC (N = 78) | No HCC (N = 67) |
| Origin of Cirrhosis | | | | |
| Alcohol | 8/12 (67%) | 8/12 (67%) | 8/12 (67%) | 9/12 (75%) |
| Fatty Liver Disease | 2/3 (67%) | 1/2 (50%) | 2/3 (67%) | 1/2 (50%) |
| Hepatitis A | 0/1 (0%) | 0/0 | 0/1 (0%) | 0/0 |
| Hepatitis B | 31/35 (89%) | 29/31 (94%) | 30/35 (86%) | 29/31 (94%) |
| Hepatitis C | 18/20 (90%) | 8/13 (62%) | 18/20 (90%) | 9/13 (69%) |
| Cryptogenic | 6/8 (75%) | 4/7 (57%) | 6/8 (75%) | 4/7 (57%) |
| None | 2/3 (67%) | 0/0 | 2/3 (67%) | 0/0 |
| PBC | 0/0 | 4/4 (100%) | 0/0 | 3/4 (75%) |
| Autoimmune | 0/0 | 1/1 (100%) | 0/0 | 1/1 (100%) |

TABLE 36

Performance of the classifiers within the HCC group of the validation set (N = 78) by TNM T stage and tumor size

|  | k = 9 | k = 11 |
| --- | --- | --- |
| TNM T status | | |
| 1 | 6/13 (46%) | 6/13 (46%) |
| 2 | 3/4 (75%) | 3/4 (75%) |
| 3 | 3/3 (100%) | 3/3 (100%) |
| 4 | 1/1 (100%) | 1/1 (100%) |
| NA | 50/57 (88%) | 49/57 (86%) |
| lesions between (n) | | |
| <2 cm | 1/3 (33%) | 1/3 (33%) |
| ≥2 and <3 cm | 3/3 (100%) | 3/3 (100%) |
| ≥3 and <4 cm | 7/11 (64%) | 7/11 (64%) |
| ≥4 and <5 cm | 4/7 (57%) | 4/7 (57%) |
| ≥5 and <6 cm | 5/6 (83%) | 5/6 (83%) |
| ≥6 and <7 cm | 4/4 (100%) | 4/4 (100%) |
| ≥7 and <8 cm | 3/4 (75%) | 3/4 (75%) |
| ≥8 and <10 cm | 2/4 (50%) | 2/4 (50%) |
| ≥10 and <15 cm | 10/11 (91%) | 10/11 (91%) |
| ≥15 cm | 5/5 (100%) | 5/5 (100%) |
| NA | 19/20 (95%) | 18/20 (90%) |

TABLE 37

Performance of the selected classifiers within the HCC group of the validation set (N = 78) by BCLC

|  | k = 9 | k = 11 |
| --- | --- | --- |
| BCLC Category | | |
| A | 16/25 (64%) | 16/25 (64%) |
| B | 3/6 (50%) | 3/6 (50%) |
| C | 35/38 (92%) | 34/38 (89%) |
| D | 9/9 (100%) | 9/9 (100%) |

While accuracy in detecting the smallest lesions (<2 cm and T1) is smaller than in the development set, this difference may be due to the small number of available samples. Accuracy for tumors of size smaller than 3 cm is still 67% and the accuracy of identification of patients with early stage HCC (BCLC category A) is still relatively high (64%). Accuracy of identification of patients with later stage HCC (BCLC C and D) validated well at 94% (for k=9 classifier).

Example 2

Conclusions

Example 2 has demonstrated the development of two classifiers, both with performance exceeding 80% sensitivity and 80% specificity on the development set. Both classifiers validated well on the validation set, both with close to 80% sensitivity and 80% specificity, showing that the performance estimates calculated on the development set were reliable. The classifiers consistently showed clearly better performance than univariate AFP in terms of AUC and increased sensitivity at fixed specificity of clinical relevance. The performance of the two classifiers (k=9, k=11) is very similar with no real significant differences to indicate a preference for one over the other.

It is difficult to obtain a reliable estimate of classifier performance for very small lesions. These lesions are often not reliably detected with current screening and diagnostic methods and, even though we were fortunate to have a sample cohort from patients with the earliest stages of HCC, amenable to treatment by resection or transplant, there were only 6 patients with known lesion sizes smaller than 2 cm and only 14 patients with known lesion sizes smaller than 3 cm. Across the combined cohort, the k=9 classifier identified 67% (4/6) of the patients with lesion sizes smaller than 2 cm and 71% (10/14) of the patients with lesion sizes smaller than 3 cm. The classifiers were able to detect early stage HCC (BCLC category A) with an accuracy of 69% across the whole sample set. This is particularly important, as currently less than 30% of patients are diagnosed at this early stage of disease where intervention, in the form of resection or transplant, can dramatically improve outcomes.

III. Laboratory Test Center and Computer-Implemented Classifier (FIG. 8)

FIG. 8 is an illustration of a laboratory testing center or system for processing a test sample (in this example a blood-based sample from a patient with liver disease) using a classifier generated in accordance with FIG. 1 and generating a label or result (HCC, No HCC) for the sample. The system includes a mass spectrometer 806 and a general purpose computer 810 having CPU 812 implementing a CMC/D classifier 820 coded as machine-readable instructions and a reference mass spectral data set including a feature table 822 of class-labeled mass spectrometry data stored in memory 814. It will be appreciated that the mass spectrometer 806 and computer 810 of FIG. 8 could be used to generate the CMC/D classifier 820 in accordance with the process of FIG. 1.

The operation of the system of FIG. 8 will be described in the context of a test of whether a patient providing the blood sample has HCC. The following discussion assumes that the CMC/D classifier 820 is already generated at the time of use of the classifier to generate a label or panel of labels for a test sample.

The system of FIG. 8 obtains a multitude of samples 800, e.g., blood-based samples (serum or plasma) from diverse liver disease patients and generates a label or panel of labels as a fee-for-service. The samples 800 are used by the classifier (implemented in the computer 810) to detect presence of HCC. The outcome of the test is a binary class label (or panel of such labels), such as HCC, No HCC, or the like. The particular moniker for the class label or result reported is not particularly important and could be generic such as "class 1", "class 2" or the like, but as noted earlier the class label is associated with a clinical attribute relevant to the question being answered by the classifier, in this case, presence or absence of HCC.

The samples may be obtained on serum cards or the like in which the blood-based sample is blotted onto a cellulose or other type card. Aliquots of the sample are spotted onto several spots of a MALDI-ToF sample "plate" 802 and the plate inserted into a MALDI-ToF mass spectrometer 806. The mass spectrometer 806 acquires mass spectra 808 from each of the spots of the sample. The mass spectra are represented in digital form and supplied to a programmed general purpose computer 810. The computer 810 includes a central processing unit 812 executing programmed instructions. The memory 814 stores the data representing the mass spectra 808. The spectral acquisition details, including deep-MALDI (100,000+laser shots) and spectra processing that was used in classifier generation (described at length above) is also used for a test sample.

The memory 814 also stores a final CMC/D classifier 820, which includes a) a reference mass spectral data set 822 in the form of a feature table of N class-labeled spectra, where N is some integer number, in this example the development set used to develop the classifier as explained above or some sub-set of the development sample set (e.g., after exclusion of those patients with high AFP level). The reference set may optionally include the serum AFP expression level for each member in the training set, and this AFP level may be used as a feature for classification in addition to the mass spectral features. It will be noted from the previous discussion that some of the classifiers we developed use AFP level as an additional feature for classification whereas other classifiers did not use AFP level and only used mass spectral features. The final CMC/D classifier includes b) code 824 representing a kNN classification algorithm (which is implemented in the mini-classifiers as explained above), c) program code 826 for executing the final classifier generated in accordance with FIG. 1 on the mass spectra of patients, including logistic regression weights, probability cutoff, and data representing master classifier(s) forming the final classifier, and d) a data structure 828 for storing classification results, including a final class label for the test sample. The memory 814 also stores program code 830 for implementing the processing shown at 850, including code (not shown) for acquiring the mass spectral data from the mass spectrometer in step 852; a pre-processing routine 832 for implementing the background subtraction, normalization and alignment step 854 (details explained above), a module (not shown) for filtering and averaging of the 800 shot spectra at multiple locations per spot and over multiple MALDI spots to make a single 100,000+shot average spectrum (as explained above), a module for calculating integrated intensity values at predefined m/z positions in the background subtracted, normalized and aligned spectrum (step 856), and a code routine 838 for implementing the final classifier 820 using the reference dataset 822 on the values obtained at step 856. The process 858 produces a class label at step 860. The module 840 reports the class label as indicated at 860 (i.e., "HCC", "No HCC" or the equivalent).

The program code 830 can include additional and optional modules, for example a feature correction function code 836 (described in co-pending U.S. patent application Ser. No. 14/486,442) for correcting fluctuations in performance of the mass spectrometer, a set of routines for processing the spectrum from a reference sample to define a feature correction function, a module storing feature dependent noise characteristics and generating noisy feature value realizations and classifying such noisy feature value realizations, modules storing statistical algorithms for obtaining statistical data on the performance of the classifier on the noisy feature value realizations, or modules to combine class labels defined from multiple individual replicate testing of a sample to produce a single class label for that sample. Still other optional software modules could be included as will be apparent to persons skilled in the art.

The system of FIG. 8 can be implemented as a laboratory test processing center obtaining a multitude of patient samples from oncologists, patients, clinics, etc., and generating a class label for the patient samples as a fee-for-service. The mass spectrometer 806 need not be physically located at the laboratory test center but rather the computer 810 could obtain the data representing the mass spectra of the test sample over a computer network. In one embodiment, where AFP level is also used in the classification algorithm, a blood-based sample of the patient is also subject to AFP assay to measure the serum AFP level and the value stored in the memory of the computer. This level is then used in the classification algorithm along with the mass spectral data from the blood-based sample. The instrumentation for conducting the AFP assay may be physically included in the laboratory testing center, or alternatively it may exist at the laboratory of a third party testing service. In the latter situation, some suitable amount of the blood-based sample obtained from the patient is sent off to the third party for AFP testing and the results are returned and stored in the memory for use by the classifier.

Further Considerations

It will be noted that the classifiers we generated can, for example, use the features of Example 1 Appendix A (or some subset thereof) or Example 2 Appendix C (or some subset thereof) and we have not determined precisely what proteins these peaks correspond to. Nor is it necessary. What matters is classifier performance. We believe that they may involve, directly or indirectly, the protein biomarkers mentioned in the scientific literature cited at the beginning of this document. Note that, with our "deep MALDI" mass spectrometry and the use of 50, 100 or even 200 or more peaks, it is likely that our classifiers are based on still undiscovered protein biomarkers circulating in serum. Our method essentially takes advantage of the fact that we can detect these proteins, and in particular low abundance proteins, using the>100,000 shot MALDI-TOF mass spectra, and use them in development and application of a classifier, even though we do not know precisely what proteins the peaks correspond to.

It will also be understood that the exact parameters of a final classifier used for classification of a test sample as HCC, or No HCC, may vary considerably depending on exactly how one wishes to tune the classifier's parameters for performance. In the above Tables we have described the parameters for numerous possible classifiers we considered. The ROC curves also show performance of numerous approaches to classifier generation and parameter tuning.

These considerations include the following additional thoughts regarding an "optimal" classifier for early detection of HCC.

a. Number of Mass-Spectral Features

The number of features to use for classification that is considered "optimal" could be all 300 features of Example 1 Appendix A, 100 selected using t-statistic for discriminating power, 50 selected from a condensed feature set, or some other number or features, for example the subset of features listed in Example 1 Appendix B or Example 2 Appendix C. To understand this, the question is what one means by optimal; within the unavoidable uncertainty arising from a limited development set, there appear to be quite a few tests one can build that perform about equally well. The number may also depend on whether sensitivity or specificity is more important in clinical practice. In Example 1, we have evaluated four classifiers with the specified probability cut-offs, namely:

1. One with the best development performance balance between sensitivity and specificity, such as 85% sensitivity, 81% specificity, in the classifier development sample set.
2. One not using serum AFP level as a feature for classification.
3. One with high specificity.
4. One from the condensed set of features.

Several ideas are in play here, namely a) detect as many early stage HCC patients as possible (push sensitivity); b) Try to avoid using out-of-platform values, such as the classifier not using AFP level, to make the test easier to commercialize (that is, it is technically easier if one does not need to run an ELISA assay and/or get test results from a third party, such as AFP level, moreover there is also a question of sample volume and the use of cards to do such "out-of-platform" extra assays); c) Avoid false positives due to cost issues of follow-up; and d) try to optimize the classifier for robustness and maximum reproducibility. In particular, as to item d), the idea of defining features on averages from a smaller number of shots and then calculating features from spectra averaged over many more shots is one way to pick features that we believe will be more reproducible and have bigger signal to noise (S/N) ratios. As we increase the number of shots the coefficient of variance (CV) of peaks tends to decrease (although not below some intrinsic level due to other sources of irreproducibility such as sample preparations issues) and new peaks appear. These new peaks have higher CVs, as they have just emerged from the noise by averaging more shots. This idea could therefore help us to drop some noisy features (as an alternative to feature de-selection by t-test), and it could also help us to just have features that are more reproducible. This latter could help make life easier with establishing any final test as reproducible for satisfaction of regulatory bodies.

In terms of feature de-selecting, it appears to be better to weed out 'noisy' features that do not add information, the exact number of how many to retain is not that important. Hence, the list of features of Example 2 Appendix C is example of a reduced set of features that performs well.

b. Optimal Depth of mC (# of Features, Parameter s)

It turns out that here increasing the depth s appears to help, we get better results with three, and sometimes four deep (in the case of condensed features). Four deep does not appear to help for non-condensed features. It was hard to do a lot with 4 deep with 100 features, and 5 deep was prohibitive (run-time) even for 50 features. We did one or two runs 4 deep with 100 features, but the results were not any better than with 3 deep. It is quite time-consuming to try out many parameter settings while varying the depth of the miniClassifiers above 3 with our existing computing resources. So, we cannot say, in the abstract, what depth is optimal, only that 4 deep was better than 3 deep and 2 deep for 50 condensed features, and 3 deep was better than 2 deep for 100 features. Thus, the optimal depth of mC features depends somewhat on the number of features used in classification.

c. The Training/Reference Set: Characteristics of the Patients Making up the Training Set (Step 108, FIG. 1)

We explored developing classifiers which both included and excluded patients from the training set with high AFP levels. One of the candidate classifiers trained on all patients with HCC and did not drop those with high AFP from the training set. On the other hand, some classifiers we explored performed worse when patients with high AFP were included in the training set. So, when developing the classifier one should explore all options and select the classifier with best performance and such classifier will have a training set that may or may not exclude samples from patients with high AFP levels. The same remarks could hold for other non-mass spectrometry measurements of a biomarker that may be associated with liver disease besides AFP. In addition, to target classifier performance at a particular subpopulation or to broaden performance across a wider population, the clinical characteristics of the patients whose samples are used in training the classifier can play an important role. Changing the clinical profile of the sample set used for classifier training can also be used to tune classifier performance. In particular, it could be advantageous to add to the development set samples from patients with liver disease but no HCC with better liver function than those eligible for liver transplant (the No HCC population in our development set) or samples from patients with liver disease from under-represented origins. This could potentially improve performance of the classifier in the more general high risk screening population.

d. Value of K in K-Nearest Neighbor Algorithm (Step 120, FIG. 1)

It will be noted from Table 11 of Example 1 and in Example 2 that we explored a variety of classifiers with different values of K for the mini-classifiers. Some of the classifiers use K=11. During classifier development we found some classifiers that had better performance with lower values of K. The 'All samples' classifier and the 'No AFP' (excluding high-AFP patients) classifier used K=11, the condensed features classifier used K=7 and the "Non-excluded by AFP" classifier used K=5. Therefore, the optimal value of K depends on a variety of factors and may be arrived at by trial and error and selecting the value with the best classifier performance.

e. Healthy Subgroup Filtering of mC (Step 126, FIG. 1)

We explored several different values for the filtering of the mC (step 126 in FIG. 1), based on how well the mCs classified mass spectra of healthy patients as No HCC, such as 0.5<healthy pt. accuracy<1.0, 0.6<healthy pt. accuracy<1.0, and others. The optimal values selected for the healthy subgroup filtering depends strongly on the particular classifier one is generating. We found in development that trying to make this range as broad as possible generally gave better performance until one hits the point where liver function takes over and the healthy patients start to classify randomly, or all as HCC. The parameters should be selected such that we should use information from as many mCs as possible (i.e., wide filtering, e.g., 0.6<health pt. accuracy<1) as long as the liver function bias does not take over.

f. Definition of Final Classifier (Step 144, FIG. 1)

As noted previously, there are several possible approaches for defining a final classifier at step 144 of FIG. 1 making use of all the MCs resulting from the successive iterations of the process of FIG. 1. One possibility is using a majority vote of all the MCs. Another possibility is selecting a cutoff (e.g., 0.5) for the average probability over all the MCs, taking into account the ROC curves produced by the classifier and computing the average of the probabilities of the MCs, and then assigning the class label based on whether the average is over or under the cutoff. We have explored cutoffs for average probability for all four candidate classifiers from Example 1 and two more from Example 2. While one cutoff is very close to 0.5, and so also close to what one would obtain using a modified majority vote (MMV) procedure, the others are quite a bit lower and have improved performance.

For a test on a patient sample, we currently envision generating a single label (HCC, No HCC), perhaps reported as a probability (percentage) as explained above. To improve performance one may optionally implement different classifiers for different levels of liver function of the patient (e.g. higher MELD or lower MELD) or possibly HBV versus other origins of cirrhosis, and report the results of such classifiers in addition to the class label or percentage as a combination or panel of results.

IV. Alternative HCC Testing Methods

An alternative testing procedure for early detection of HCC in patients with liver disease is contemplated as follows.

First, conduct a test of the blood-based sample using mass spectrometry to see if the patient's mass spectrum classifies as "Poor" under the VeriStrat® test of the applicants' assignee. The VeriStrat test is described in U.S. Pat. No. 7,736,905 and F. Taguchi et al. *Mass Spectrometry to Classify Non-Small-Cell Lung Cancer Patients for Clinical Outcome After Treatment with Epidermal Growth Factor Receptor Tyrosine Kinase Inhibitors: a Multicohort Cross-Institutional Study* J.N.C.I. vol. 99 pp. 838-846 (2007), the contents of which are incorporated by reference herein. Basically, in this test, the integrated intensity values of a mass spectrum of a serum or plasma sample of a patient at pre-defined m/z features as identified in the '905 patent are compared to values of such features in a training set of class-labeled spectra obtained from blood-based samples from non-small cell lung cancer patients using a k-NN classification algorithm (the commercial version of the test does not use the CMC/D classifier). The class label for the sample under test results from comparing the feature values of the test spectrum to the nearest neighbors in multi-dimensional feature space and assigning a class label by majority vote. Such spectra in the training set are labeled "Good" if such patients in the training set had better outcomes from an epidermal growth factor receptor inhibitor (EGFR-I) administered in treatment of the NSCLC as compared to patients having the Poor class label. The VeriStrat test produces a class label for a test sample, either VeriStrat Good (or simply "Good") or VeriStrat Poor (or simply "Poor"). In some rare instances the test can produce a class label of Indeterminate. In multiple clinical validation studies it has been shown that, for many different types of solid epithelial tumor cancers, patients whose pre-treatment serum/plasma was VeriStrat "Good", have significantly better outcome when treated with EGFR-Is than those patients whose sample results in a VeriStrat "Poor" signature. See the published application of J. Grigorieva, et al., U.S. 2011/0208433, the content of which is incorporated by reference herein. The Poor mass spectral signature has been identified previously as indicative of a relatively poor prognosis of solid epithelial tumor cancer patients. The Poor signature is believed to be indicative of the presence of cancer. So, in the present testing example, if the patient's serum sample tests Poor under the VeriStrat test, the patient (with liver disease) is indicated as being likely to have HCC and the blood-based sample does not have to be subjected to the HCC/No HCC test described previously in this document.

Second, if in the first test the patients' sample is classified as Good under the VeriStrat test (or Indeterminate), the patient's mass spectrum is then subject to the HCC/No HCC test described previously in this document, see FIG. 8. Most liver disease patients with HCC are classified as Good under the VeriStrat test, so one needs to do the HCC/No HCC test for these patients. If the result of this test is the class label of "HCC" or the equivalent, then such patients are identified as having HCC and this is reported. If the result of this test is the class label "No HCC" or the equivalent, then they are identified as not having HCC and this result is reported.

In one embodiment, the first test for Poor status makes use of spectra that are obtained from the deep MALDI mass spectra described previously in this document. In particular, since the VeriStrat test of the '905 patent does not use deep MALDI spectra but rather ~2000 shot spectra from three aliquots of the blood-based sample, we mimic such spectra by extracting the spectra from three different 800 shot spectra, each 800 shot spectra obtained at different physical locations on a single spot on a MALDI plate and average these to create one 2400 shot spectrum. We do this in triplicate from three different spots, or optionally from one or two spots on a MALDI plate, to provide the three replicate spectra required for the VeriStrat test. (It will be remembered that in the deep MALDI spectral acquisition described previously, 800 shot spectra are acquired from 63 different locations on 3 separate spots on MALDI plate which are then subject to averaging and other processing steps). So, the blood-based sample obtained from a patient with liver disease only need to be subject to mass spectrometry once in this variation of the test, and preferably in the Deep-MALDI method as described at length above in case the sample tests Good under the first test and then proceeds to be tested under the HCC/No HCC test.

In theory, one could conduct the HCC/No HCC test even if the sample tests Poor under the VeriStrat test. If the patient's sample classifies as Poor, and as "HCC" under the HCC/No HCC test, it gives even greater confidence that the HCC class label is correctly indicating the presence of HCC.

In a further variation, a test for detection of HCC in high risk populations is as follows: a) conduct an AFP expression level test and if the AFP expression level is>100 ng/ml the patient is classified as HCC. If the AFP expression level is≤100 ng/ml, the HCC/No HCC test described in this document is conducted. If the HCC/No HCC test result is HCC, the HCC result is reported. If the patient tests as No HCC, the No HCC result is reported.

As a further variation, a three-stage testing process is described. In stage 1, the patient is subject to the VeriStrat test described in the previous paragraphs and U.S. Pat. No. 7,736,905. If the patient tests as VeriStrat Poor, the HCC result is reported. In stage 2, if the Patient tests VeriStrat Good, then conduct the AFP expression level test. If the patient tests with an AFP expression level>100 ng/ml, then report the HCC result. In stage 3, if the VeriStrat Good patient's AFP expression level is ≤100 ng/ml, then conduct the HCC/No HCC test of this document and report the result of that test.

The appended claims are offered as further descriptions of the disclosed inventions.

Appendices

Example 1

Appendix A: Feature Definitions

| Left | Center | Right |
|---|---|---|
| 3120.97 | 3132.28 | 3143.58 |
| 3144.12 | 3155.69 | 3167.27 |
| 3384.08 | 3395.16 | 3406.23 |
| 3408.04 | 3422.03 | 3436.02 |
| 3542.72 | 3558.63 | 3574.53 |
| 3582.98 | 3594.26 | 3605.53 |
| 3674.87 | 3686.35 | 3697.82 |
| 3760.14 | 3774.13 | 3788.12 |
| 3806.24 | 3818.82 | 3831.40 |
| 3856.97 | 3869.35 | 3881.73 |
| 3916.36 | 3928.94 | 3941.52 |
| 3943.13 | 3953.50 | 3963.87 |
| 4001.11 | 4015.00 | 4028.89 |
| 4040.17 | 4053.15 | 4066.14 |
| 4275.28 | 4290.71 | 4306.15 |
| 4875.22 | 4890.97 | 4906.72 |
| 4925.11 | 4937.26 | 4949.42 |
| 4978.09 | 4994.69 | 5011.30 |
| 5538.23 | 5560.98 | 5583.73 |
| 5617.26 | 5634.92 | 5652.58 |
| 5887.06 | 5905.52 | 5923.98 |
| 6052.67 | 6075.36 | 6098.05 |
| 6182.01 | 6205.21 | 6228.41 |
| 3033.39 | 3043.08 | 3052.77 |
| 3076.79 | 3088.26 | 3099.74 |
| 3100.53 | 3109.47 | 3118.41 |
| 3181.96 | 3188.28 | 3194.61 |
| 3196.98 | 3203.71 | 3210.45 |
| 3210.84 | 3219.94 | 3229.04 |
| 3229.67 | 3241.25 | 3252.83 |
| 3253.23 | 3263.29 | 3273.36 |
| 3273.56 | 3286.24 | 3298.93 |
| 3300.10 | 3312.52 | 3324.95 |
| 3325.11 | 3334.68 | 3344.26 |
| 3356.70 | 3369.99 | 3383.28 |
| 3436.83 | 3446.59 | 3456.35 |
| 3456.56 | 3465.51 | 3474.47 |
| 3498.50 | 3511.87 | 3525.24 |
| 3699.24 | 3708.03 | 3716.81 |
| 3788.32 | 3797.18 | 3806.04 |
| 3831.61 | 3843.99 | 3856.37 |
| 3882.14 | 3890.89 | 3899.65 |
| 3900.05 | 3907.70 | 3915.35 |
| 3964.20 | 3975.77 | 3987.33 |
| 4078.76 | 4093.64 | 4108.52 |
| 4114.45 | 4121.20 | 4127.94 |
| 4128.14 | 4135.99 | 4143.84 |
| 4204.62 | 4210.25 | 4215.88 |
| 4215.95 | 4221.58 | 4227.20 |
| 4230.26 | 4244.74 | 4259.22 |
| 4260.62 | 4267.38 | 4274.14 |
| 4306.57 | 4318.72 | 4330.88 |
| 4332.18 | 4341.37 | 4350.56 |
| 4351.18 | 4361.06 | 4370.94 |
| 4371.19 | 4378.76 | 4386.34 |
| 4386.42 | 4393.22 | 4400.02 |
| 4400.36 | 4409.29 | 4418.23 |
| 4418.48 | 4426.49 | 4434.51 |
| 4449.57 | 4456.23 | 4462.88 |
| 4462.92 | 4471.86 | 4480.79 |
| 4521.81 | 4529.99 | 4538.17 |
| 4538.34 | 4547.75 | 4557.17 |
| 4559.36 | 4570.55 | 4581.73 |

-continued

| Left | Center | Right |
|---|---|---|
| 4581.81 | 4586.52 | 4591.23 |
| 4591.60 | 4600.18 | 4608.76 |
| 4618.52 | 4626.79 | 4635.05 |
| 4635.09 | 4646.56 | 4658.03 |
| 4668.49 | 4680.92 | 4693.35 |
| 4698.66 | 4711.22 | 4723.77 |
| 4748.42 | 4756.67 | 4764.91 |
| 4768.55 | 4775.84 | 4783.12 |
| 4783.33 | 4792.26 | 4801.20 |
| 4802.98 | 4818.65 | 4834.32 |
| 4846.65 | 4856.27 | 4865.90 |
| 4950.50 | 4962.87 | 4975.23 |
| 5011.71 | 5023.51 | 5035.31 |
| 5037.25 | 5045.01 | 5052.78 |
| 5052.88 | 5065.50 | 5078.12 |
| 5078.22 | 5086.70 | 5095.18 |
| 5095.28 | 5107.75 | 5120.21 |
| 5120.42 | 5129.61 | 5138.81 |
| 5139.22 | 5148.31 | 5157.40 |
| 5166.37 | 5176.18 | 5185.99 |
| 5186.62 | 5195.87 | 5205.12 |
| 5206.57 | 5222.14 | 5237.70 |
| 5260.04 | 5270.05 | 5280.07 |
| 5280.43 | 5289.47 | 5298.50 |
| 5317.72 | 5329.70 | 5341.67 |
| 5351.85 | 5360.73 | 5369.61 |
| 5396.95 | 5407.02 | 5417.10 |
| 5421.09 | 5430.67 | 5440.25 |
| 5440.61 | 5453.46 | 5466.31 |
| 5466.99 | 5474.16 | 5481.33 |
| 5482.34 | 5491.64 | 5500.94 |
| 5513.60 | 5522.04 | 5530.48 |
| 5662.56 | 5675.33 | 5688.10 |
| 5688.70 | 5706.56 | 5724.42 |
| 5724.99 | 5735.14 | 5745.28 |
| 5749.00 | 5762.00 | 5775.00 |
| 5769.52 | 5779.10 | 5788.68 |
| 5788.88 | 5797.16 | 5805.44 |
| 5814.82 | 5824.40 | 5833.98 |
| 5829.00 | 5841.50 | 5854.00 |
| 5846.35 | 5866.50 | 5886.66 |
| 5925.42 | 5936.84 | 5948.25 |
| 5978.65 | 5988.93 | 5999.21 |
| 6000.51 | 6008.02 | 6015.54 |
| 6015.97 | 6029.24 | 6042.51 |
| 6100.95 | 6109.32 | 6117.69 |
| 6117.83 | 6127.05 | 6136.28 |
| 6277.96 | 6285.65 | 6293.35 |
| 6293.42 | 6300.21 | 6306.99 |
| 6311.64 | 6325.69 | 6339.75 |
| 6392.91 | 6404.05 | 6415.19 |
| 6417.64 | 6433.26 | 6448.89 |
| 6449.43 | 6457.72 | 6466.01 |
| 6466.28 | 6476.88 | 6487.48 |
| 6488.92 | 6498.60 | 6508.28 |
| 6508.87 | 6529.73 | 6550.58 |
| 6579.32 | 6592.59 | 6605.86 |
| 6606.66 | 6626.41 | 6646.17 |
| 6646.57 | 6656.45 | 6666.32 |
| 6666.52 | 6676.70 | 6686.88 |
| 6687.20 | 6698.07 | 6708.94 |
| 6709.21 | 6728.64 | 6748.07 |
| 6785.46 | 6801.92 | 6818.39 |
| 6824.37 | 6835.85 | 6847.32 |
| 6847.72 | 6858.90 | 6870.07 |
| 6870.67 | 6881.05 | 6891.42 |
| 6891.62 | 6900.70 | 6909.78 |
| 6912.98 | 6920.66 | 6928.34 |
| 6926.00 | 6937.00 | 6948.00 |
| 6928.00 | 6942.50 | 6957.00 |
| 6950.89 | 6964.26 | 6977.63 |
| 6970.00 | 6973.50 | 6977.00 |
| 6977.77 | 6989.03 | 7000.29 |
| 7023.74 | 7040.65 | 7057.55 |
| 7058.93 | 7073.87 | 7088.82 |
| 7118.40 | 7141.12 | 7163.85 |
| 7174.99 | 7186.67 | 7198.34 |

| Left | Center | Right |
| --- | --- | --- |
| 7229.92 | 7240.81 | 7251.70 |
| 7252.50 | 7265.78 | 7279.07 |
| 7280.16 | 7293.73 | 7307.30 |
| 7345.41 | 7356.19 | 7366.97 |
| 7373.55 | 7387.02 | 7400.49 |
| 7401.58 | 7408.92 | 7416.25 |
| 7417.45 | 7426.93 | 7436.41 |
| 7436.81 | 7446.59 | 7456.37 |
| 7456.50 | 7478.98 | 7501.47 |
| 7506.46 | 7518.23 | 7530.00 |
| 7597.25 | 7614.12 | 7630.98 |
| 7694.84 | 7705.91 | 7716.99 |
| 7717.87 | 7734.18 | 7750.48 |
| 7751.84 | 7776.03 | 7800.21 |
| 7809.18 | 7826.04 | 7842.91 |
| 8126.48 | 8144.14 | 8161.80 |
| 8189.74 | 8205.00 | 8220.27 |
| 8249.00 | 8262.67 | 8276.34 |
| 8346.79 | 8372.73 | 8398.67 |
| 8400.30 | 8419.35 | 8438.40 |
| 8454.83 | 8472.27 | 8489.71 |
| 8491.46 | 8503.54 | 8515.61 |
| 8516.41 | 8526.59 | 8536.76 |
| 8536.96 | 8543.75 | 8550.53 |
| 8550.93 | 8574.58 | 8598.23 |
| 8608.21 | 8623.67 | 8639.14 |
| 8645.12 | 8655.40 | 8665.68 |
| 8666.08 | 8688.23 | 8710.38 |
| 8710.58 | 8731.23 | 8751.89 |
| 8752.28 | 8766.55 | 8780.82 |
| 8781.82 | 8803.67 | 8825.52 |
| 8826.12 | 8852.66 | 8879.20 |
| 8883.59 | 8893.87 | 8904.15 |
| 8904.35 | 8925.80 | 8947.25 |
| 8947.45 | 8958.92 | 8970.39 |
| 8984.28 | 8993.64 | 9003.00 |
| 9005.76 | 9023.07 | 9040.38 |
| 9042.84 | 9065.99 | 9089.14 |
| 9099.51 | 9129.35 | 9159.18 |
| 9159.58 | 9170.35 | 9181.13 |
| 9181.33 | 9190.11 | 9198.89 |
| 9199.09 | 9213.36 | 9227.63 |
| 9248.19 | 9256.96 | 9265.73 |
| 9266.58 | 9283.28 | 9299.98 |
| 9301.66 | 9319.42 | 9337.18 |
| 9337.38 | 9357.24 | 9377.09 |
| 9377.49 | 9389.47 | 9401.44 |
| 9401.64 | 9438.56 | 9475.48 |
| 9502.42 | 9523.27 | 9544.12 |
| 9553.30 | 9569.27 | 9585.23 |
| 9585.63 | 9596.71 | 9607.78 |
| 9608.18 | 9635.42 | 9662.66 |
| 9644.00 | 9655.00 | 9666.00 |
| 9688.60 | 9711.45 | 9734.30 |
| 9762.93 | 9794.85 | 9826.77 |
| 9828.25 | 9862.61 | 9896.96 |
| 9902.13 | 9925.28 | 9948.42 |
| 10190.81 | 10206.39 | 10221.97 |
| 10235.00 | 10256.74 | 10278.47 |
| 10316.61 | 10335.66 | 10354.72 |
| 10367.89 | 10390.04 | 10412.19 |
| 10424.76 | 10446.32 | 10467.87 |
| 10495.89 | 10507.13 | 10518.38 |
| 10518.60 | 10532.01 | 10545.41 |
| 10558.85 | 10574.44 | 10590.04 |
| 10604.17 | 10626.82 | 10649.46 |
| 10689.38 | 10720.71 | 10752.04 |
| 10757.69 | 10772.29 | 10786.89 |
| 10768.37 | 10777.35 | 10786.32 |
| 10809.51 | 10838.94 | 10868.38 |
| 10897.80 | 10916.69 | 10935.58 |
| 10983.52 | 11000.18 | 11016.85 |
| 11021.68 | 11043.26 | 11064.85 |
| 11089.22 | 11103.28 | 11117.33 |
| 11132.98 | 11147.56 | 11162.15 |
| 11277.36 | 11302.94 | 11328.52 |
| 11351.38 | 11368.14 | 11384.89 |
| 11415.69 | 11436.82 | 11457.95 |
| 11458.55 | 11476.97 | 11495.38 |
| 11501.17 | 11526.51 | 11551.86 |
| 11610.33 | 11627.89 | 11645.45 |
| 11656.23 | 11678.78 | 11701.33 |
| 11701.57 | 11726.48 | 11751.39 |
| 11757.73 | 11782.33 | 11806.93 |
| 11810.08 | 11827.25 | 11844.41 |
| 11856.78 | 11874.44 | 11892.10 |
| 11892.70 | 11908.27 | 11923.83 |
| 11924.03 | 11945.78 | 11967.53 |
| 12265.27 | 12293.61 | 12321.95 |
| 12421.12 | 12449.86 | 12478.60 |
| 12531.68 | 12560.61 | 12589.55 |
| 12590.15 | 12614.39 | 12638.64 |
| 12644.23 | 12668.08 | 12691.92 |
| 12711.88 | 12734.33 | 12756.78 |
| 12760.97 | 12780.53 | 12800.08 |
| 12806.50 | 12865.74 | 12924.98 |
| 12932.39 | 12965.13 | 12997.87 |
| 13015.80 | 13062.37 | 13108.95 |
| 13116.38 | 13129.95 | 13139.00 |
| 13143.92 | 13161.28 | 13178.64 |
| 13227.86 | 13240.86 | 13253.86 |
| 13290.59 | 13314.34 | 13338.09 |
| 13340.88 | 13360.63 | 13380.39 |
| 13387.24 | 13410.82 | 13434.40 |
| 13476.88 | 13509.03 | 13541.19 |
| 13542.36 | 13563.60 | 13584.84 |
| 13585.23 | 13605.30 | 13625.38 |
| 13686.96 | 13711.90 | 13736.85 |
| 13737.24 | 13758.09 | 13778.94 |
| 13779.33 | 13798.43 | 13817.53 |
| 13817.92 | 13836.43 | 13854.94 |
| 13855.33 | 13877.75 | 13900.16 |
| 13900.94 | 13926.08 | 13951.22 |
| 13927.00 | 13939.50 | 13952.00 |
| 13939.00 | 13954.00 | 13969.00 |
| 13952.77 | 13975.96 | 13999.16 |
| 13999.55 | 14031.90 | 14064.24 |
| 14065.80 | 14091.92 | 14118.03 |
| 14119.20 | 14146.87 | 14174.55 |
| 14176.89 | 14197.93 | 14218.98 |
| 14220.54 | 14248.21 | 14275.88 |
| 14395.63 | 14421.89 | 14448.15 |
| 14450.50 | 14479.92 | 14509.35 |
| 14510.52 | 14533.90 | 14557.29 |
| 14558.46 | 14585.94 | 14613.41 |
| 14752.16 | 14779.33 | 14806.50 |
| 14852.08 | 14877.14 | 14902.19 |
| 14939.25 | 14971.99 | 15004.73 |
| 16426.96 | 16511.73 | 16596.50 |
| 16598.45 | 16664.52 | 16730.58 |
| 16995.62 | 17026.80 | 17057.98 |
| 17104.30 | 17121.88 | 17139.47 |
| 17139.72 | 17155.18 | 17170.65 |
| 17176.14 | 17200.08 | 17224.03 |
| 17226.03 | 17267.43 | 17308.84 |
| 17341.77 | 17390.41 | 17439.05 |
| 17440.05 | 17472.35 | 17504.66 |
| 17568.51 | 17600.69 | 17632.87 |
| 17772.43 | 17807.18 | 17841.94 |
| 17852.95 | 17876.12 | 17899.29 |
| 17969.21 | 18022.01 | 18074.81 |
| 18226.45 | 18273.65 | 18320.85 |
| 18433.51 | 18489.23 | 18544.96 |
| 18549.22 | 18617.73 | 18686.25 |
| 18687.46 | 18726.44 | 18765.41 |
| 18766.02 | 18792.21 | 18818.40 |
| 18819.01 | 18856.46 | 18893.91 |
| 19049.56 | 19092.01 | 19134.45 |
| 19492.83 | 19552.08 | 19611.34 |
| 19882.92 | 19942.61 | 20002.29 |
| 20474.87 | 20549.17 | 20623.46 |
| 20711.16 | 20806.16 | 20901.17 |
| 20902.99 | 20955.06 | 21007.13 |
| 21008.35 | 21066.81 | 21125.28 |

-continued

| Left | Center | Right |
| --- | --- | --- |
| 21126.50 | 21174.91 | 21223.33 |
| 21224.54 | 21277.22 | 21329.90 |
| 21331.12 | 21383.19 | 21435.26 |
| 21651.45 | 21695.30 | 21739.15 |
| 21739.76 | 21763.51 | 21787.26 |
| 21787.70 | 21814.48 | 21841.25 |

Example 1

Appendix B

Feature definitions derived from the 25 k shot spectra

| Left | Center | Right |
| --- | --- | --- |
| 3075.831 | 3085.942 | 3096.054 |
| 3100.514 | 3109.585 | 3118.655 |
| 3122.521 | 3129.956 | 3137.39 |
| 3189.73 | 3198.057 | 3206.384 |
| 3209.358 | 3217.685 | 3226.012 |
| 3234.338 | 3240.881 | 3247.423 |
| 3254.263 | 3261.252 | 3268.241 |
| 3276.865 | 3284.746 | 3292.626 |
| 3306.009 | 3315.079 | 3324.149 |
| 3387.195 | 3396.712 | 3406.228 |
| 3437.751 | 3446.227 | 3454.702 |
| 3544.513 | 3555.367 | 3566.222 |
| 3674.471 | 3684.731 | 3694.991 |
| 3808.295 | 3817.96 | 3827.625 |
| 3836.547 | 3844.279 | 3852.011 |
| 3883.236 | 3891.563 | 3899.89 |
| 3946.877 | 3953.717 | 3960.557 |
| 4003.678 | 4014.384 | 4025.09 |
| 4043.23 | 4051.557 | 4059.884 |
| 4240.695 | 4250.36 | 4260.025 |
| 4279.355 | 4290.507 | 4301.659 |
| 4334.372 | 4341.658 | 4348.944 |
| 4353.107 | 4361.732 | 4370.356 |
| 4373.032 | 4380.021 | 4387.009 |
| 4397.715 | 4407.232 | 4416.748 |
| 4419.722 | 4428.198 | 4436.673 |
| 4449.461 | 4463.884 | 4478.307 |
| 4562.17 | 4570.943 | 4579.716 |
| 4619.863 | 4626.554 | 4633.246 |
| 4636.22 | 4644.1 | 4651.981 |
| 4702.239 | 4711.756 | 4721.272 |
| 4767.962 | 4785.21 | 4802.459 |
| 4847.067 | 4854.947 | 4862.828 |
| 4882.456 | 4891.377 | 4900.299 |
| 4928.848 | 4936.729 | 4944.61 |
| 5056.724 | 5065.497 | 5074.27 |
| 5076.352 | 5084.084 | 5091.816 |
| 5095.385 | 5105.347 | 5115.31 |
| 5122.447 | 5130.03 | 5137.614 |
| 5139.695 | 5146.981 | 5154.267 |
| 5281.846 | 5290.619 | 5299.392 |
| 5398.719 | 5405.559 | 5412.399 |
| 5746.959 | 5763.167 | 5779.374 |
| 5790.08 | 5797.069 | 5804.057 |
| 5814.763 | 5822.347 | 5829.93 |
| 5834.688 | 5843.907 | 5853.126 |
| 5857.587 | 5866.062 | 5874.538 |
| 5880.188 | 5890.745 | 5901.303 |
| 6187.984 | 6196.608 | 6205.232 |
| 6277.794 | 6286.27 | 6294.745 |
| 6324.484 | 6332.067 | 6339.651 |
| 6407.752 | 6447.751 | 6487.749 |
| 6519.867 | 6530.87 | 6541.874 |
| 6601.054 | 6653.542 | 6706.031 |
| 6714.358 | 6727.443 | 6740.528 |
| 6794.95 | 6803.425 | 6811.901 |
| 6827.365 | 6837.476 | 6847.587 |
| 6850.859 | 6858.888 | 6866.917 |

-continued

| Left | Center | Right |
| --- | --- | --- |
| 6870.486 | 6881.489 | 6892.493 |
| 6912.12 | 6920.001 | 6927.882 |
| 6929.369 | 6941.562 | 6953.754 |
| 6955.836 | 6964.312 | 6972.787 |
| 7031.67 | 7044.606 | 7057.542 |
| 7177.984 | 7185.121 | 7192.259 |
| 7282.961 | 7293.519 | 7304.076 |
| 7378.72 | 7386.601 | 7394.482 |
| 7475.668 | 7485.184 | 7494.701 |
| 7551.799 | 7565.33 | 7578.861 |
| 7602.057 | 7615.44 | 7628.822 |
| 7661.237 | 7671.349 | 7681.46 |
| 7755.212 | 7765.025 | 7774.839 |
| 7813.202 | 7822.867 | 7832.532 |
| 7922.343 | 7939.145 | 7955.948 |
| 8007.098 | 8016.912 | 8026.726 |
| 8029.7 | 8042.636 | 8055.572 |
| 8134.082 | 8144.342 | 8154.602 |
| 8189.694 | 8204.117 | 8218.54 |
| 8402.92 | 8410.652 | 8418.384 |
| 8420.168 | 8428.049 | 8435.93 |
| 8517.711 | 8527.228 | 8536.744 |
| 8552.505 | 8561.576 | 8570.646 |
| 8573.917 | 8582.988 | 8592.058 |
| 8613.47 | 8624.473 | 8635.476 |
| 8647.074 | 8655.104 | 8663.133 |
| 8668.486 | 8686.627 | 8704.767 |
| 8709.823 | 8721.867 | 8733.911 |
| 8735.696 | 8743.428 | 8751.16 |
| 8754.728 | 8765.286 | 8775.843 |
| 8794.281 | 8809.745 | 8825.209 |
| 8835.023 | 8848.257 | 8861.49 |
| 8862.382 | 8870.858 | 8879.333 |
| 8901.935 | 8924.685 | 8947.435 |
| 8986.095 | 8994.571 | 9003.046 |
| 9007.21 | 9016.577 | 9025.945 |
| 9047.06 | 9066.985 | 9086.909 |
| 9109.213 | 9137.168 | 9165.122 |
| 9270.694 | 9282.144 | 9293.593 |
| 9306.083 | 9313.816 | 9321.548 |
| 9331.064 | 9353.071 | 9375.077 |
| 9400.355 | 9438.421 | 9476.486 |
| 9552.617 | 9568.527 | 9584.437 |
| 9613.284 | 9638.562 | 9663.84 |
| 9688.523 | 9716.328 | 9744.134 |
| 9901.749 | 9927.473 | 9953.197 |
| 10246.12 | 10256.98 | 10267.83 |
| 10330.28 | 10340.54 | 10350.8 |
| 10433.18 | 10445.67 | 10458.16 |
| 10516.45 | 10528.49 | 10540.54 |
| 10561.06 | 10575.78 | 10590.5 |
| 10820.38 | 10839.56 | 10858.74 |
| 11418.76 | 11437.81 | 11456.86 |
| 11494.96 | 11522.84 | 11550.72 |
| 11606.48 | 11626.69 | 11646.91 |
| 11660.85 | 11679.9 | 11698.95 |
| 11705.92 | 11733.8 | 11761.68 |
| 11764 | 11785.15 | 11806.29 |
| 11813.72 | 11825.8 | 11837.89 |
| 11861.12 | 11890.86 | 11920.6 |
| 11923.85 | 11944.76 | 11965.67 |
| 12279.32 | 12293.03 | 12306.73 |
| 12429.87 | 12450.08 | 12470.3 |
| 12546.97 | 12566.48 | 12586 |
| 12595.29 | 12607.61 | 12619.92 |
| 12657.09 | 12668.01 | 12678.93 |
| 12712.85 | 12727.72 | 12742.59 |
| 12830.41 | 12863.41 | 12896.4 |
| 12942.86 | 12962.38 | 12981.9 |
| 13051.13 | 13072.74 | 13094.34 |
| 13115.25 | 13127.57 | 13139.88 |
| 13145.46 | 13155.22 | 13164.97 |
| 13302.05 | 13315.99 | 13329.93 |
| 13598.04 | 13608.03 | 13618.02 |
| 13703.06 | 13719.09 | 13735.12 |
| 13742.55 | 13759.98 | 13777.4 |
| 13780.19 | 13792.04 | 13803.89 |

| Left | Center | Right |
|---|---|---|
| 13827.12 | 13842.46 | 13857.79 |
| 13861.97 | 13881.72 | 13901.47 |
| 13910.3 | 13920.75 | 13931.21 |
| 13933.07 | 13942.59 | 13952.12 |
| 13958.16 | 13977.91 | 13997.66 |
| 14017.17 | 14036.22 | 14055.28 |
| 14074.79 | 14093.61 | 14112.43 |
| 14122.19 | 14144.49 | 14166.8 |
| 14174.69 | 14192.12 | 14209.54 |
| 14465.58 | 14482.54 | 14499.5 |
| 14515.3 | 14536.21 | 14557.12 |
| 14763.89 | 14779.46 | 14795.02 |
| 17010.56 | 17025.43 | 17040.29 |
| 17113.25 | 17140.43 | 17167.61 |
| 17235.45 | 17263.33 | 17291.21 |
| 17364.17 | 17387.87 | 17411.56 |
| 17446.41 | 17459.42 | 17472.43 |
| 17575.59 | 17597.89 | 17620.2 |
| 18258.65 | 18273.98 | 18289.32 |
| 18485.87 | 18500.28 | 18514.68 |
| 18561.15 | 18577.18 | 18593.21 |
| 18614.12 | 18634.8 | 18655.48 |
| 20824.08 | 20844.29 | 20864.5 |
| 20926.3 | 20957.2 | 20988.1 |
| 21035.5 | 21066.4 | 21097.3 |
| 21142.84 | 21168.39 | 21193.95 |
| 21242.28 | 21269.69 | 21297.11 |
| 22587.95 | 22611.65 | 22635.35 |
| 23003.36 | 23039.84 | 23076.32 |

Example 2

Appendix A: Feature Definitions

The same 300 features listed in Example 1 Appendix A were used in classifier generation.

Example 2

Appendix B

Feature Definitions of Stable Features

| Left | Center | Right |
|---|---|---|
| 3350.649 | 3365.195 | 3379.741 |
| 3451.331 | 3462.145 | 3472.958 |
| 3473.429 | 3484.007 | 3494.586 |
| 3524.537 | 3550.157 | 3575.778 |
| 3662.644 | 3679.799 | 3696.955 |
| 3787.022 | 3810.493 | 3833.965 |
| 3940.773 | 3951.939 | 3963.106 |
| 3994.298 | 4013.968 | 4033.638 |
| 4034.299 | 4053.308 | 4072.317 |
| 4273.643 | 4289.346 | 4305.048 |
| 4327.528 | 4338.272 | 4349.016 |
| 4349.347 | 4359.264 | 4369.182 |
| 4394.717 | 4411.347 | 4427.977 |
| 4445.547 | 4462.738 | 4479.928 |
| 4614.584 | 4633.839 | 4653.095 |
| 4694.147 | 4712.329 | 4730.512 |
| 4762.248 | 4782.744 | 4803.24 |
| 4874.647 | 4890.184 | 4905.722 |
| 4923.904 | 4936.466 | 4949.028 |
| 5050.518 | 5064.072 | 5077.626 |
| 5090.188 | 5105.726 | 5121.263 |
| 5273.332 | 5287.713 | 5302.093 |
| 5394.988 | 5407.55 | 5420.112 |
| 5420.854 | 5430.492 | 5440.131 |
| 5685.241 | 5705.076 | 5724.912 |
| 5805.905 | 5821.442 | 5836.98 |
| 5889.874 | 5906.733 | 5923.593 |
| 5978.47 | 5988.109 | 5997.747 |
| 5998.452 | 6008.443 | 6018.434 |
| 6175.169 | 6192.194 | 6209.219 |
| 6263.104 | 6286.906 | 6310.708 |
| 6311.37 | 6332.692 | 6354.015 |
| 6403.978 | 6431.811 | 6459.644 |
| 6507.407 | 6528.233 | 6549.06 |
| 6596.536 | 6632.422 | 6668.308 |
| 6708.072 | 6729.89 | 6751.709 |
| 6821.129 | 6834.477 | 6847.825 |
| 6867.956 | 6879.772 | 6891.588 |
| 6909.094 | 6919.597 | 6930.1 |
| 6930.975 | 6946.292 | 6961.61 |
| 7173.396 | 7188.559 | 7203.722 |
| 7283.415 | 7297.402 | 7311.39 |
| 7369.242 | 7386.267 | 7403.292 |
| 7455.194 | 7472.219 | 7489.244 |
| 7542.786 | 7565.762 | 7588.738 |
| 7589.613 | 7612.37 | 7635.127 |
| 7801.647 | 7825.615 | 7849.582 |
| 7908.647 | 7934.905 | 7961.163 |
| 8180.855 | 8202.737 | 8224.619 |
| 8397.707 | 8408.638 | 8419.57 |
| 8419.805 | 8431.559 | 8443.313 |
| 8514.389 | 8527.447 | 8540.505 |
| 8748.112 | 8764.642 | 8781.171 |
| 9001.01 | 9015.225 | 9029.44 |
| 9097.259 | 9133.364 | 9169.468 |
| 9269.445 | 9285.148 | 9300.851 |
| 9548.459 | 9568.294 | 9588.129 |
| 9601.412 | 9638.392 | 9675.372 |
| 9678.435 | 9709.945 | 9741.455 |
| 9896.896 | 9931.938 | 9966.98 |
| 10316.41 | 10346.66 | 10376.91 |
| 10553.44 | 10577.74 | 10602.03 |
| 10602.7 | 10642.7 | 10682.7 |
| 10685.01 | 10719.72 | 10754.43 |
| 10803.36 | 10837.91 | 10872.45 |
| 11351.66 | 11371.84 | 11392.01 |
| 11504.11 | 11529.22 | 11554.33 |
| 11704.87 | 11727.35 | 11749.83 |
| 11917.43 | 11943.05 | 11968.67 |
| 12528.68 | 12564.22 | 12599.76 |
| 12813.98 | 12855.96 | 12897.95 |
| 12933.65 | 12960.43 | 12987.21 |
| 13745.24 | 13761.77 | 13778.3 |
| 13822.26 | 13839.45 | 13856.64 |
| 13858.63 | 13879.29 | 13899.95 |
| 13923.42 | 13937.64 | 13951.85 |
| 13955.16 | 13975.32 | 13995.49 |
| 14004.09 | 14035.33 | 14066.57 |
| 14069.21 | 14087.72 | 14106.24 |
| 18585.43 | 18631.04 | 18676.65 |
| 28026.88 | 28099.85 | 28172.82 |
| 28174.44 | 28213.97 | 28253.49 |

Example 2

Appendix C

Reduced Set of Features Used in Classifiers

| m/Z |
|---|
| 3043 |
| 3109 |
| 3132 |
| 3286 |
| 3335 |
| 3708 |
| 3797 |
| 3891 |

-continued

| m/Z |
|---|
| 3929 |
| 3954 |
| 4015 |
| 4053 |
| 4267 |
| 4291 |
| 4379 |
| 4530 |
| 4600 |
| 4627 |
| 4647 |
| 4757 |
| 4792 |
| 4891 |
| 5045 |
| 5065 |
| 5148 |
| 5196 |
| 5270 |
| 5474 |
| 5522 |
| 5561 |
| 5675 |
| 5779 |
| 5867 |
| 5906 |
| 6008 |
| 6286 |
| 6859 |
| 6881 |
| 6901 |
| 6937 |
| 6943 |
| 6964 |
| 6974 |
| 7041 |
| 7294 |
| 7409 |
| 7614 |
| 7826 |
| 8144 |
| 8504 |
| 8624 |
| 8731 |
| 8853 |
| 9066 |
| 9170 |
| 9190 |
| 9213 |
| 9257 |
| 9389 |
| 9439 |
| 9523 |
| 9655 |
| 9795 |
| 9863 |
| 10532 |
| 10627 |
| 10721 |
| 10839 |
| 10917 |
| 11437 |
| 11477 |
| 11726 |
| 11874 |
| 11946 |
| 13130 |
| 13161 |
| 13509 |
| 13564 |
| 13605 |
| 13712 |
| 13758 |
| 13798 |
| 13878 |
| 13940 |
| 13954 |

-continued

| m/Z |
|---|
| 14032 |
| 14092 |
| 14147 |
| 14422 |
| 14480 |
| 14534 |
| 17122 |
| 17876 |
| 18274 |
| 18489 |
| 19552 |
| 20549 |
| 20955 |
| 21067 |
| 21175 |
| "30000" (AFP) |

We claim:

1. A method of detecting a class label in a liver disease patient comprising:
    a) conducting mass spectrometry on a blood-based sample of the patient and obtaining mass spectrometry data;
    (b) obtaining integrated intensity values in the mass spectral data of a multitude of pre-determined mass-spectral features; and
    (c) operating on the mass spectral data with a programmed computer implementing a classifier;
    wherein in the operating step the classifier compares the integrated intensity values with feature values of a training set of class-labeled mass spectral data obtained from a multitude of other patients with liver disease with the values obtained in step (b) with a classification algorithm and detects a class label for the sample.

2. The method of claim 1, wherein the mass spectrometry comprises performing MALDI-TOF mass spectrometry by subjecting the blood-based sample to at least 100,000 laser shots and acquiring mass spectral data.

3. The method of claim 1, wherein the classifier is obtained from filtered mini-classifiers combined using a regularized combination method.

4. The method of claim 3, wherein the mini-classifiers perform classifications using single features, pairs of features, or single features, pairs of features and triplets of features in the feature values of a training set.

5. The method of claim 1, wherein the obtaining step (b) comprises obtaining integrated intensity values of at least 50 features listed in one of the Appendices.

6. The method of claim 5, wherein the obtaining step comprises obtaining integrated intensity values of at least 100 features listed in Example 1 Appendix A or Example 2 Appendix C.

7. The method of claim 5, wherein the obtaining step comprises obtaining integrated intensity values of all the features of one of the Appendices.

8. The method of claim 1, wherein the training set comprises all or a subset of a set of samples used to develop the classifier.

9. The method of claim 8, wherein the training set is a subset of the set of samples used to develop the classifier pruned to remove those patients who have high AFP expression levels.

10. The method of claim 1, wherein the feature values consist of the mass spectral features and AFP expression level.

* * * * *